United States Patent
Lermontova

(10) Patent No.: US 11,483,990 B2
(45) Date of Patent: Nov. 1, 2022

(54) GENERATION OF HAPOLOID PLANTS BASED ON KNL2

(71) Applicant: LEIBNIZ-INSTITUT FÜR PFLANZENGENETIK UND KULTURPFLANZENFORSCHUNG (IPK), Stadt Seeland/OT Gatersleben (DE)

(72) Inventor: Inna Lermontova, Halberstadt (DE)

(73) Assignee: LEIBNIZ-INSTITUT FÜR PFLANZENGENETIK UND KULTURPFLANZENFORSCHUNG, Gatersleben (DE)

( * ) Notice: Subject to any disclaimer, the term of this patent is extended or adjusted under 35 U.S.C. 154(b) by 290 days.

(21) Appl. No.: 15/770,049

(22) PCT Filed: Sep. 13, 2016

(86) PCT No.: PCT/EP2016/071559
§ 371 (c)(1),
(2) Date: Apr. 20, 2018

(87) PCT Pub. No.: WO2017/067714
PCT Pub. Date: Apr. 27, 2017

(65) Prior Publication Data
US 2019/0075744 A1   Mar. 14, 2019

(30) Foreign Application Priority Data

Oct. 22, 2015 (EP) ..................... 15191078

(51) Int. Cl.
| | | |
|---|---|---|
| *A01H 1/08* | (2006.01) | |
| *C12N 15/82* | (2006.01) | |
| *A01H 1/02* | (2006.01) | |
| *C07K 14/415* | (2006.01) | |
| *A01H 1/04* | (2006.01) | |

(52) U.S. Cl.
CPC .............. *A01H 1/08* (2013.01); *A01H 1/02* (2013.01); *A01H 1/04* (2013.01); *C07K 14/415* (2013.01); *C12N 15/8261* (2013.01); *C12N 15/8267* (2013.01); *C12N 15/8287* (2013.01); *Y02A 40/146* (2018.01)

(58) Field of Classification Search
None
See application file for complete search history.

(56) References Cited

U.S. PATENT DOCUMENTS

2011/0083202 A1   4/2011   Chan et al.

FOREIGN PATENT DOCUMENTS

WO   2014/110274 A2   7/2014

OTHER PUBLICATIONS

Lermontova et al (2013, "Arabidopsis Kinetochore Null2 is an Upstream Component for Centromeric Histone H3 Variant cenH3 Deposition at Centromeres", The Plant Cell 25:3389-3404).*
Lermontova et al The Plant Cell 25:3389-3404 Provided by Applicant (Year: 2013).*
International Search Report dated Dec. 20, 2016 for corresponding International Application No. PCT/EP2016/071559.
Written Opinion dated Dec. 20, 2016 for corresponding International Application No. PCT/EP2016/071559.
I. Lermontova et al: "*Arabidopsis* Kinetochore Null2 is an Upstream Component for Centromeric Histone H3 Variant cenH3 Deposition at Centromeres", The Plant Cell, vol. 25, No. 9, Sep. 1, 2013, pp. 3389-3404, XP055246251.
J. Mach: "Putting the cenH3 in the Centromere: *Arabidopsis* Kinetochore Null2 Acts Upstream of cenH3 Deposition", The Plant Cell, vol. 25, No. 9, Sep. 1, 2013, pp. 3149-3149, XP055246263.
Inna Lermontova et al: "Centromeres and kinetochores of Brassicaceae", Chromosome Research, vol. 22, No. 2, May 7, 2014, pp. 135-152, XP055246756.
Sundaram Kuppu et al: "Point Mutations in Centromeric Histone Induce Post-zygotic Incompatibility and Uniparental Inheritance", PLOS Genetics, vol. 11, No. 9, Sep. 9, 2015, p. e1005494, XP055246211.
Raheleh Karimi-Ashtiyani et al: "Point mutation impairs centromeric CENH3 loading and induces haploid plants", Proceedings of the National Academy of Sciences, vol. 112, No. 36, Aug. 20, 2015, pp. 11211-11216, XP055233787.
Pooja Bhatnagar-Mathur et al: "Engineering Centromeres for Haploidy Induction in Grain Legumes", ICRISAT Asia Regional Planning Meeting, Patancheru, India, Feb. 10-12, 2014, Feb. 1, 2014, XP055193834, Retrieved from the Internet: URL:http://ksiconnect.icrisat.org/wp-conte nt/uploads/2014/02/6Pooja-DH-for-haploids.pdf.
B. Moree et al: "CENP-C recruits M18BP1 to centromeres to promote CENP-A chromatin assembly", Molecular Cell., vol. 13, No. 3, Sep. 19, 2011, pp. 73-871, XP055246291.
Inna Lermontova et al: "CENH3 for Establishing and Maintaining Centromeres" In: "Plant Centromere Biology", Apr. 8, 2013 (Apr. 8, 2013), John Wiley & Sons, Oxford [u.a.], XP055163252.

(Continued)

*Primary Examiner* — Brent T Page
(74) *Attorney, Agent, or Firm* — Pearne & Gordon LLP

(57) ABSTRACT

The present invention relates to non-transgenic and transgenic plants, preferably crop plants, comprising at least one mutation of the KINTEOCHORE NULL2 (KNL2) protein, especially a mutation causing a substitution of an amino acid within the KNL2 protein, preferably within the C-terminal region of the KNL2 protein, which preferably have the biological activity of a haploid inducer. Further, the present invention provides methods of generating the plants of the present invention and haploid and double haploid plants obtainable by crossing the plants of the present invention with wildtype plants as well as methods of facilitating cytoplasm exchange.

23 Claims, 3 Drawing Sheets
Specification includes a Sequence Listing.

(56) References Cited

OTHER PUBLICATIONS

Maruthachalam Ravi et al: "A haploid genetics toolbox for *Arabidopsis thaliana*", Nature Communications, vol. 5, Oct. 31, 2014, p. 5334, XP055191112.

M. Ravi et al: 11 The Rapidly Evolving Centromere-Specific Histone has Stringent Functional Requirements in *Arabidopsis thaliana*, Genetics, vol. 186, No. 2, Jul. 13, 2010, pp. 461-471, XP055142479.

Chan et al: "Chromosome engineering: power tools for plant genetics", Trends in Biotechnology, Elsevier Publications, Cambridge, GB, vol. 28, No. 12, Dec. 1, 2010, pp. 605-610, XP027483988.

Valerie De Rop et al: "CENP-A: the key player behind centromere identity, propagation, and kinetochore assembly", Chromosoma; Biology of the Nucleus, Springer, Berlin, DE, vol. 121, No. 6, Oct. 26, 2012, pp. 527-538, XP035140321.

Izabel C. R. Moraes: "Structural requirements for CENH3 targeting to centromeric chromatin", Feb. 1, 2011, XP055191122, Retrieved from the Internet: URL:http://d-nb.info/1025136047/34.

H. Kato: "A conserved Mechanism for centromeric nucleosome recognition by centromere protein CENP-C", Science, vol. 340, No. 6136, Apr. 18, 2013, pp. 1110-1113, XP055327749.

H Kato et al: "Supplementary Materials for a Conserved Mechanism for Centromeric Nucleosome Recognition by Centromere Protein CENP-C", Mar. 31, 2013, XP055327699, Retrieved from the Internet: URL:https://www.ncbi.nlm.nih.gov/pmc/articles/PMC3763809/bin/NIHMS509826-supplement-Supplemental_Data.pdf.

Sandmann et al., "Targeting of *Arabidopsis* KNL2 to Centromeres Depends on the Conserved CENPC-k Motif in its C Terminus", The Plant Cell, vol. 29, pp. 144-155, Jan. 2017.

Mach; "A Tale of two CENPCs: Centromere Localization of Kinetochore Null2 and CENP-C", The Plant Cell, vol. 29, pp. 2-3, Jan. 2017.

* cited by examiner

```
CENP-C        GGVRRST--RIKSRPLEYWRGERFLYGRIHESLTTV--
KNL2          LGQKRSRSGRVLVSSLEFWRNQIPVYD-MDRNLIQVKD
```

CENP-C = SEQ ID No. 2   KNL2 = SEQ ID No. 4

B)

```
Arabidopsis      LGQKRSRSGRVLVSSLEFWRNQIPVYDMDRNLIQVKD   (SEQ ID No.4)
Alyrata          VGQKRSRSGRVLVSSLEFWRNQIPVYDMDRNLIQVKD   (SEQ ID No.5)
Capsella         LGQKRSRSGRVLVSPLEFWRNQIPVYDMDRNLIQVKD   (SEQ ID No.6)
Glycine          PSFRKSRSGRLLLPPLEFWRNQIPIYNADHEITEIQD   (SEQ ID No.7)
Glycine_isoI     LSFRKSRSGRLLLPPLEFWRNQIPIYNADHEITEIRD   (SEQ ID No.8)
Phaseolus        SNFRTSRSGRMLLPPLEFWRNQIPIYDADHELKEIKD   (SEQ ID No.9)
Medicago2        LGLKKSRSGRWLLPRLEFWRNQTPIYNMDREIIEIQE   (SEQ ID No.10)
Medicago         LSLKKSRSGRWLLPPLEFWRNQQPIYNMDREITEIQE   (SEQ ID No.11)
Cicer            LSLKKSRSGRLLLPPLEFWHNQKPIYNVDREITEIQA   (SEQ ID No.12)
Citrus_sinensis  LSLKRSRSGRLLVPCLDFWRNQIAVYDADRNITGIQE   (SEQ ID No.13)
Vitis            LSLKRSRSGRLLLPSLDFWRNQKAVYDADRRITGIQE   (SEQ ID No.14)
Theobroma        LSLKCSRSGRLLLPRLEFWRNQIAVYDQTRKITGIRE   (SEQ ID No.15)
Solanum          LSFNRSRSGRVLLPPMAFWRNQRAVYDVILFTTGISC   (SEQ ID No.16)
Populus          LNLKRSRSGRLLLPTLDFWRNQIPVYDEVSGISGIFP   (SEQ ID No.17)
Fragaria         LSTGRSRSGRLLLRPLEFWRNQSPVYDKDHGVIGIQE   (SEQ ID No.18)
Fragaria1        LSAGRSRSGRLRLRPLEFWRNQSAVYDKDHGVIGIQE   (SEQ ID No.19)
Amborella        FLLSISRSGRIIVRPLAYWCNERIVYGKDGSITSILD   (SEQ ID No.20)
Physcomitrella   FGLKTSRSGRLLVPALAYWRSQSIEYDKDGGIIAIFD   (SEQ ID No.21)
Oryza*           LKLRRTRSGRVVVPTLDPG-CQRIVYDRDGLVSGVAGL  (SEQ ID No.22)
```

Figure 2
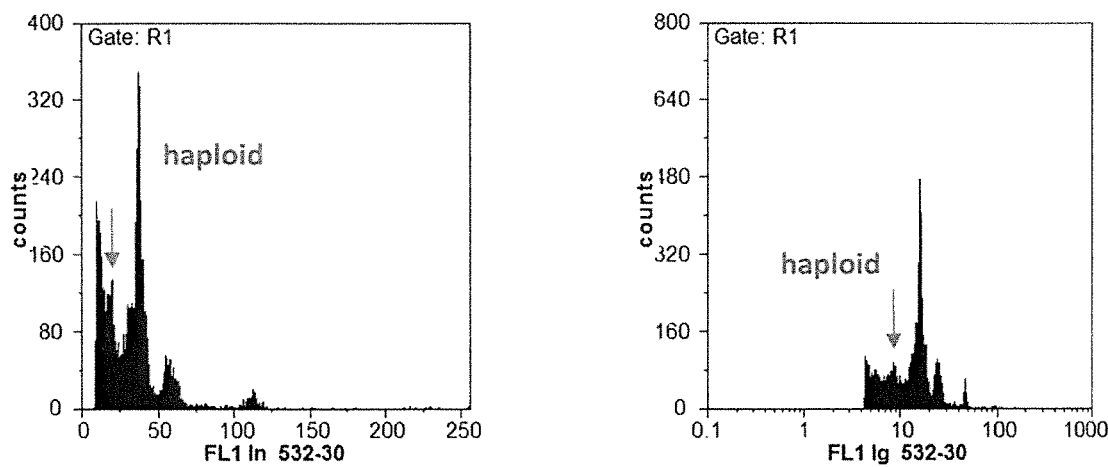
kn12 x Col (2 seeds)
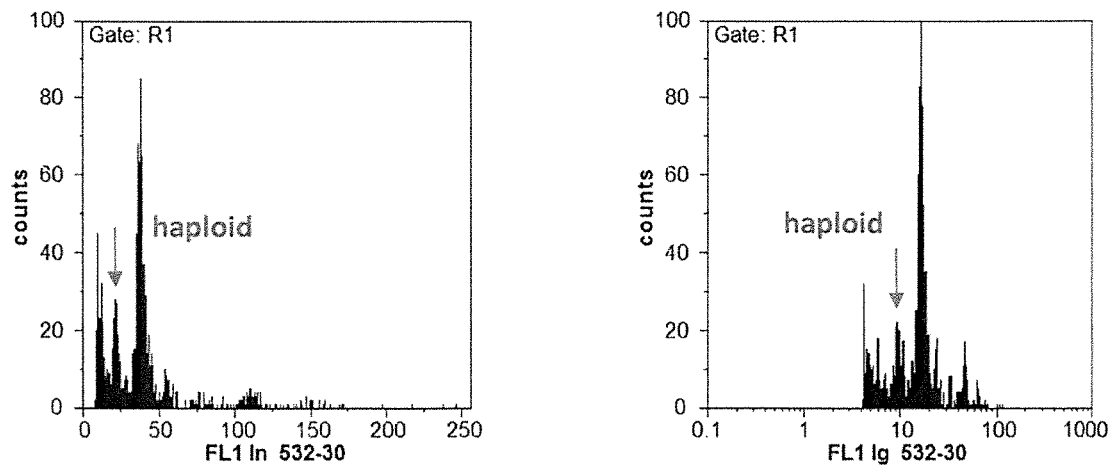

Figure 3
A)
B)
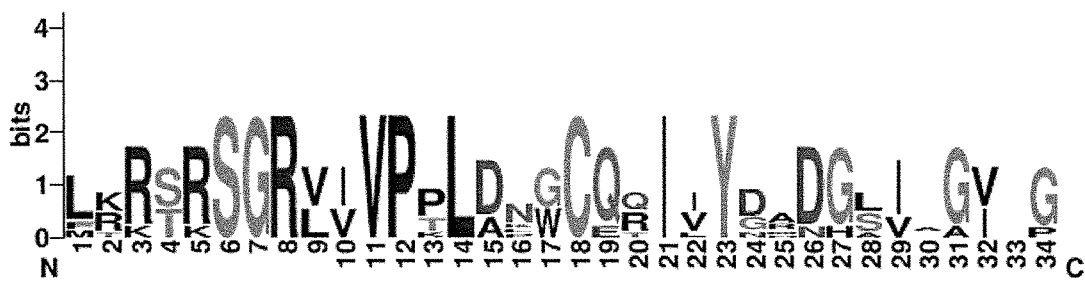
C)
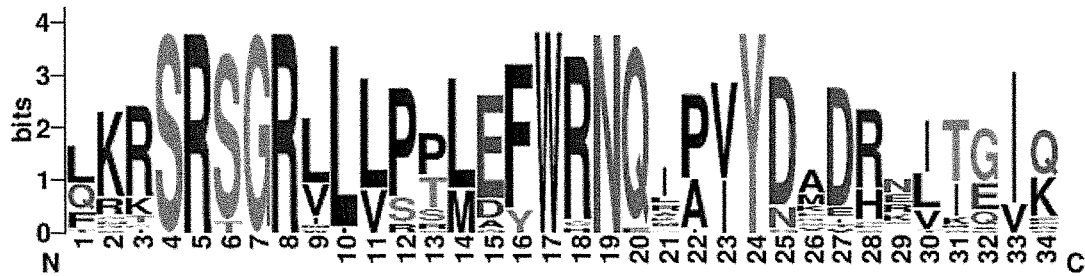

SEQUENCE LISTING

<160> NUMBER OF SEQ ID NOS: 274

<210> SEQ ID NO 1
<211> LENGTH: 1797
<212> TYPE: DNA
<213> ORGANISM: Arabidopsis thaliana

<400> SEQUENCE: 1

```
atgacggaac caaatctcga cgaagatggt tccaagtcgt ctttccagaa acggtggtg    60
ctgagagatt ggtggttgat aaaatgccca aggaattcg aagggaaaca atttggtgtt   120
gctggattcg aagagtccgt cgagacaaga gcaatgcgtg tgtttacatc ttcaccaatc   180
accaaagctt tggatgtttt cacactctta gcatctgatg gaatctatat cactctcaga   240
ggttttctta caaagaacg cgttcttaaa aatggattta accctgagat ttctcgtgaa   300
ttcatcttcg ggtttcctcc ttgttgggaa cgagtttgta acagttgctt tgaaggagac   360
tcttttggca ctgatgttaa taccgtccct tcgactatcg agaaagcttg tcctcccatt   420
ttatcacctt gtaagtactc taacaggaat cttaaggata tccagctga gagcagagag    480
aaaagcaatg tgactgagac tgatattgca gagattaatg ataaaggtgg ttctggagca   540
agagatataa aaactgcaag gagaaggtct cttcatctgc aaataaaaag gatacttgaa   600
tcgagtaaag tccggaagac tgctaatgat ggagatcatg tagtgaatt tttgaatacg    660
gctaagcgcg tgatgtaga agagatgga tgtgaggtta tcaataatga agacagtgaa   720
tggaaactcg atgaaagtga agtccagaat cttttgtaatg atggagataa tggtagtgaa   780
ggtttcatta aggctaagag cagtgatgta gaaaaagata gagcgaagc tatcgataat   840
gatgtgatat ctccagcggt tggaagtggt attaagcata ccggtgcaga taatgttgat   900
aaagtgacaa gtgcaagtgc tactggagaa tcacttactt cggaacagca aaatggttta   960
cttgtaacaa cagcatctcc acattccctg cttaaagact tagccaagag tagcaaaacct  1020
gaaaagaaag aatatccaa gaaagtggc aagatcctca gaagtgacga caatgtagta  1080
gatcccatga attactctgg gacgaaagtc aaaagtgcgg aaaacaaaag gaaaatcgat   1140
gcgagtaaac tccagagtcc gactagtaat gttgcagaaac atagtaagga aggtttaaat  1200
aatgctaaga gcaatgacgt agaaaaagat gtatgtgtgg ctatcaataa tgaagtgata  1260
tcaccagtga agggatttgg taaaaggctt tctggtacag atgttgaaag attaacaagt  1320
aagaatgcta ctaaagaatc actgacgtca gtacagcgaa aaggtagagt gaaggtatcg  1380
aaggcatttc aagatcccct gtcgaaagga aaatcaaaga aaagtgagaa gacccttcaa  1440
agtaacagca atgttgtaga gcctatgaat catttcaggt ctgaagctga agaagctgaa  1500
gaaaacttgt catgggaaaa aataaagagg aaaatcgact ttgatgtgga ggtaacaccg  1560
gaaaaaaaag tgaagcagca aagaccaat gcggcgtcta ctgattcatt gggacagaaa  1620
cggtcaagat caggaagggt gcttgtgtca tcactagagt tttggcgtaa ccaaattcct  1680
gtttatgata tggatcggaa ccttatccaa gtaaaggatg gtagtgagac taactccgct  1740
ccatctaaag gaaaaggatc ggattctcga aagcgaagaa acttgaaaat caaataa      1797
```

<210> SEQ ID NO 2
<211> LENGTH: 34
<212> TYPE: PRT
<213> ORGANISM: Arabidopsis thaliana

<400> SEQUENCE: 2

Gly Gly Val Arg Arg Ser Thr Arg Ile Lys Ser Arg Pro Leu Glu Tyr
1               5                   10                  15

Trp Arg Gly Glu Arg Phe Leu Tyr Gly Arg Ile His Glu Ser Leu Thr
            20                  25                  30

Thr Val

<210> SEQ ID NO 3
<211> LENGTH: 598

```
<212> TYPE: PRT
<213> ORGANISM: Arabidopsis thaliana
<220> FEATURE:
<223> OTHER INFORMATION: AT5G02520

<400> SEQUENCE: 3

Met Thr Glu Pro Asn Leu Asp Glu Asp Gly Ser Lys Ser Phe Gln
1               5                   10                  15

Lys Thr Val Val Leu Arg Asp Trp Trp Leu Ile Lys Cys Pro Lys Glu
            20                  25                  30

Phe Glu Gly Lys Gln Phe Gly Val Ala Gly Phe Glu Glu Ser Val Glu
                35                  40                  45

Thr Arg Ala Met Arg Val Phe Thr Ser Pro Ile Thr Lys Ala Leu
50                  55                  60

Asp Val Phe Thr Leu Leu Ala Ser Asp Gly Ile Tyr Ile Thr Leu Arg
65                  70                  75                  80

Gly Phe Leu Asn Lys Glu Arg Val Leu Lys Asn Gly Phe Asn Pro Glu
                85                  90                  95

Ile Ser Arg Glu Phe Ile Phe Gly Phe Pro Pro Cys Trp Glu Arg Val
                100                 105                 110

Cys Asn Ser Cys Phe Glu Gly Asp Ser Phe Gly Thr Asp Val Asn Thr
                115                 120                 125

Val Pro Ser Thr Ile Glu Lys Ala Cys Pro Pro Ile Leu Ser Pro Cys
130                 135                 140

Lys Tyr Ser Asn Arg Asn Leu Lys Asp Asn Pro Ala Glu Ser Arg Glu
145                 150                 155                 160

Lys Ser Asn Val Thr Glu Thr Asp Ile Ala Glu Ile Asn Asp Lys Gly
                165                 170                 175

Gly Ser Gly Ala Arg Asp Ile Lys Thr Ala Arg Arg Ser Leu His
                180                 185                 190

Leu Gln Ile Lys Arg Ile Leu Glu Ser Ser Lys Val Arg Lys Thr Ala
                195                 200                 205

Asn Asp Gly Asp His Gly Ser Glu Phe Leu Asn Thr Ala Lys Arg Gly
210                 215                 220

Asp Val Glu Arg Asp Gly Cys Glu Val Ile Asn Asn Glu Asp Ser Glu
225                 230                 235                 240

Trp Lys Leu Asp Glu Ser Glu Val Gln Asn Leu Cys Asn Asp Gly Asp
                245                 250                 255

Asn Gly Ser Glu Gly Phe Ile Lys Ala Lys Ser Ser Asp Val Glu Lys
                260                 265                 270

Asp Lys Ser Glu Ala Ile Asp Asn Asp Val Ile Ser Pro Ala Val Gly
            275                 280                 285

Ser Gly Ile Lys His Thr Gly Ala Asp Asn Val Asp Lys Val Thr Ser
            290                 295                 300

Ala Ser Ala Thr Gly Glu Ser Leu Thr Ser Glu Gln Gln Asn Gly Leu
305                 310                 315                 320

Leu Val Thr Thr Ala Ser Pro His Ser Leu Leu Lys Asp Leu Ala Lys
                325                 330                 335

Ser Ser Lys Pro Glu Lys Lys Gly Ile Ser Lys Lys Ser Gly Lys Ile
                340                 345                 350

Leu Arg Ser Asp Asp Asn Val Val Asp Pro Met Asn Tyr Ser Gly Thr
                355                 360                 365

Lys Val Lys Ser Ala Glu Asn Lys Arg Lys Ile Asp Ala Ser Lys Leu
370                 375                 380
```

-continued

Gln Ser Pro Thr Ser Asn Val Ala Glu His Ser Lys Glu Gly Leu Asn
385                 390                 395                 400

Asn Ala Lys Ser Asn Asp Val Glu Lys Asp Val Cys Val Ala Ile Asn
            405                 410                 415

Asn Glu Val Ile Ser Pro Val Lys Gly Phe Gly Lys Arg Leu Ser Gly
        420                 425                 430

Thr Asp Val Glu Arg Leu Thr Ser Lys Asn Ala Thr Lys Glu Ser Leu
    435                 440                 445

Thr Ser Val Gln Arg Lys Gly Arg Val Lys Val Ser Lys Ala Phe Gln
450                 455                 460

Asp Pro Leu Ser Lys Gly Lys Ser Lys Ser Glu Lys Thr Leu Gln
465                 470                 475                 480

Ser Asn Ser Asn Val Val Glu Pro Met Asn His Phe Arg Ser Glu Ala
            485                 490                 495

Glu Glu Ala Glu Glu Asn Leu Ser Trp Glu Lys Ile Lys Arg Lys Ile
            500                 505                 510

Asp Phe Asp Val Glu Val Thr Pro Glu Lys Val Lys Gln Gln Lys
    515                 520                 525

Thr Asn Ala Ala Ser Thr Asp Ser Leu Gly Gln Lys Arg Ser Arg Ser
530                 535                 540

Gly Arg Val Leu Val Ser Ser Leu Glu Phe Trp Arg Asn Gln Ile Pro
545                 550                 555                 560

Val Tyr Asp Met Asp Arg Asn Leu Ile Gln Val Lys Asp Gly Ser Glu
                565                 570                 575

Thr Asn Ser Ala Pro Ser Lys Gly Lys Gly Ser Asp Ser Arg Lys Arg
            580                 585                 590

Arg Asn Leu Lys Ile Lys
        595

<210> SEQ ID NO 4
<211> LENGTH: 37
<212> TYPE: PRT
<213> ORGANISM: Arabidopsis thaliana

<400> SEQUENCE: 4

Leu Gly Gln Lys Arg Ser Arg Ser Gly Arg Val Leu Val Ser Ser Leu
1               5                   10                  15

Glu Phe Trp Arg Asn Gln Ile Pro Val Tyr Asp Met Asp Arg Asn Leu
            20                  25                  30

Ile Gln Val Lys Asp
        35

<210> SEQ ID NO 5
<211> LENGTH: 37
<212> TYPE: PRT
<213> ORGANISM: Arabidopsis lyrata

<400> SEQUENCE: 5

Val Gly Gln Lys Arg Ser Arg Ser Gly Arg Val Leu Val Ser Ser Leu
1               5                   10                  15

Glu Phe Trp Arg Asn Gln Ile Pro Val Tyr Asp Met Asp Arg Asn Leu
            20                  25                  30

Ile Gln Val Lys Asp
        35

<210> SEQ ID NO 6
<211> LENGTH: 37

```
<212> TYPE: PRT
<213> ORGANISM: Capsella

<400> SEQUENCE: 6

Leu Gly Gln Lys Arg Ser Arg Ser Gly Arg Val Leu Val Ser Pro Leu
1               5                   10                  15

Glu Phe Trp Arg Asn Gln Ile Pro Val Tyr Asp Met Asp Arg Asn Leu
            20                  25                  30

Ile Gln Val Lys Asp
        35

<210> SEQ ID NO 7
<211> LENGTH: 37
<212> TYPE: PRT
<213> ORGANISM: Glycine

<400> SEQUENCE: 7

Pro Ser Phe Arg Lys Ser Arg Ser Gly Arg Leu Leu Leu Pro Pro Leu
1               5                   10                  15

Glu Phe Trp Arg Asn Gln Ile Pro Ile Tyr Asn Ala Asp His Glu Ile
            20                  25                  30

Thr Glu Ile Gln Asp
        35

<210> SEQ ID NO 8
<211> LENGTH: 37
<212> TYPE: PRT
<213> ORGANISM: Glycine
<220> FEATURE:
<223> OTHER INFORMATION: alternative Sequence of Glycine

<400> SEQUENCE: 8

Leu Ser Phe Arg Lys Ser Arg Ser Gly Arg Leu Leu Leu Pro Pro Leu
1               5                   10                  15

Glu Phe Trp Arg Asn Gln Ile Pro Ile Tyr Asn Ala Asp His Glu Ile
            20                  25                  30

Thr Glu Ile Arg Asp
        35

<210> SEQ ID NO 9
<211> LENGTH: 37
<212> TYPE: PRT
<213> ORGANISM: Phaseolus

<400> SEQUENCE: 9

Ser Asn Phe Arg Thr Ser Arg Ser Gly Arg Met Leu Leu Pro Pro Leu
1               5                   10                  15

Glu Phe Trp Arg Asn Gln Ile Pro Ile Tyr Asp Ala Asp His Glu Leu
            20                  25                  30

Lys Glu Ile Lys Asp
        35

<210> SEQ ID NO 10
<211> LENGTH: 37
<212> TYPE: PRT
<213> ORGANISM: Medicago

<400> SEQUENCE: 10

Leu Gly Leu Lys Lys Ser Arg Ser Gly Arg Trp Leu Leu Pro Arg Leu
1               5                   10                  15

Glu Phe Trp Arg Asn Gln Thr Pro Ile Tyr Asn Met Asp Arg Glu Ile
```

```
              20                  25                  30

Ile Glu Ile Gln Glu
        35

<210> SEQ ID NO 11
<211> LENGTH: 37
<212> TYPE: PRT
<213> ORGANISM: Medicago

<400> SEQUENCE: 11

Leu Ser Leu Lys Lys Ser Arg Ser Gly Arg Trp Leu Leu Pro Pro Leu
1               5                  10                  15

Glu Phe Trp Arg Asn Gln Gln Pro Ile Tyr Asn Met Asp Arg Glu Ile
              20                  25                  30

Thr Glu Ile Gln Glu
        35

<210> SEQ ID NO 12
<211> LENGTH: 37
<212> TYPE: PRT
<213> ORGANISM: Cicer

<400> SEQUENCE: 12

Leu Ser Leu Lys Lys Ser Arg Ser Gly Arg Leu Leu Leu Pro Pro Leu
1               5                  10                  15

Glu Phe Trp His Asn Gln Lys Pro Ile Tyr Asn Val Asp Arg Glu Ile
              20                  25                  30

Thr Glu Ile Gln Ala
        35

<210> SEQ ID NO 13
<211> LENGTH: 37
<212> TYPE: PRT
<213> ORGANISM: Citrus sinensis

<400> SEQUENCE: 13

Leu Ser Leu Lys Arg Ser Arg Ser Gly Arg Leu Leu Val Pro Cys Leu
1               5                  10                  15

Asp Phe Trp Arg Asn Gln Ile Ala Val Tyr Asp Ala Asp Arg Asn Ile
              20                  25                  30

Thr Gly Ile Gln Glu
        35

<210> SEQ ID NO 14
<211> LENGTH: 37
<212> TYPE: PRT
<213> ORGANISM: Vitis

<400> SEQUENCE: 14

Leu Ser Leu Lys Arg Ser Arg Ser Gly Arg Leu Leu Leu Pro Ser Leu
1               5                  10                  15

Asp Phe Trp Arg Asn Gln Lys Ala Val Tyr Asp Ala Asp Arg Arg Ile
              20                  25                  30

Thr Gly Ile Gln Glu
        35

<210> SEQ ID NO 15
<211> LENGTH: 37
<212> TYPE: PRT
<213> ORGANISM: Theobroma
```

```
<400> SEQUENCE: 15

Leu Ser Leu Lys Cys Ser Arg Ser Gly Arg Leu Leu Leu Pro Arg Leu
1               5                   10                  15

Glu Phe Trp Arg Asn Gln Ile Ala Val Tyr Asp Gln Thr Arg Lys Ile
            20                  25                  30

Thr Gly Ile Arg Glu
        35

<210> SEQ ID NO 16
<211> LENGTH: 37
<212> TYPE: PRT
<213> ORGANISM: Solanum

<400> SEQUENCE: 16

Leu Ser Phe Asn Arg Ser Arg Ser Gly Arg Val Leu Leu Pro Pro Met
1               5                   10                  15

Ala Phe Trp Arg Asn Gln Arg Ala Val Tyr Asp Val Ile Leu Phe Thr
            20                  25                  30

Thr Gly Ile Ser Cys
        35

<210> SEQ ID NO 17
<211> LENGTH: 37
<212> TYPE: PRT
<213> ORGANISM: Populus

<400> SEQUENCE: 17

Leu Asn Leu Lys Arg Ser Arg Ser Gly Arg Leu Leu Leu Pro Thr Leu
1               5                   10                  15

Asp Phe Trp Arg Asn Gln Ile Pro Val Tyr Asp Glu Val Ser Gly Ile
            20                  25                  30

Ser Gly Ile Phe Pro
        35

<210> SEQ ID NO 18
<211> LENGTH: 37
<212> TYPE: PRT
<213> ORGANISM: Fragaria

<400> SEQUENCE: 18

Leu Ser Thr Gly Arg Ser Arg Ser Gly Arg Leu Leu Leu Arg Pro Leu
1               5                   10                  15

Glu Phe Trp Arg Asn Gln Ser Pro Val Tyr Asp Lys Asp His Gly Val
            20                  25                  30

Ile Gly Ile Gln Glu
        35

<210> SEQ ID NO 19
<211> LENGTH: 37
<212> TYPE: PRT
<213> ORGANISM: Fragaria

<400> SEQUENCE: 19

Leu Ser Ala Gly Arg Ser Arg Ser Gly Arg Leu Arg Leu Arg Pro Leu
1               5                   10                  15

Glu Phe Trp Arg Asn Gln Ser Ala Val Tyr Asp Lys Asp His Gly Val
            20                  25                  30

Ile Gly Ile Gln Glu
        35
```

<210> SEQ ID NO 20
<211> LENGTH: 37
<212> TYPE: PRT
<213> ORGANISM: Amborella

<400> SEQUENCE: 20

Phe Leu Leu Ser Ile Ser Arg Ser Gly Arg Ile Ile Val Arg Pro Leu
1               5                   10                  15

Ala Tyr Trp Cys Asn Glu Arg Ile Val Tyr Gly Lys Asp Gly Ser Ile
            20                  25                  30

Thr Ser Ile Leu Asp
        35

<210> SEQ ID NO 21
<211> LENGTH: 37
<212> TYPE: PRT
<213> ORGANISM: Physcomitrella

<400> SEQUENCE: 21

Phe Gly Leu Lys Thr Ser Arg Ser Gly Arg Leu Leu Val Pro Ala Leu
1               5                   10                  15

Ala Tyr Trp Arg Ser Gln Ser Ile Glu Tyr Asp Lys Asp Gly Gly Ile
            20                  25                  30

Ile Ala Ile Phe Asp
        35

<210> SEQ ID NO 22
<211> LENGTH: 37
<212> TYPE: PRT
<213> ORGANISM: Oryza

<400> SEQUENCE: 22

Leu Lys Leu Arg Arg Thr Arg Ser Gly Arg Val Val Pro Thr Leu
1               5                   10                  15

Asp Pro Gly Cys Gln Arg Ile Val Tyr Asp Arg Asp Gly Leu Val Ser
            20                  25                  30

Gly Val Ala Gly Leu
        35

<210> SEQ ID NO 23
<211> LENGTH: 4
<212> TYPE: PRT
<213> ORGANISM: Arabidopsis thaliana
<220> FEATURE:
<221> NAME/KEY: SITE
<222> LOCATION: 4
<223> OTHER INFORMATION: Xaa can be any naturally occuring amino acid

<400> SEQUENCE: 23

Arg Ser Gly Xaa
1

<210> SEQ ID NO 24
<211> LENGTH: 4
<212> TYPE: PRT
<213> ORGANISM: Arabidopsis thaliana

<400> SEQUENCE: 24

Arg Ser Gly Ala
1

<210> SEQ ID NO 25

```
<211> LENGTH: 4
<212> TYPE: PRT
<213> ORGANISM: Arabidopsis thaliana
<220> FEATURE:
<221> NAME/KEY: SITE
<222> LOCATION: 1
<223> OTHER INFORMATION: Xaa can be any naturally occuring amino acid

<400> SEQUENCE: 25

Xaa Arg Asn Gln
1

<210> SEQ ID NO 26
<211> LENGTH: 4
<212> TYPE: PRT
<213> ORGANISM: Arabidopsis thaliana

<400> SEQUENCE: 26

Arg Arg Asn Gln
1

<210> SEQ ID NO 27
<211> LENGTH: 528
<212> TYPE: PRT
<213> ORGANISM: Arabidopsis thaliana
<220> FEATURE:
<221> NAME/KEY: SITE
<222> LOCATION: 476
<223> OTHER INFORMATION: Xaa can be any naturally occuring amino acid
<220> FEATURE:
<221> NAME/KEY: SITE
<222> LOCATION: 485
<223> OTHER INFORMATION: Xaa can be any naturally occuring amino acid

<400> SEQUENCE: 27

Ala Ser Asp Gly Ile Tyr Ile Thr Leu Arg Gly Phe Leu Asn Lys Glu
1               5                   10                  15

Arg Val Leu Lys Asn Gly Phe Asn Pro Glu Ile Ser Arg Glu Phe Ile
            20                  25                  30

Phe Gly Phe Pro Pro Cys Trp Glu Arg Val Cys Asn Ser Cys Phe Glu
        35                  40                  45

Gly Asp Ser Phe Gly Thr Asp Val Asn Thr Val Pro Ser Thr Ile Glu
    50                  55                  60

Lys Ala Cys Pro Pro Ile Leu Ser Pro Cys Lys Tyr Ser Asn Arg Asn
65                  70                  75                  80

Leu Lys Asp Asn Pro Ala Glu Ser Arg Glu Lys Ser Asn Val Thr Glu
                85                  90                  95

Thr Asp Ile Ala Glu Ile Asn Asp Lys Gly Ser Gly Ala Arg Asp
            100                 105                 110

Ile Lys Thr Ala Arg Arg Ser Leu His Leu Gln Ile Lys Arg Ile
        115                 120                 125

Leu Glu Ser Ser Lys Val Arg Lys Thr Ala Asn Asp Gly Asp His Gly
130                 135                 140

Ser Glu Phe Leu Asn Thr Ala Lys Arg Gly Asp Val Glu Arg Asp Gly
145                 150                 155                 160

Cys Glu Val Ile Asn Asn Glu Asp Ser Glu Trp Lys Leu Asp Glu Ser
                165                 170                 175

Glu Val Gln Asn Leu Cys Asn Asp Gly Asp Asn Gly Ser Glu Gly Phe
            180                 185                 190

Ile Lys Ala Lys Ser Ser Asp Val Glu Lys Asp Lys Ser Glu Ala Ile
        195                 200                 205
```

```
Asp Asn Asp Val Ile Ser Pro Ala Val Gly Ser Gly Ile Lys His Thr
    210                 215                 220

Gly Ala Asp Asn Val Asp Lys Val Thr Ser Ala Ser Ala Thr Gly Glu
225                 230                 235                 240

Ser Leu Thr Ser Glu Gln Gln Asn Gly Leu Leu Val Thr Thr Ala Ser
                245                 250                 255

Pro His Ser Leu Leu Lys Asp Leu Ala Lys Ser Ser Lys Pro Glu Lys
            260                 265                 270

Lys Gly Ile Ser Lys Lys Ser Gly Lys Ile Leu Arg Ser Asp Asp Asn
                275                 280                 285

Val Val Asp Pro Met Asn Tyr Ser Gly Thr Lys Val Lys Ser Ala Glu
290                 295                 300

Asn Lys Arg Lys Ile Asp Ala Ser Lys Leu Gln Ser Pro Thr Ser Asn
305                 310                 315                 320

Val Ala Glu His Ser Lys Gly Leu Asn Asn Ala Lys Ser Asn Asp
                325                 330                 335

Val Glu Lys Asp Val Cys Val Ala Ile Asn Asn Glu Val Ile Ser Pro
                340                 345                 350

Val Lys Gly Phe Gly Lys Arg Leu Ser Gly Thr Asp Val Glu Arg Leu
            355                 360                 365

Thr Ser Lys Asn Ala Thr Lys Glu Ser Leu Thr Ser Val Gln Arg Lys
    370                 375                 380

Gly Arg Val Lys Val Ser Lys Ala Phe Gln Asp Pro Leu Ser Lys Gly
385                 390                 395                 400

Lys Ser Lys Lys Ser Glu Lys Thr Leu Gln Ser Asn Ser Asn Val Val
                405                 410                 415

Glu Pro Met Asn His Phe Arg Ser Glu Ala Glu Glu Ala Glu Asn
            420                 425                 430

Leu Ser Trp Glu Lys Ile Lys Arg Lys Ile Asp Phe Asp Val Glu Val
            435                 440                 445

Thr Pro Glu Lys Lys Val Lys Gln Gln Lys Thr Asn Ala Ala Ser Thr
    450                 455                 460

Asp Ser Leu Gly Gln Lys Arg Ser Arg Ser Gly Xaa Val Leu Val Ser
465                 470                 475                 480

Ser Leu Glu Phe Xaa Arg Asn Gln Ile Pro Val Tyr Asp Met Asp Arg
                485                 490                 495

Asn Leu Ile Gln Val Lys Asp Gly Ser Glu Thr Asn Ser Ala Pro Ser
            500                 505                 510

Lys Gly Lys Gly Ser Asp Ser Arg Lys Arg Asn Leu Lys Ile Lys
            515                 520                 525
```

<210> SEQ ID NO 28
<211> LENGTH: 598
<212> TYPE: PRT
<213> ORGANISM: Arabidopsis thaliana

<400> SEQUENCE: 28

```
Met Thr Glu Pro Asn Leu Asp Glu Asp Gly Ser Lys Ser Ser Phe Gln
1               5                   10                  15

Lys Thr Val Val Leu Arg Asp Trp Trp Leu Ile Lys Cys Pro Lys Glu
            20                  25                  30

Phe Glu Gly Lys Gln Phe Gly Val Ala Gly Phe Glu Glu Ser Val Glu
        35                  40                  45

Thr Arg Ala Met Arg Val Phe Thr Ser Ser Pro Ile Thr Lys Ala Leu
    50                  55                  60
```

```
Asp Val Phe Thr Leu Leu Ala Ser Asp Gly Ile Tyr Ile Thr Leu Arg
 65                  70                  75                  80

Gly Phe Leu Asn Lys Glu Arg Val Leu Lys Asn Gly Phe Asn Pro Glu
             85                   90                  95

Ile Ser Arg Glu Phe Ile Phe Gly Phe Pro Pro Cys Trp Glu Arg Val
            100                 105                 110

Cys Asn Ser Cys Phe Glu Gly Asp Ser Phe Gly Thr Asp Val Asn Thr
            115                 120                 125

Val Pro Ser Thr Ile Glu Lys Ala Cys Pro Pro Ile Leu Ser Pro Cys
130                 135                 140

Lys Tyr Ser Asn Arg Asn Leu Lys Asp Asn Pro Ala Glu Ser Arg Glu
145                 150                 155                 160

Lys Ser Asn Val Thr Glu Thr Asp Ile Ala Glu Ile Asn Asp Lys Gly
                165                 170                 175

Gly Ser Gly Ala Arg Asp Ile Lys Thr Ala Arg Arg Ser Leu His
                180                 185                 190

Leu Gln Ile Lys Arg Ile Leu Glu Ser Ser Lys Val Arg Lys Thr Ala
            195                 200                 205

Asn Asp Gly Asp His Gly Ser Glu Phe Leu Asn Thr Ala Lys Arg Gly
210                 215                 220

Asp Val Glu Arg Asp Gly Cys Glu Val Ile Asn Asn Glu Asp Ser Glu
225                 230                 235                 240

Trp Lys Leu Asp Glu Ser Glu Val Gln Asn Leu Cys Asn Asp Gly Asp
                245                 250                 255

Asn Gly Ser Glu Gly Phe Ile Lys Ala Lys Ser Ser Asp Val Glu Lys
                260                 265                 270

Asp Lys Ser Glu Ala Ile Asp Asn Asp Val Ile Ser Pro Ala Val Gly
            275                 280                 285

Ser Gly Ile Lys His Thr Gly Ala Asp Asn Val Asp Lys Val Thr Ser
            290                 295                 300

Ala Ser Ala Thr Gly Glu Ser Leu Thr Ser Glu Gln Gln Asn Gly Leu
305                 310                 315                 320

Leu Val Thr Thr Ala Ser Pro His Ser Leu Lys Asp Leu Ala Lys
                325                 330                 335

Ser Ser Lys Pro Glu Lys Lys Gly Ile Ser Lys Lys Ser Gly Lys Ile
                340                 345                 350

Leu Arg Ser Asp Asp Asn Val Val Asp Pro Met Asn Tyr Ser Gly Thr
            355                 360                 365

Lys Val Lys Ser Ala Glu Asn Lys Arg Lys Ile Asp Ala Ser Lys Leu
            370                 375                 380

Gln Ser Pro Thr Ser Asn Val Ala Glu His Ser Lys Glu Gly Leu Asn
385                 390                 395                 400

Asn Ala Lys Ser Asn Asp Val Glu Lys Asp Val Cys Val Ala Ile Asn
                405                 410                 415

Asn Glu Val Ile Ser Pro Val Lys Gly Phe Gly Lys Arg Leu Ser Gly
            420                 425                 430

Thr Asp Val Glu Arg Leu Thr Ser Lys Asn Ala Thr Lys Glu Ser Leu
            435                 440                 445

Thr Ser Val Gln Arg Lys Gly Arg Val Lys Val Ser Lys Ala Phe Gln
    450                 455                 460

Asp Pro Leu Ser Lys Gly Lys Ser Lys Lys Ser Glu Lys Thr Leu Gln
465                 470                 475                 480
```

Ser Asn Ser Asn Val Val Glu Pro Met Asn His Phe Arg Ser Glu Ala
            485                 490                 495

Glu Glu Ala Glu Glu Asn Leu Ser Trp Glu Lys Ile Lys Arg Lys Ile
        500                 505                 510

Asp Phe Asp Val Glu Val Thr Pro Glu Lys Lys Val Lys Gln Gln Lys
        515                 520                 525

Thr Asn Ala Ala Ser Thr Asp Ser Leu Gly Gln Lys Arg Ser Arg Ser
    530                 535                 540

Gly Ala Val Leu Val Ser Ser Leu Glu Phe Trp Arg Asn Gln Ile Pro
545                 550                 555                 560

Val Tyr Asp Met Asp Arg Asn Leu Ile Gln Val Lys Asp Gly Ser Glu
            565                 570                 575

Thr Asn Ser Ala Pro Ser Lys Gly Lys Gly Ser Asp Ser Arg Lys Arg
        580                 585                 590

Arg Asn Leu Lys Ile Lys
        595

<210> SEQ ID NO 29
<211> LENGTH: 598
<212> TYPE: PRT
<213> ORGANISM: Arabidopsis thaliana

<400> SEQUENCE: 29

Met Thr Glu Pro Asn Leu Asp Glu Asp Gly Ser Lys Ser Ser Phe Gln
1               5                   10                  15

Lys Thr Val Val Leu Arg Asp Trp Trp Leu Ile Lys Cys Pro Lys Glu
            20                  25                  30

Phe Glu Gly Lys Gln Phe Gly Val Ala Gly Phe Glu Glu Ser Val Glu
        35                  40                  45

Thr Arg Ala Met Arg Val Phe Thr Ser Ser Pro Ile Thr Lys Ala Leu
    50                  55                  60

Asp Val Phe Thr Leu Leu Ala Ser Asp Gly Ile Tyr Ile Thr Leu Arg
65                  70                  75                  80

Gly Phe Leu Asn Lys Glu Arg Val Leu Lys Asn Gly Phe Asn Pro Glu
            85                  90                  95

Ile Ser Arg Glu Phe Ile Phe Gly Phe Pro Pro Cys Trp Glu Arg Val
        100                 105                 110

Cys Asn Ser Cys Phe Glu Gly Asp Ser Phe Gly Thr Asp Val Asn Thr
    115                 120                 125

Val Pro Ser Thr Ile Glu Lys Ala Cys Pro Pro Ile Leu Ser Pro Cys
130                 135                 140

Lys Tyr Ser Asn Arg Asn Leu Lys Asp Asn Pro Ala Glu Ser Arg Glu
145                 150                 155                 160

Lys Ser Asn Val Thr Glu Thr Asp Ile Ala Glu Ile Asn Asp Lys Gly
            165                 170                 175

Gly Ser Gly Ala Arg Asp Ile Lys Thr Ala Arg Arg Ser Leu His
        180                 185                 190

Leu Gln Ile Lys Arg Ile Leu Glu Ser Ser Lys Val Arg Lys Thr Ala
    195                 200                 205

Asn Asp Gly Asp His Gly Ser Glu Phe Leu Asn Thr Ala Lys Arg Gly
210                 215                 220

Asp Val Glu Arg Asp Gly Cys Glu Val Ile Asn Asn Glu Asp Ser Glu
225                 230                 235                 240

Trp Lys Leu Asp Glu Ser Glu Val Gln Asn Leu Cys Asn Asp Gly Asp
            245                 250                 255

Asn Gly Ser Glu Gly Phe Ile Lys Ala Lys Ser Ser Asp Val Glu Lys
            260                 265                 270

Asp Lys Ser Glu Ala Ile Asp Asn Asp Val Ile Ser Pro Ala Val Gly
        275                 280                 285

Ser Gly Ile Lys His Thr Gly Ala Asp Asn Val Asp Lys Val Thr Ser
    290                 295                 300

Ala Ser Ala Thr Gly Glu Ser Leu Thr Ser Glu Gln Gln Asn Gly Leu
305                 310                 315                 320

Leu Val Thr Thr Ala Ser Pro His Ser Leu Leu Lys Asp Leu Ala Lys
                325                 330                 335

Ser Ser Lys Pro Glu Lys Lys Gly Ile Ser Lys Lys Ser Gly Lys Ile
            340                 345                 350

Leu Arg Ser Asp Asp Asn Val Val Asp Pro Met Asn Tyr Ser Gly Thr
        355                 360                 365

Lys Val Lys Ser Ala Glu Asn Lys Arg Lys Ile Asp Ala Ser Lys Leu
    370                 375                 380

Gln Ser Pro Thr Ser Asn Val Ala Glu His Ser Lys Glu Gly Leu Asn
385                 390                 395                 400

Asn Ala Lys Ser Asn Asp Val Glu Lys Asp Val Cys Val Ala Ile Asn
                405                 410                 415

Asn Glu Val Ile Ser Pro Val Lys Gly Phe Gly Lys Arg Leu Ser Gly
            420                 425                 430

Thr Asp Val Glu Arg Leu Thr Ser Lys Asn Ala Thr Lys Glu Ser Leu
        435                 440                 445

Thr Ser Val Gln Arg Lys Gly Arg Val Lys Val Ser Lys Ala Phe Gln
    450                 455                 460

Asp Pro Leu Ser Lys Gly Lys Ser Lys Ser Glu Lys Thr Leu Gln
465                 470                 475                 480

Ser Asn Ser Asn Val Val Glu Pro Met Asn His Phe Arg Ser Glu Ala
                485                 490                 495

Glu Glu Ala Glu Glu Asn Leu Ser Trp Glu Lys Ile Lys Arg Lys Ile
            500                 505                 510

Asp Phe Asp Val Glu Val Thr Pro Glu Lys Lys Val Lys Gln Gln Lys
        515                 520                 525

Thr Asn Ala Ala Ser Thr Asp Ser Leu Gly Gln Lys Arg Ser Arg Ser
    530                 535                 540

Gly Arg Val Leu Val Ser Ser Leu Glu Phe Arg Arg Asn Gln Ile Pro
545                 550                 555                 560

Val Tyr Asp Met Asp Arg Asn Leu Ile Gln Val Lys Asp Gly Ser Glu
                565                 570                 575

Thr Asn Ser Ala Pro Ser Lys Gly Lys Gly Ser Asp Ser Arg Lys Arg
            580                 585                 590

Arg Asn Leu Lys Ile Lys
        595

<210> SEQ ID NO 30
<211> LENGTH: 598
<212> TYPE: PRT
<213> ORGANISM: Arabidopsis thaliana

<400> SEQUENCE: 30

Met Thr Glu Pro Asn Leu Asp Glu Asp Gly Ser Lys Ser Ser Phe Gln
1               5                   10                  15

Lys Thr Val Val Leu Arg Asp Trp Trp Leu Ile Lys Cys Pro Lys Glu

```
                20                  25                  30
Phe Glu Gly Lys Gln Phe Gly Val Ala Gly Phe Glu Glu Ser Val Glu
                35                  40                  45
Thr Arg Ala Met Arg Val Phe Thr Ser Ser Pro Ile Thr Lys Ala Leu
 50                  55                  60
Asp Val Phe Thr Leu Leu Ala Ser Asp Gly Ile Tyr Ile Thr Leu Arg
 65                  70                  75                  80
Gly Phe Leu Asn Lys Glu Arg Val Leu Lys Asn Gly Phe Asn Pro Glu
                85                  90                  95
Ile Ser Arg Glu Phe Ile Phe Gly Phe Pro Pro Cys Trp Glu Arg Val
                100                 105                 110
Cys Asn Ser Cys Phe Glu Gly Asp Ser Phe Gly Thr Asp Val Asn Thr
                115                 120                 125
Val Pro Ser Thr Ile Glu Lys Ala Cys Pro Pro Ile Leu Ser Pro Cys
                130                 135                 140
Lys Tyr Ser Asn Arg Asn Leu Lys Asp Asn Pro Ala Glu Ser Arg Glu
145                 150                 155                 160
Lys Ser Asn Val Thr Glu Thr Asp Ile Ala Glu Ile Asn Asp Lys Gly
                165                 170                 175
Gly Ser Gly Ala Arg Asp Ile Lys Thr Ala Arg Arg Ser Leu His
                180                 185                 190
Leu Gln Ile Lys Arg Ile Leu Glu Ser Ser Lys Val Arg Lys Thr Ala
                195                 200                 205
Asn Asp Gly Asp His Gly Ser Glu Phe Leu Asn Thr Ala Lys Arg Gly
                210                 215                 220
Asp Val Glu Arg Asp Gly Cys Glu Val Ile Asn Asn Glu Asp Ser Glu
225                 230                 235                 240
Trp Lys Leu Asp Glu Ser Glu Val Gln Asn Leu Cys Asn Asp Gly Asp
                245                 250                 255
Asn Gly Ser Glu Gly Phe Ile Lys Ala Lys Ser Ser Asp Val Glu Lys
                260                 265                 270
Asp Lys Ser Glu Ala Ile Asp Asn Asp Val Ile Ser Pro Ala Val Gly
                275                 280                 285
Ser Gly Ile Lys His Thr Gly Ala Asp Asn Val Asp Lys Val Thr Ser
                290                 295                 300
Ala Ser Ala Thr Gly Glu Ser Leu Thr Ser Glu Gln Gln Asn Gly Leu
305                 310                 315                 320
Leu Val Thr Thr Ala Ser Pro His Ser Leu Leu Lys Asp Leu Ala Lys
                325                 330                 335
Ser Ser Lys Pro Glu Lys Lys Gly Ile Ser Lys Lys Ser Gly Lys Ile
                340                 345                 350
Leu Arg Ser Asp Asp Asn Val Val Asp Pro Met Asn Tyr Ser Gly Thr
                355                 360                 365
Lys Val Lys Ser Ala Glu Asn Lys Arg Lys Ile Asp Ala Ser Lys Leu
                370                 375                 380
Gln Ser Pro Thr Ser Asn Val Ala Glu His Ser Lys Glu Gly Leu Asn
385                 390                 395                 400
Asn Ala Lys Ser Asn Asp Val Glu Lys Asp Val Cys Val Ala Ile Asn
                405                 410                 415
Asn Glu Val Ile Ser Pro Val Lys Gly Phe Gly Lys Arg Leu Ser Gly
                420                 425                 430
Thr Asp Val Glu Arg Leu Thr Ser Lys Asn Ala Thr Lys Glu Ser Leu
                435                 440                 445
```

```
Thr Ser Val Gln Arg Lys Gly Arg Val Lys Val Ser Lys Ala Phe Gln
    450                 455                 460

Asp Pro Leu Ser Lys Gly Lys Ser Lys Lys Ser Glu Lys Thr Leu Gln
465                 470                 475                 480

Ser Asn Ser Asn Val Val Glu Pro Met Asn His Phe Arg Ser Glu Ala
                485                 490                 495

Glu Glu Ala Glu Glu Asn Leu Ser Trp Glu Lys Ile Lys Arg Lys Ile
            500                 505                 510

Asp Phe Asp Val Glu Val Thr Pro Glu Lys Lys Val Lys Gln Gln Lys
        515                 520                 525

Thr Asn Ala Ala Ser Thr Asp Ser Leu Gly Gln Lys Arg Ser Arg Ser
    530                 535                 540

Gly Ala Val Leu Val Ser Ser Leu Glu Phe Arg Arg Asn Gln Ile Pro
545                 550                 555                 560

Val Tyr Asp Met Asp Arg Asn Leu Ile Gln Val Lys Asp Gly Ser Glu
                565                 570                 575

Thr Asn Ser Ala Pro Ser Lys Gly Lys Gly Ser Asp Ser Arg Lys Arg
            580                 585                 590

Arg Asn Leu Lys Ile Lys
            595

<210> SEQ ID NO 31
<211> LENGTH: 598
<212> TYPE: PRT
<213> ORGANISM: Arabidopsis thaliana
<220> FEATURE:
<221> NAME/KEY: SITE
<222> LOCATION: 537..573
<223> OTHER INFORMATION: Xaa can be any naturally occuring amino acid

<400> SEQUENCE: 31

Met Thr Glu Pro Asn Leu Asp Glu Asp Gly Ser Lys Ser Ser Phe Gln
1               5                   10                  15

Lys Thr Val Val Leu Arg Asp Trp Trp Leu Ile Lys Cys Pro Lys Glu
                20                  25                  30

Phe Glu Gly Lys Gln Phe Gly Val Ala Gly Phe Glu Glu Ser Val Glu
            35                  40                  45

Thr Arg Ala Met Arg Val Phe Thr Ser Ser Pro Ile Thr Lys Ala Leu
    50                  55                  60

Asp Val Phe Thr Leu Leu Ala Ser Asp Gly Ile Tyr Ile Thr Leu Arg
65                  70                  75                  80

Gly Phe Leu Asn Lys Glu Arg Val Leu Lys Asn Gly Phe Asn Pro Glu
                85                  90                  95

Ile Ser Arg Glu Phe Ile Phe Gly Phe Pro Pro Cys Trp Glu Arg Val
            100                 105                 110

Cys Asn Ser Cys Phe Glu Gly Asp Ser Phe Gly Thr Asp Val Asn Thr
    115                 120                 125

Val Pro Ser Thr Ile Glu Lys Ala Cys Pro Ile Leu Ser Pro Cys
130                 135                 140

Lys Tyr Ser Asn Arg Asn Leu Lys Asp Asn Pro Ala Glu Ser Arg Glu
145                 150                 155                 160

Lys Ser Asn Val Thr Glu Thr Asp Ile Ala Glu Ile Asn Asp Lys Gly
                165                 170                 175

Gly Ser Gly Ala Arg Asp Ile Lys Thr Ala Arg Arg Ser Leu His
            180                 185                 190
```

```
Leu Gln Ile Lys Arg Ile Leu Glu Ser Ser Lys Val Arg Lys Thr Ala
        195                 200                 205
Asn Asp Gly Asp His Gly Ser Glu Phe Leu Asn Thr Ala Lys Arg Gly
210                 215                 220
Asp Val Glu Arg Asp Gly Cys Glu Val Ile Asn Asn Glu Asp Ser Glu
225                 230                 235                 240
Trp Lys Leu Asp Glu Ser Glu Val Gln Asn Leu Cys Asn Asp Gly Asp
                245                 250                 255
Asn Gly Ser Glu Gly Phe Ile Lys Ala Lys Ser Ser Asp Val Glu Lys
            260                 265                 270
Asp Lys Ser Glu Ala Ile Asp Asn Asp Val Ile Ser Pro Ala Val Gly
        275                 280                 285
Ser Gly Ile Lys His Thr Gly Ala Asp Asn Val Asp Lys Val Thr Ser
    290                 295                 300
Ala Ser Ala Thr Gly Glu Ser Leu Thr Ser Glu Gln Gln Asn Gly Leu
305                 310                 315                 320
Leu Val Thr Thr Ala Ser Pro His Ser Leu Lys Asp Leu Ala Lys
                325                 330                 335
Ser Ser Lys Pro Glu Lys Lys Gly Ile Ser Lys Ser Gly Lys Ile
                340                 345                 350
Leu Arg Ser Asp Asp Asn Val Val Asp Pro Met Asn Tyr Ser Gly Thr
                355                 360                 365
Lys Val Lys Ser Ala Glu Asn Lys Arg Lys Ile Asp Ala Ser Lys Leu
            370                 375                 380
Gln Ser Pro Thr Ser Asn Val Ala Glu His Ser Lys Glu Gly Leu Asn
385                 390                 395                 400
Asn Ala Lys Ser Asn Asp Val Glu Lys Asp Val Cys Val Ala Ile Asn
                405                 410                 415
Asn Glu Val Ile Ser Pro Val Lys Gly Phe Gly Lys Arg Leu Ser Gly
            420                 425                 430
Thr Asp Val Glu Arg Leu Thr Ser Lys Asn Ala Thr Lys Glu Ser Leu
        435                 440                 445
Thr Ser Val Gln Arg Lys Gly Arg Val Lys Val Ser Lys Ala Phe Gln
450                 455                 460
Asp Pro Leu Ser Lys Gly Lys Ser Lys Ser Glu Lys Thr Leu Gln
465                 470                 475                 480
Ser Asn Ser Asn Val Val Glu Pro Met Asn His Phe Arg Ser Glu Ala
                485                 490                 495
Glu Glu Ala Glu Glu Asn Leu Ser Trp Glu Lys Ile Lys Arg Lys Ile
                500                 505                 510
Asp Phe Asp Val Glu Val Thr Pro Glu Lys Lys Val Lys Gln Gln Lys
        515                 520                 525
Thr Asn Ala Ala Ser Thr Asp Ser Xaa Xaa Xaa Xaa Xaa Xaa Xaa
530                 535                 540
Xaa Xaa Xaa Xaa Xaa Xaa Xaa Xaa Xaa Xaa Xaa Xaa Xaa Xaa Xaa
545                 550                 555                 560
Xaa Xaa Xaa Xaa Xaa Xaa Xaa Xaa Xaa Xaa Xaa Xaa Xaa Gly Ser Glu
                565                 570                 575
Thr Asn Ser Ala Pro Ser Lys Gly Lys Gly Ser Asp Ser Arg Lys Arg
            580                 585                 590
Arg Asn Leu Lys Ile Lys
        595
```

-continued

```
<210> SEQ ID NO 32
<211> LENGTH: 37
<212> TYPE: PRT
<213> ORGANISM: Arabidopsis thaliana
<220> FEATURE:
<221> NAME/KEY: SITE
<222> LOCATION: 10
<223> OTHER INFORMATION: Xaa can be any naturally occuring amino acid

<400> SEQUENCE: 32

Leu Gly Gln Lys Arg Ser Arg Ser Gly Xaa Val Leu Val Ser Ser Leu
1               5                   10                  15

Glu Phe Trp Arg Asn Gln Ile Pro Val Tyr Asp Met Asp Arg Asn Leu
            20                  25                  30

Ile Gln Val Lys Asp
        35

<210> SEQ ID NO 33
<211> LENGTH: 37
<212> TYPE: PRT
<213> ORGANISM: Arabidopsis lyrata
<220> FEATURE:
<221> NAME/KEY: SITE
<222> LOCATION: 10
<223> OTHER INFORMATION: Xaa can be any naturally occuring amino acid

<400> SEQUENCE: 33

Val Gly Gln Lys Arg Ser Arg Ser Gly Xaa Val Leu Val Ser Ser Leu
1               5                   10                  15

Glu Phe Trp Arg Asn Gln Ile Pro Val Tyr Asp Met Asp Arg Asn Leu
            20                  25                  30

Ile Gln Val Lys Asp
        35

<210> SEQ ID NO 34
<211> LENGTH: 37
<212> TYPE: PRT
<213> ORGANISM: Capsella
<220> FEATURE:
<221> NAME/KEY: SITE
<222> LOCATION: 10
<223> OTHER INFORMATION: Xaa can be any naturally occuring amino acid

<400> SEQUENCE: 34

Leu Gly Gln Lys Arg Ser Arg Ser Gly Xaa Val Leu Val Ser Pro Leu
1               5                   10                  15

Glu Phe Trp Arg Asn Gln Ile Pro Val Tyr Asp Met Asp Arg Asn Leu
            20                  25                  30

Ile Gln Val Lys Asp
        35

<210> SEQ ID NO 35
<211> LENGTH: 37
<212> TYPE: PRT
<213> ORGANISM: Glycine
<220> FEATURE:
<221> NAME/KEY: SITE
<222> LOCATION: 10
<223> OTHER INFORMATION: Xaa can be any naturally occuring amino acid

<400> SEQUENCE: 35

Pro Ser Phe Arg Lys Ser Arg Ser Gly Xaa Leu Leu Leu Pro Pro Leu
1               5                   10                  15

Glu Phe Trp Arg Asn Gln Ile Pro Ile Tyr Asn Ala Asp His Glu Ile
            20                  25                  30
```

Thr Glu Ile Gln Asp
        35

<210> SEQ ID NO 36
<211> LENGTH: 37
<212> TYPE: PRT
<213> ORGANISM: Glycine
<220> FEATURE:
<223> OTHER INFORMATION: alternative Sequence of Glycine
<220> FEATURE:
<221> NAME/KEY: SITE
<222> LOCATION: 10
<223> OTHER INFORMATION: Xaa can be any naturally occuring amino acid

<400> SEQUENCE: 36

Leu Ser Phe Arg Lys Ser Arg Ser Gly Xaa Leu Leu Leu Pro Pro Leu
1               5                   10                  15

Glu Phe Trp Arg Asn Gln Ile Pro Ile Tyr Asn Ala Asp His Glu Ile
            20                  25                  30

Thr Glu Ile Arg Asp
        35

<210> SEQ ID NO 37
<211> LENGTH: 37
<212> TYPE: PRT
<213> ORGANISM: Phaseolus
<220> FEATURE:
<221> NAME/KEY: SITE
<222> LOCATION: 10
<223> OTHER INFORMATION: Xaa can be any naturally occuring amino acid

<400> SEQUENCE: 37

Ser Asn Phe Arg Thr Ser Arg Ser Gly Xaa Met Leu Leu Pro Pro Leu
1               5                   10                  15

Glu Phe Trp Arg Asn Gln Ile Pro Ile Tyr Asp Ala Asp His Glu Leu
            20                  25                  30

Lys Glu Ile Lys Asp
        35

<210> SEQ ID NO 38
<211> LENGTH: 37
<212> TYPE: PRT
<213> ORGANISM: Medicago
<220> FEATURE:
<221> NAME/KEY: SITE
<222> LOCATION: 10
<223> OTHER INFORMATION: Xaa can be any naturally occuring amino acid

<400> SEQUENCE: 38

Leu Gly Leu Lys Lys Ser Arg Ser Gly Xaa Trp Leu Leu Pro Arg Leu
1               5                   10                  15

Glu Phe Trp Arg Asn Gln Thr Pro Ile Tyr Asn Met Asp Arg Glu Ile
            20                  25                  30

Ile Glu Ile Gln Glu
        35

<210> SEQ ID NO 39
<211> LENGTH: 37
<212> TYPE: PRT
<213> ORGANISM: Medicago
<220> FEATURE:
<221> NAME/KEY: SITE
<222> LOCATION: 10
<223> OTHER INFORMATION: Xaa can be any naturally occuring amino acid

```
<400> SEQUENCE: 39

Leu Ser Leu Lys Lys Ser Arg Ser Gly Xaa Trp Leu Leu Pro Pro Leu
1               5                   10                  15

Glu Phe Trp Arg Asn Gln Gln Pro Ile Tyr Asn Met Asp Arg Glu Ile
            20                  25                  30

Thr Glu Ile Gln Glu
            35

<210> SEQ ID NO 40
<211> LENGTH: 37
<212> TYPE: PRT
<213> ORGANISM: Cicer
<220> FEATURE:
<221> NAME/KEY: SITE
<222> LOCATION: 10
<223> OTHER INFORMATION: Xaa can be any naturally occuring amino acid

<400> SEQUENCE: 40

Leu Ser Leu Lys Lys Ser Arg Ser Gly Xaa Leu Leu Leu Pro Pro Leu
1               5                   10                  15

Glu Phe Trp His Asn Gln Lys Pro Ile Tyr Asn Val Asp Arg Glu Ile
            20                  25                  30

Thr Glu Ile Gln Ala
            35

<210> SEQ ID NO 41
<211> LENGTH: 37
<212> TYPE: PRT
<213> ORGANISM: Citrus sinensis
<220> FEATURE:
<221> NAME/KEY: SITE
<222> LOCATION: 10
<223> OTHER INFORMATION: Xaa can be any naturally occuring amino acid

<400> SEQUENCE: 41

Leu Ser Leu Lys Arg Ser Arg Ser Gly Xaa Leu Leu Val Pro Cys Leu
1               5                   10                  15

Asp Phe Trp Arg Asn Gln Ile Ala Val Tyr Asp Ala Asp Arg Asn Ile
            20                  25                  30

Thr Gly Ile Gln Glu
            35

<210> SEQ ID NO 42
<211> LENGTH: 37
<212> TYPE: PRT
<213> ORGANISM: Vitis
<220> FEATURE:
<221> NAME/KEY: SITE
<222> LOCATION: 10
<223> OTHER INFORMATION: Xaa can be any naturally occuring amino acid

<400> SEQUENCE: 42

Leu Ser Leu Lys Arg Ser Arg Ser Gly Xaa Leu Leu Leu Pro Ser Leu
1               5                   10                  15

Asp Phe Trp Arg Asn Gln Lys Ala Val Tyr Asp Ala Asp Arg Arg Ile
            20                  25                  30

Thr Gly Ile Gln Glu
            35

<210> SEQ ID NO 43
<211> LENGTH: 37
<212> TYPE: PRT
<213> ORGANISM: Theobroma
```

```
<220> FEATURE:
<221> NAME/KEY: SITE
<222> LOCATION: 10
<223> OTHER INFORMATION: Xaa can be any naturally occuring amino acid

<400> SEQUENCE: 43

Leu Ser Leu Lys Cys Ser Arg Ser Gly Xaa Leu Leu Leu Pro Arg Leu
1               5                   10                  15

Glu Phe Trp Arg Asn Gln Ile Ala Val Tyr Asp Gln Thr Arg Lys Ile
            20                  25                  30

Thr Gly Ile Arg Glu
        35

<210> SEQ ID NO 44
<211> LENGTH: 37
<212> TYPE: PRT
<213> ORGANISM: Solanum
<220> FEATURE:
<221> NAME/KEY: SITE
<222> LOCATION: 10
<223> OTHER INFORMATION: Xaa can be any naturally occuring amino acid

<400> SEQUENCE: 44

Leu Ser Phe Asn Arg Ser Arg Ser Gly Xaa Val Leu Leu Pro Pro Met
1               5                   10                  15

Ala Phe Trp Arg Asn Gln Arg Ala Val Tyr Asp Val Ile Leu Phe Thr
            20                  25                  30

Thr Gly Ile Ser Cys
        35

<210> SEQ ID NO 45
<211> LENGTH: 37
<212> TYPE: PRT
<213> ORGANISM: Populus
<220> FEATURE:
<221> NAME/KEY: SITE
<222> LOCATION: 10
<223> OTHER INFORMATION: Xaa can be any naturally occuring amino acid

<400> SEQUENCE: 45

Leu Asn Leu Lys Arg Ser Arg Ser Gly Xaa Leu Leu Leu Pro Thr Leu
1               5                   10                  15

Asp Phe Trp Arg Asn Gln Ile Pro Val Tyr Asp Glu Val Ser Gly Ile
            20                  25                  30

Ser Gly Ile Phe Pro
        35

<210> SEQ ID NO 46
<211> LENGTH: 37
<212> TYPE: PRT
<213> ORGANISM: Fragaria
<220> FEATURE:
<221> NAME/KEY: SITE
<222> LOCATION: 10
<223> OTHER INFORMATION: Xaa can be any naturally occuring amino acid

<400> SEQUENCE: 46

Leu Ser Thr Gly Arg Ser Arg Ser Gly Xaa Leu Leu Leu Arg Pro Leu
1               5                   10                  15

Glu Phe Trp Arg Asn Gln Ser Pro Val Tyr Asp Lys Asp His Gly Val
            20                  25                  30

Ile Gly Ile Gln Glu
        35
```

```
<210> SEQ ID NO 47
<211> LENGTH: 37
<212> TYPE: PRT
<213> ORGANISM: Fragaria
<220> FEATURE:
<221> NAME/KEY: SITE
<222> LOCATION: 10
<223> OTHER INFORMATION: Xaa can be any naturally occuring amino acid

<400> SEQUENCE: 47

Leu Ser Ala Gly Arg Ser Arg Ser Gly Xaa Leu Arg Leu Arg Pro Leu
1               5                   10                  15

Glu Phe Trp Arg Asn Gln Ser Ala Val Tyr Asp Lys Asp His Gly Val
            20                  25                  30

Ile Gly Ile Gln Glu
        35

<210> SEQ ID NO 48
<211> LENGTH: 37
<212> TYPE: PRT
<213> ORGANISM: Amborella
<220> FEATURE:
<221> NAME/KEY: SITE
<222> LOCATION: 10
<223> OTHER INFORMATION: Xaa can be any naturally occuring amino acid

<400> SEQUENCE: 48

Phe Leu Leu Ser Ile Ser Arg Ser Gly Xaa Ile Ile Val Arg Pro Leu
1               5                   10                  15

Ala Tyr Trp Cys Asn Glu Arg Ile Val Tyr Gly Lys Asp Gly Ser Ile
            20                  25                  30

Thr Ser Ile Leu Asp
        35

<210> SEQ ID NO 49
<211> LENGTH: 37
<212> TYPE: PRT
<213> ORGANISM: Physcomitrella
<220> FEATURE:
<221> NAME/KEY: SITE
<222> LOCATION: 10
<223> OTHER INFORMATION: Xaa can be any naturally occuring amino acid

<400> SEQUENCE: 49

Phe Gly Leu Lys Thr Ser Arg Ser Gly Xaa Leu Leu Val Pro Ala Leu
1               5                   10                  15

Ala Tyr Trp Arg Ser Gln Ser Ile Glu Tyr Asp Lys Asp Gly Gly Ile
            20                  25                  30

Ile Ala Ile Phe Asp
        35

<210> SEQ ID NO 50
<211> LENGTH: 37
<212> TYPE: PRT
<213> ORGANISM: Oryza
<220> FEATURE:
<221> NAME/KEY: SITE
<222> LOCATION: 10
<223> OTHER INFORMATION: Xaa can be any naturally occuring amino acid

<400> SEQUENCE: 50

Leu Lys Leu Arg Arg Thr Arg Ser Gly Xaa Val Val Val Pro Thr Leu
1               5                   10                  15

Asp Pro Gly Cys Gln Arg Ile Val Tyr Asp Arg Asp Gly Leu Val Ser
```

-continued

```
                 20                  25                  30

Gly Val Ala Gly Leu
            35

<210> SEQ ID NO 51
<211> LENGTH: 37
<212> TYPE: PRT
<213> ORGANISM: Arabidopsis thaliana

<400> SEQUENCE: 51

Leu Gly Gln Lys Arg Ser Arg Ser Gly Ala Val Leu Val Ser Ser Leu
1               5                   10                  15

Glu Phe Trp Arg Asn Gln Ile Pro Val Tyr Asp Met Asp Arg Asn Leu
                20                  25                  30

Ile Gln Val Lys Asp
            35

<210> SEQ ID NO 52
<211> LENGTH: 37
<212> TYPE: PRT
<213> ORGANISM: Arabidopsis lyrata

<400> SEQUENCE: 52

Val Gly Gln Lys Arg Ser Arg Ser Gly Ala Val Leu Val Ser Ser Leu
1               5                   10                  15

Glu Phe Trp Arg Asn Gln Ile Pro Val Tyr Asp Met Asp Arg Asn Leu
                20                  25                  30

Ile Gln Val Lys Asp
            35

<210> SEQ ID NO 53
<211> LENGTH: 37
<212> TYPE: PRT
<213> ORGANISM: Capsella

<400> SEQUENCE: 53

Leu Gly Gln Lys Arg Ser Arg Ser Gly Ala Val Leu Val Ser Pro Leu
1               5                   10                  15

Glu Phe Trp Arg Asn Gln Ile Pro Val Tyr Asp Met Asp Arg Asn Leu
                20                  25                  30

Ile Gln Val Lys Asp
            35

<210> SEQ ID NO 54
<211> LENGTH: 37
<212> TYPE: PRT
<213> ORGANISM: Glycine

<400> SEQUENCE: 54

Pro Ser Phe Arg Lys Ser Arg Ser Gly Ala Leu Leu Leu Pro Pro Leu
1               5                   10                  15

Glu Phe Trp Arg Asn Gln Ile Pro Ile Tyr Asn Ala Asp His Glu Ile
                20                  25                  30

Thr Glu Ile Gln Asp
            35

<210> SEQ ID NO 55
<211> LENGTH: 37
<212> TYPE: PRT
<213> ORGANISM: Glycine
<220> FEATURE:
```

<223> OTHER INFORMATION: alternative Sequence of Glycine

<400> SEQUENCE: 55

Leu Ser Phe Arg Lys Ser Arg Ser Gly Ala Leu Leu Pro Pro Leu
1               5                   10                  15

Glu Phe Trp Arg Asn Gln Ile Pro Ile Tyr Asn Ala Asp His Glu Ile
            20                  25                  30

Thr Glu Ile Arg Asp
        35

<210> SEQ ID NO 56
<211> LENGTH: 37
<212> TYPE: PRT
<213> ORGANISM: Phaseolus

<400> SEQUENCE: 56

Ser Asn Phe Arg Thr Ser Arg Ser Gly Ala Met Leu Leu Pro Pro Leu
1               5                   10                  15

Glu Phe Trp Arg Asn Gln Ile Pro Ile Tyr Asp Ala Asp His Glu Leu
            20                  25                  30

Lys Glu Ile Lys Asp
        35

<210> SEQ ID NO 57
<211> LENGTH: 37
<212> TYPE: PRT
<213> ORGANISM: Medicago

<400> SEQUENCE: 57

Leu Gly Leu Lys Lys Ser Arg Ser Gly Ala Trp Leu Leu Pro Arg Leu
1               5                   10                  15

Glu Phe Trp Arg Asn Gln Thr Pro Ile Tyr Asn Met Asp Arg Glu Ile
            20                  25                  30

Ile Glu Ile Gln Glu
        35

<210> SEQ ID NO 58
<211> LENGTH: 37
<212> TYPE: PRT
<213> ORGANISM: Medicago

<400> SEQUENCE: 58

Leu Ser Leu Lys Lys Ser Arg Ser Gly Ala Trp Leu Leu Pro Pro Leu
1               5                   10                  15

Glu Phe Trp Arg Asn Gln Gln Pro Ile Tyr Asn Met Asp Arg Glu Ile
            20                  25                  30

Thr Glu Ile Gln Glu
        35

<210> SEQ ID NO 59
<211> LENGTH: 37
<212> TYPE: PRT
<213> ORGANISM: Cicer

<400> SEQUENCE: 59

Leu Ser Leu Lys Lys Ser Arg Ser Gly Ala Leu Leu Leu Pro Pro Leu
1               5                   10                  15

Glu Phe Trp His Asn Gln Lys Pro Ile Tyr Asn Val Asp Arg Glu Ile
            20                  25                  30

Thr Glu Ile Gln Ala

```
                35

<210> SEQ ID NO 60
<211> LENGTH: 37
<212> TYPE: PRT
<213> ORGANISM: Citrus sinensis

<400> SEQUENCE: 60

Leu Ser Leu Lys Arg Ser Arg Ser Gly Ala Leu Leu Val Pro Cys Leu
1               5                   10                  15

Asp Phe Trp Arg Asn Gln Ile Ala Val Tyr Asp Ala Asp Arg Asn Ile
                20                  25                  30

Thr Gly Ile Gln Glu
        35

<210> SEQ ID NO 61
<211> LENGTH: 37
<212> TYPE: PRT
<213> ORGANISM: Vitis

<400> SEQUENCE: 61

Leu Ser Leu Lys Arg Ser Arg Ser Gly Ala Leu Leu Leu Pro Ser Leu
1               5                   10                  15

Asp Phe Trp Arg Asn Gln Lys Ala Val Tyr Asp Ala Asp Arg Arg Ile
                20                  25                  30

Thr Gly Ile Gln Glu
        35

<210> SEQ ID NO 62
<211> LENGTH: 37
<212> TYPE: PRT
<213> ORGANISM: Theobroma

<400> SEQUENCE: 62

Leu Ser Leu Lys Cys Ser Arg Ser Gly Ala Leu Leu Leu Pro Arg Leu
1               5                   10                  15

Glu Phe Trp Arg Asn Gln Ile Ala Val Tyr Asp Gln Thr Arg Lys Ile
                20                  25                  30

Thr Gly Ile Arg Glu
        35

<210> SEQ ID NO 63
<211> LENGTH: 37
<212> TYPE: PRT
<213> ORGANISM: Solanum

<400> SEQUENCE: 63

Leu Ser Phe Asn Arg Ser Arg Ser Gly Ala Val Leu Leu Pro Pro Met
1               5                   10                  15

Ala Phe Trp Arg Asn Gln Arg Ala Val Tyr Asp Val Ile Leu Phe Thr
                20                  25                  30

Thr Gly Ile Ser Cys
        35

<210> SEQ ID NO 64
<211> LENGTH: 37
<212> TYPE: PRT
<213> ORGANISM: Populus

<400> SEQUENCE: 64

Leu Asn Leu Lys Arg Ser Arg Ser Gly Ala Leu Leu Leu Pro Thr Leu
```

1               5                   10                  15
Asp Phe Trp Arg Asn Gln Ile Pro Val Tyr Asp Glu Val Ser Gly Ile
                20                  25                  30

Ser Gly Ile Phe Pro
            35

<210> SEQ ID NO 65
<211> LENGTH: 37
<212> TYPE: PRT
<213> ORGANISM: Fragaria

<400> SEQUENCE: 65

Leu Ser Thr Gly Arg Ser Arg Ser Gly Ala Leu Leu Leu Arg Pro Leu
1               5                   10                  15

Glu Phe Trp Arg Asn Gln Ser Pro Val Tyr Asp Lys Asp His Gly Val
                20                  25                  30

Ile Gly Ile Gln Glu
            35

<210> SEQ ID NO 66
<211> LENGTH: 37
<212> TYPE: PRT
<213> ORGANISM: Fragaria

<400> SEQUENCE: 66

Leu Ser Ala Gly Arg Ser Arg Ser Gly Ala Leu Arg Leu Arg Pro Leu
1               5                   10                  15

Glu Phe Trp Arg Asn Gln Ser Ala Val Tyr Asp Lys Asp His Gly Val
                20                  25                  30

Ile Gly Ile Gln Glu
            35

<210> SEQ ID NO 67
<211> LENGTH: 37
<212> TYPE: PRT
<213> ORGANISM: Amborella

<400> SEQUENCE: 67

Phe Leu Leu Ser Ile Ser Arg Ser Gly Ala Ile Ile Val Arg Pro Leu
1               5                   10                  15

Ala Tyr Trp Cys Asn Glu Arg Ile Val Tyr Gly Lys Asp Gly Ser Ile
                20                  25                  30

Thr Ser Ile Leu Asp
            35

<210> SEQ ID NO 68
<211> LENGTH: 37
<212> TYPE: PRT
<213> ORGANISM: Physcomitrella

<400> SEQUENCE: 68

Phe Gly Leu Lys Thr Ser Arg Ser Gly Ala Leu Leu Val Pro Ala Leu
1               5                   10                  15

Ala Tyr Trp Arg Ser Gln Ser Ile Glu Tyr Asp Lys Asp Gly Gly Ile
                20                  25                  30

Ile Ala Ile Phe Asp
            35

<210> SEQ ID NO 69
<211> LENGTH: 37

```
<212> TYPE: PRT
<213> ORGANISM: Oryza

<400> SEQUENCE: 69

Leu Lys Leu Arg Arg Thr Arg Ser Gly Ala Val Val Pro Thr Leu
1               5                   10                  15

Asp Pro Gly Cys Gln Arg Ile Val Tyr Asp Arg Asp Gly Leu Val Ser
            20                  25                  30

Gly Val Ala Gly Leu
        35

<210> SEQ ID NO 70
<211> LENGTH: 37
<212> TYPE: PRT
<213> ORGANISM: Arabidopsis thaliana
<220> FEATURE:
<221> NAME/KEY: SITE
<222> LOCATION: 19
<223> OTHER INFORMATION: Xaa can be any naturally occuring amino acid

<400> SEQUENCE: 70

Leu Gly Gln Lys Arg Ser Arg Ser Gly Arg Val Leu Val Ser Ser Leu
1               5                   10                  15

Glu Phe Xaa Arg Asn Gln Ile Pro Val Tyr Asp Met Asp Arg Asn Leu
            20                  25                  30

Ile Gln Val Lys Asp
        35

<210> SEQ ID NO 71
<211> LENGTH: 37
<212> TYPE: PRT
<213> ORGANISM: Arabidopsis lyrata
<220> FEATURE:
<221> NAME/KEY: SITE
<222> LOCATION: 19
<223> OTHER INFORMATION: Xaa can be any naturally occuring amino acid

<400> SEQUENCE: 71

Val Gly Gln Lys Arg Ser Arg Ser Gly Arg Val Leu Val Ser Ser Leu
1               5                   10                  15

Glu Phe Xaa Arg Asn Gln Ile Pro Val Tyr Asp Met Asp Arg Asn Leu
            20                  25                  30

Ile Gln Val Lys Asp
        35

<210> SEQ ID NO 72
<211> LENGTH: 37
<212> TYPE: PRT
<213> ORGANISM: Capsella
<220> FEATURE:
<221> NAME/KEY: SITE
<222> LOCATION: 19
<223> OTHER INFORMATION: Xaa can be any naturally occuring amino acid

<400> SEQUENCE: 72

Leu Gly Gln Lys Arg Ser Arg Ser Gly Arg Val Leu Val Ser Pro Leu
1               5                   10                  15

Glu Phe Xaa Arg Asn Gln Ile Pro Val Tyr Asp Met Asp Arg Asn Leu
            20                  25                  30

Ile Gln Val Lys Asp
        35

<210> SEQ ID NO 73
```

```
<211> LENGTH: 37
<212> TYPE: PRT
<213> ORGANISM: Glycine
<220> FEATURE:
<221> NAME/KEY: SITE
<222> LOCATION: 19
<223> OTHER INFORMATION: Xaa can be any naturally occuring amino acid

<400> SEQUENCE: 73

Pro Ser Phe Arg Lys Ser Arg Ser Gly Arg Leu Leu Leu Pro Pro Leu
1               5                   10                  15

Glu Phe Xaa Arg Asn Gln Ile Pro Ile Tyr Asn Ala Asp His Glu Ile
            20                  25                  30

Thr Glu Ile Gln Asp
        35

<210> SEQ ID NO 74
<211> LENGTH: 37
<212> TYPE: PRT
<213> ORGANISM: Glycine
<220> FEATURE:
<223> OTHER INFORMATION: alternative Sequence of Glycine
<220> FEATURE:
<221> NAME/KEY: SITE
<222> LOCATION: 19
<223> OTHER INFORMATION: Xaa can be any naturally occuring amino acid

<400> SEQUENCE: 74

Leu Ser Phe Arg Lys Ser Arg Ser Gly Arg Leu Leu Leu Pro Pro Leu
1               5                   10                  15

Glu Phe Xaa Arg Asn Gln Ile Pro Ile Tyr Asn Ala Asp His Glu Ile
            20                  25                  30

Thr Glu Ile Arg Asp
        35

<210> SEQ ID NO 75
<211> LENGTH: 37
<212> TYPE: PRT
<213> ORGANISM: Phaseolus
<220> FEATURE:
<221> NAME/KEY: SITE
<222> LOCATION: 19
<223> OTHER INFORMATION: Xaa can be any naturally occuring amino acid

<400> SEQUENCE: 75

Ser Asn Phe Arg Thr Ser Arg Ser Gly Arg Met Leu Leu Pro Pro Leu
1               5                   10                  15

Glu Phe Xaa Arg Asn Gln Ile Pro Ile Tyr Asp Ala Asp His Glu Leu
            20                  25                  30

Lys Glu Ile Lys Asp
        35

<210> SEQ ID NO 76
<211> LENGTH: 37
<212> TYPE: PRT
<213> ORGANISM: Medicago
<220> FEATURE:
<221> NAME/KEY: SITE
<222> LOCATION: 19
<223> OTHER INFORMATION: Xaa can be any naturally occuring amino acid

<400> SEQUENCE: 76

Leu Gly Leu Lys Lys Ser Arg Ser Gly Arg Trp Leu Leu Pro Arg Leu
1               5                   10                  15

Glu Phe Xaa Arg Asn Gln Thr Pro Ile Tyr Asn Met Asp Arg Glu Ile
```

Ile Glu Ile Gln Glu
              35

<210> SEQ ID NO 77
<211> LENGTH: 37
<212> TYPE: PRT
<213> ORGANISM: Medicago
<220> FEATURE:
<221> NAME/KEY: SITE
<222> LOCATION: 19
<223> OTHER INFORMATION: Xaa can be any naturally occuring amino acid

<400> SEQUENCE: 77

Leu Ser Leu Lys Lys Ser Arg Ser Gly Arg Trp Leu Leu Pro Pro Leu
1               5                   10                  15

Glu Phe Xaa Arg Asn Gln Gln Pro Ile Tyr Asn Met Asp Arg Glu Ile
            20                  25                  30

Thr Glu Ile Gln Glu
              35

<210> SEQ ID NO 78
<211> LENGTH: 37
<212> TYPE: PRT
<213> ORGANISM: Cicer
<220> FEATURE:
<221> NAME/KEY: SITE
<222> LOCATION: 19
<223> OTHER INFORMATION: Xaa can be any naturally occuring amino acid

<400> SEQUENCE: 78

Leu Ser Leu Lys Lys Ser Arg Ser Gly Arg Leu Leu Leu Pro Pro Leu
1               5                   10                  15

Glu Phe Xaa His Asn Gln Lys Pro Ile Tyr Asn Val Asp Arg Glu Ile
            20                  25                  30

Thr Glu Ile Gln Ala
              35

<210> SEQ ID NO 79
<211> LENGTH: 37
<212> TYPE: PRT
<213> ORGANISM: Citrus sinensis
<220> FEATURE:
<221> NAME/KEY: SITE
<222> LOCATION: 19
<223> OTHER INFORMATION: Xaa can be any naturally occuring amino acid

<400> SEQUENCE: 79

Leu Ser Leu Lys Arg Ser Arg Ser Gly Arg Leu Leu Val Pro Cys Leu
1               5                   10                  15

Asp Phe Xaa Arg Asn Gln Ile Ala Val Tyr Asp Ala Asp Arg Asn Ile
            20                  25                  30

Thr Gly Ile Gln Glu
              35

<210> SEQ ID NO 80
<211> LENGTH: 37
<212> TYPE: PRT
<213> ORGANISM: Vitis
<220> FEATURE:
<221> NAME/KEY: SITE
<222> LOCATION: 19
<223> OTHER INFORMATION: Xaa can be any naturally occuring amino acid

<400> SEQUENCE: 80

```
Leu Ser Leu Lys Arg Ser Arg Ser Gly Arg Leu Leu Leu Pro Ser Leu
1               5                   10                  15

Asp Phe Xaa Arg Asn Gln Lys Ala Val Tyr Asp Ala Asp Arg Arg Ile
            20                  25                  30

Thr Gly Ile Gln Glu
        35

<210> SEQ ID NO 81
<211> LENGTH: 37
<212> TYPE: PRT
<213> ORGANISM: Theobroma
<220> FEATURE:
<221> NAME/KEY: SITE
<222> LOCATION: 19
<223> OTHER INFORMATION: Xaa can be any naturally occuring amino acid

<400> SEQUENCE: 81

Leu Ser Leu Lys Cys Ser Arg Ser Gly Arg Leu Leu Leu Pro Arg Leu
1               5                   10                  15

Glu Phe Xaa Arg Asn Gln Ile Ala Val Tyr Asp Gln Thr Arg Lys Ile
            20                  25                  30

Thr Gly Ile Arg Glu
        35

<210> SEQ ID NO 82
<211> LENGTH: 37
<212> TYPE: PRT
<213> ORGANISM: Solanum
<220> FEATURE:
<221> NAME/KEY: SITE
<222> LOCATION: 19
<223> OTHER INFORMATION: Xaa can be any naturally occuring amino acid

<400> SEQUENCE: 82

Leu Ser Phe Asn Arg Ser Arg Ser Gly Arg Val Leu Leu Pro Pro Met
1               5                   10                  15

Ala Phe Xaa Arg Asn Gln Arg Ala Val Tyr Asp Val Ile Leu Phe Thr
            20                  25                  30

Thr Gly Ile Ser Cys
        35

<210> SEQ ID NO 83
<211> LENGTH: 37
<212> TYPE: PRT
<213> ORGANISM: Populus
<220> FEATURE:
<221> NAME/KEY: SITE
<222> LOCATION: 19
<223> OTHER INFORMATION: Xaa can be any naturally occuring amino acid

<400> SEQUENCE: 83

Leu Asn Leu Lys Arg Ser Arg Ser Gly Arg Leu Leu Leu Pro Thr Leu
1               5                   10                  15

Asp Phe Xaa Arg Asn Gln Ile Pro Val Tyr Asp Glu Val Ser Gly Ile
            20                  25                  30

Ser Gly Ile Phe Pro
        35

<210> SEQ ID NO 84
<211> LENGTH: 37
<212> TYPE: PRT
<213> ORGANISM: Fragaria
<220> FEATURE:
```

```
<221> NAME/KEY: SITE
<222> LOCATION: 19
<223> OTHER INFORMATION: Xaa can be any naturally occuring amino acid

<400> SEQUENCE: 84

Leu Ser Thr Gly Arg Ser Arg Ser Gly Arg Leu Leu Leu Arg Pro Leu
1               5                   10                  15

Glu Phe Xaa Arg Asn Gln Ser Pro Val Tyr Asp Lys Asp His Gly Val
            20                  25                  30

Ile Gly Ile Gln Glu
        35

<210> SEQ ID NO 85
<211> LENGTH: 37
<212> TYPE: PRT
<213> ORGANISM: Fragaria
<220> FEATURE:
<221> NAME/KEY: SITE
<222> LOCATION: 19
<223> OTHER INFORMATION: Xaa can be any naturally occuring amino acid

<400> SEQUENCE: 85

Leu Ser Ala Gly Arg Ser Arg Ser Gly Arg Leu Arg Leu Arg Pro Leu
1               5                   10                  15

Glu Phe Xaa Arg Asn Gln Ser Ala Val Tyr Asp Lys Asp His Gly Val
            20                  25                  30

Ile Gly Ile Gln Glu
        35

<210> SEQ ID NO 86
<211> LENGTH: 37
<212> TYPE: PRT
<213> ORGANISM: Amborella
<220> FEATURE:
<221> NAME/KEY: SITE
<222> LOCATION: 19
<223> OTHER INFORMATION: Xaa can be any naturally occuring amino acid

<400> SEQUENCE: 86

Phe Leu Leu Ser Ile Ser Arg Ser Gly Arg Ile Ile Val Arg Pro Leu
1               5                   10                  15

Ala Tyr Xaa Cys Asn Glu Arg Ile Val Tyr Gly Lys Asp Gly Ser Ile
            20                  25                  30

Thr Ser Ile Leu Asp
        35

<210> SEQ ID NO 87
<211> LENGTH: 37
<212> TYPE: PRT
<213> ORGANISM: Physcomitrella
<220> FEATURE:
<221> NAME/KEY: SITE
<222> LOCATION: 19
<223> OTHER INFORMATION: Xaa can be any naturally occuring amino acid

<400> SEQUENCE: 87

Phe Gly Leu Lys Thr Ser Arg Ser Gly Arg Leu Leu Val Pro Ala Leu
1               5                   10                  15

Ala Tyr Xaa Arg Ser Gln Ser Ile Glu Tyr Asp Lys Asp Gly Gly Ile
            20                  25                  30

Ile Ala Ile Phe Asp
        35
```

-continued

```
<210> SEQ ID NO 88
<211> LENGTH: 37
<212> TYPE: PRT
<213> ORGANISM: Arabidopsis thaliana

<400> SEQUENCE: 88

Leu Gly Gln Lys Arg Ser Arg Ser Gly Arg Val Leu Val Ser Ser Leu
1               5                   10                  15

Glu Phe Arg Arg Asn Gln Ile Pro Val Tyr Asp Met Asp Arg Asn Leu
            20                  25                  30

Ile Gln Val Lys Asp
        35

<210> SEQ ID NO 89
<211> LENGTH: 37
<212> TYPE: PRT
<213> ORGANISM: Arabidopsis lyrata

<400> SEQUENCE: 89

Val Gly Gln Lys Arg Ser Arg Ser Gly Arg Val Leu Val Ser Ser Leu
1               5                   10                  15

Glu Phe Arg Arg Asn Gln Ile Pro Val Tyr Asp Met Asp Arg Asn Leu
            20                  25                  30

Ile Gln Val Lys Asp
        35

<210> SEQ ID NO 90
<211> LENGTH: 37
<212> TYPE: PRT
<213> ORGANISM: Capsella

<400> SEQUENCE: 90

Leu Gly Gln Lys Arg Ser Arg Ser Gly Arg Val Leu Val Ser Pro Leu
1               5                   10                  15

Glu Phe Arg Arg Asn Gln Ile Pro Val Tyr Asp Met Asp Arg Asn Leu
            20                  25                  30

Ile Gln Val Lys Asp
        35

<210> SEQ ID NO 91
<211> LENGTH: 37
<212> TYPE: PRT
<213> ORGANISM: Glycine

<400> SEQUENCE: 91

Pro Ser Phe Arg Lys Ser Arg Ser Gly Arg Leu Leu Leu Pro Pro Leu
1               5                   10                  15

Glu Phe Arg Arg Asn Gln Ile Pro Ile Tyr Asn Ala Asp His Glu Ile
            20                  25                  30

Thr Glu Ile Gln Asp
        35

<210> SEQ ID NO 92
<211> LENGTH: 37
<212> TYPE: PRT
<213> ORGANISM: Glycine
<220> FEATURE:
<223> OTHER INFORMATION: alternative Sequence of Glycine

<400> SEQUENCE: 92

Leu Ser Phe Arg Lys Ser Arg Ser Gly Arg Leu Leu Leu Pro Pro Leu
1               5                   10                  15
```

Glu Phe Arg Arg Asn Gln Ile Pro Ile Tyr Asn Ala Asp His Glu Ile
            20                  25                  30

Thr Glu Ile Arg Asp
        35

<210> SEQ ID NO 93
<211> LENGTH: 37
<212> TYPE: PRT
<213> ORGANISM: Phaseolus

<400> SEQUENCE: 93

Ser Asn Phe Arg Thr Ser Arg Ser Gly Arg Met Leu Leu Pro Pro Leu
1               5                   10                  15

Glu Phe Arg Arg Asn Gln Ile Pro Ile Tyr Asp Ala Asp His Glu Leu
            20                  25                  30

Lys Glu Ile Lys Asp
        35

<210> SEQ ID NO 94
<211> LENGTH: 37
<212> TYPE: PRT
<213> ORGANISM: Medicago

<400> SEQUENCE: 94

Leu Gly Leu Lys Lys Ser Arg Ser Gly Arg Trp Leu Leu Pro Arg Leu
1               5                   10                  15

Glu Phe Arg Arg Asn Gln Thr Pro Ile Tyr Asn Met Asp Arg Glu Ile
            20                  25                  30

Ile Glu Ile Gln Glu
        35

<210> SEQ ID NO 95
<211> LENGTH: 37
<212> TYPE: PRT
<213> ORGANISM: Medicago

<400> SEQUENCE: 95

Leu Ser Leu Lys Lys Ser Arg Ser Gly Arg Trp Leu Leu Pro Pro Leu
1               5                   10                  15

Glu Phe Arg Arg Asn Gln Gln Pro Ile Tyr Asn Met Asp Arg Glu Ile
            20                  25                  30

Thr Glu Ile Gln Glu
        35

<210> SEQ ID NO 96
<211> LENGTH: 37
<212> TYPE: PRT
<213> ORGANISM: Cicer

<400> SEQUENCE: 96

Leu Ser Leu Lys Lys Ser Arg Ser Gly Arg Leu Leu Leu Pro Pro Leu
1               5                   10                  15

Glu Phe Arg His Asn Gln Lys Pro Ile Tyr Asn Val Asp Arg Glu Ile
            20                  25                  30

Thr Glu Ile Gln Ala
        35

<210> SEQ ID NO 97
<211> LENGTH: 37
<212> TYPE: PRT

<213> ORGANISM: Citrus sinensis

<400> SEQUENCE: 97

Leu Ser Leu Lys Arg Ser Arg Ser Gly Arg Leu Leu Val Pro Cys Leu
1               5                   10                  15
Asp Phe Arg Arg Asn Gln Ile Ala Val Tyr Asp Ala Asp Arg Asn Ile
            20                  25                  30
Thr Gly Ile Gln Glu
        35

<210> SEQ ID NO 98
<211> LENGTH: 37
<212> TYPE: PRT
<213> ORGANISM: Vitis

<400> SEQUENCE: 98

Leu Ser Leu Lys Arg Ser Arg Ser Gly Arg Leu Leu Leu Pro Ser Leu
1               5                   10                  15
Asp Phe Arg Arg Asn Gln Lys Ala Val Tyr Asp Ala Asp Arg Arg Ile
            20                  25                  30
Thr Gly Ile Gln Glu
        35

<210> SEQ ID NO 99
<211> LENGTH: 37
<212> TYPE: PRT
<213> ORGANISM: Theobroma

<400> SEQUENCE: 99

Leu Ser Leu Lys Cys Ser Arg Ser Gly Arg Leu Leu Leu Pro Arg Leu
1               5                   10                  15
Glu Phe Arg Arg Asn Gln Ile Ala Val Tyr Asp Gln Thr Arg Lys Ile
            20                  25                  30
Thr Gly Ile Arg Glu
        35

<210> SEQ ID NO 100
<211> LENGTH: 37
<212> TYPE: PRT
<213> ORGANISM: Solanum

<400> SEQUENCE: 100

Leu Ser Phe Asn Arg Ser Arg Ser Gly Arg Val Leu Leu Pro Pro Met
1               5                   10                  15
Ala Phe Arg Arg Asn Gln Arg Ala Val Tyr Asp Val Ile Leu Phe Thr
            20                  25                  30
Thr Gly Ile Ser Cys
        35

<210> SEQ ID NO 101
<211> LENGTH: 37
<212> TYPE: PRT
<213> ORGANISM: Populus

<400> SEQUENCE: 101

Leu Asn Leu Lys Arg Ser Arg Ser Gly Arg Leu Leu Leu Pro Thr Leu
1               5                   10                  15
Asp Phe Arg Arg Asn Gln Ile Pro Val Tyr Asp Glu Val Ser Gly Ile
            20                  25                  30
Ser Gly Ile Phe Pro

35

<210> SEQ ID NO 102
<211> LENGTH: 37
<212> TYPE: PRT
<213> ORGANISM: Fragaria

<400> SEQUENCE: 102

Leu Ser Thr Gly Arg Ser Arg Ser Gly Arg Leu Leu Leu Arg Pro Leu
1               5                   10                  15

Glu Phe Arg Arg Asn Gln Ser Pro Val Tyr Asp Lys Asp His Gly Val
            20                  25                  30

Ile Gly Ile Gln Glu
            35

<210> SEQ ID NO 103
<211> LENGTH: 37
<212> TYPE: PRT
<213> ORGANISM: Fragaria

<400> SEQUENCE: 103

Leu Ser Ala Gly Arg Ser Arg Ser Gly Arg Leu Arg Leu Arg Pro Leu
1               5                   10                  15

Glu Phe Arg Arg Asn Gln Ser Ala Val Tyr Asp Lys Asp His Gly Val
            20                  25                  30

Ile Gly Ile Gln Glu
            35

<210> SEQ ID NO 104
<211> LENGTH: 37
<212> TYPE: PRT
<213> ORGANISM: Amborella

<400> SEQUENCE: 104

Phe Leu Leu Ser Ile Ser Arg Ser Gly Arg Ile Ile Val Arg Pro Leu
1               5                   10                  15

Ala Tyr Arg Cys Asn Glu Arg Ile Val Tyr Gly Lys Asp Gly Ser Ile
            20                  25                  30

Thr Ser Ile Leu Asp
            35

<210> SEQ ID NO 105
<211> LENGTH: 37
<212> TYPE: PRT
<213> ORGANISM: Physcomitrella

<400> SEQUENCE: 105

Phe Gly Leu Lys Thr Ser Arg Ser Gly Arg Leu Leu Val Pro Ala Leu
1               5                   10                  15

Ala Tyr Arg Arg Ser Gln Ser Ile Glu Tyr Asp Lys Asp Gly Gly Ile
            20                  25                  30

Ile Ala Ile Phe Asp
            35

<210> SEQ ID NO 106
<211> LENGTH: 37
<212> TYPE: PRT
<213> ORGANISM: Arabidopsis thaliana
<220> FEATURE:
<221> NAME/KEY: SITE
<222> LOCATION: 10
<223> OTHER INFORMATION: Xaa can be any naturally occuring amino acid

```
<220> FEATURE:
<221> NAME/KEY: SITE
<222> LOCATION: 19
<223> OTHER INFORMATION: Xaa can be any naturally occuring amino acid

<400> SEQUENCE: 106

Leu Gly Gln Lys Arg Ser Arg Ser Gly Xaa Val Leu Val Ser Ser Leu
1               5                  10                  15

Glu Phe Xaa Arg Asn Gln Ile Pro Val Tyr Asp Met Asp Arg Asn Leu
            20                  25                  30

Ile Gln Val Lys Asp
        35

<210> SEQ ID NO 107
<211> LENGTH: 37
<212> TYPE: PRT
<213> ORGANISM: Arabidopsis lyrata
<220> FEATURE:
<221> NAME/KEY: SITE
<222> LOCATION: 10
<223> OTHER INFORMATION: Xaa can be any naturally occuring amino acid
<220> FEATURE:
<221> NAME/KEY: SITE
<222> LOCATION: 19
<223> OTHER INFORMATION: Xaa can be any naturally occuring amino acid

<400> SEQUENCE: 107

Val Gly Gln Lys Arg Ser Arg Ser Gly Xaa Val Leu Val Ser Ser Leu
1               5                  10                  15

Glu Phe Xaa Arg Asn Gln Ile Pro Val Tyr Asp Met Asp Arg Asn Leu
            20                  25                  30

Ile Gln Val Lys Asp
        35

<210> SEQ ID NO 108
<211> LENGTH: 37
<212> TYPE: PRT
<213> ORGANISM: Capsella
<220> FEATURE:
<221> NAME/KEY: SITE
<222> LOCATION: 10
<223> OTHER INFORMATION: Xaa can be any naturally occuring amino acid
<220> FEATURE:
<221> NAME/KEY: SITE
<222> LOCATION: 19
<223> OTHER INFORMATION: Xaa can be any naturally occuring amino acid

<400> SEQUENCE: 108

Leu Gly Gln Lys Arg Ser Arg Ser Gly Xaa Val Leu Val Ser Pro Leu
1               5                  10                  15

Glu Phe Xaa Arg Asn Gln Ile Pro Val Tyr Asp Met Asp Arg Asn Leu
            20                  25                  30

Ile Gln Val Lys Asp
        35

<210> SEQ ID NO 109
<211> LENGTH: 37
<212> TYPE: PRT
<213> ORGANISM: Glycine
<220> FEATURE:
<221> NAME/KEY: SITE
<222> LOCATION: 10
<223> OTHER INFORMATION: Xaa can be any naturally occuring amino acid
<220> FEATURE:
<221> NAME/KEY: SITE
<222> LOCATION: 19
<223> OTHER INFORMATION: Xaa can be any naturally occuring amino acid
```

<400> SEQUENCE: 109

Pro Ser Phe Arg Lys Ser Arg Ser Gly Xaa Leu Leu Leu Pro Pro Leu
1               5                   10                  15

Glu Phe Xaa Arg Asn Gln Ile Pro Ile Tyr Asn Ala Asp His Glu Ile
            20                  25                  30

Thr Glu Ile Gln Asp
        35

<210> SEQ ID NO 110
<211> LENGTH: 37
<212> TYPE: PRT
<213> ORGANISM: Glycine
<220> FEATURE:
<223> OTHER INFORMATION: alternative Sequence of Glycine
<220> FEATURE:
<221> NAME/KEY: SITE
<222> LOCATION: 10
<223> OTHER INFORMATION: Xaa can be any naturally occuring amino acid
<220> FEATURE:
<221> NAME/KEY: SITE
<222> LOCATION: 19
<223> OTHER INFORMATION: Xaa can be any naturally occuring amino acid

<400> SEQUENCE: 110

Leu Ser Phe Arg Lys Ser Arg Ser Gly Xaa Leu Leu Leu Pro Pro Leu
1               5                   10                  15

Glu Phe Xaa Arg Asn Gln Ile Pro Ile Tyr Asn Ala Asp His Glu Ile
            20                  25                  30

Thr Glu Ile Arg Asp
        35

<210> SEQ ID NO 111
<211> LENGTH: 37
<212> TYPE: PRT
<213> ORGANISM: Phaseolus
<220> FEATURE:
<221> NAME/KEY: SITE
<222> LOCATION: 10
<223> OTHER INFORMATION: Xaa can be any naturally occuring amino acid
<220> FEATURE:
<221> NAME/KEY: SITE
<222> LOCATION: 19
<223> OTHER INFORMATION: Xaa can be any naturally occuring amino acid

<400> SEQUENCE: 111

Ser Asn Phe Arg Thr Ser Arg Ser Gly Xaa Met Leu Leu Pro Pro Leu
1               5                   10                  15

Glu Phe Xaa Arg Asn Gln Ile Pro Ile Tyr Asp Ala Asp His Glu Leu
            20                  25                  30

Lys Glu Ile Lys Asp
        35

<210> SEQ ID NO 112
<211> LENGTH: 37
<212> TYPE: PRT
<213> ORGANISM: Medicago
<220> FEATURE:
<221> NAME/KEY: SITE
<222> LOCATION: 10
<223> OTHER INFORMATION: Xaa can be any naturally occuring amino acid
<220> FEATURE:
<221> NAME/KEY: SITE
<222> LOCATION: 19
<223> OTHER INFORMATION: Xaa can be any naturally occuring amino acid

<400> SEQUENCE: 112

-continued

```
Leu Gly Leu Lys Lys Ser Arg Ser Gly Xaa Trp Leu Leu Pro Arg Leu
1               5                   10                  15

Glu Phe Xaa Arg Asn Gln Thr Pro Ile Tyr Asn Met Asp Arg Glu Ile
            20                  25                  30

Ile Glu Ile Gln Glu
        35
```

<210> SEQ ID NO 113
<211> LENGTH: 37
<212> TYPE: PRT
<213> ORGANISM: Medicago
<220> FEATURE:
<221> NAME/KEY: SITE
<222> LOCATION: 10
<223> OTHER INFORMATION: Xaa can be any naturally occuring amino acid
<220> FEATURE:
<221> NAME/KEY: SITE
<222> LOCATION: 19
<223> OTHER INFORMATION: Xaa can be any naturally occuring amino acid

<400> SEQUENCE: 113

```
Leu Ser Leu Lys Lys Ser Arg Ser Gly Xaa Trp Leu Leu Pro Pro Leu
1               5                   10                  15

Glu Phe Xaa Arg Asn Gln Gln Pro Ile Tyr Asn Met Asp Arg Glu Ile
            20                  25                  30

Thr Glu Ile Gln Glu
        35
```

<210> SEQ ID NO 114
<211> LENGTH: 37
<212> TYPE: PRT
<213> ORGANISM: Cicer
<220> FEATURE:
<221> NAME/KEY: SITE
<222> LOCATION: 10
<223> OTHER INFORMATION: Xaa can be any naturally occuring amino acid
<220> FEATURE:
<221> NAME/KEY: SITE
<222> LOCATION: 19
<223> OTHER INFORMATION: Xaa can be any naturally occuring amino acid

<400> SEQUENCE: 114

```
Leu Ser Leu Lys Lys Ser Arg Ser Gly Xaa Leu Leu Leu Pro Pro Leu
1               5                   10                  15

Glu Phe Xaa His Asn Gln Lys Pro Ile Tyr Asn Val Asp Arg Glu Ile
            20                  25                  30

Thr Glu Ile Gln Ala
        35
```

<210> SEQ ID NO 115
<211> LENGTH: 37
<212> TYPE: PRT
<213> ORGANISM: Citrus sinensis
<220> FEATURE:
<221> NAME/KEY: SITE
<222> LOCATION: 10
<223> OTHER INFORMATION: Xaa can be any naturally occuring amino acid
<220> FEATURE:
<221> NAME/KEY: SITE
<222> LOCATION: 19
<223> OTHER INFORMATION: Xaa can be any naturally occuring amino acid

<400> SEQUENCE: 115

```
Leu Ser Leu Lys Arg Ser Arg Ser Gly Xaa Leu Leu Val Pro Cys Leu
1               5                   10                  15
```

Asp Phe Xaa Arg Asn Gln Ile Ala Val Tyr Asp Ala Asp Arg Asn Ile
            20                  25                  30

Thr Gly Ile Gln Glu
        35

<210> SEQ ID NO 116
<211> LENGTH: 37
<212> TYPE: PRT
<213> ORGANISM: Vitis
<220> FEATURE:
<221> NAME/KEY: SITE
<222> LOCATION: 10
<223> OTHER INFORMATION: Xaa can be any naturally occuring amino acid
<220> FEATURE:
<221> NAME/KEY: SITE
<222> LOCATION: 19
<223> OTHER INFORMATION: Xaa can be any naturally occuring amino acid

<400> SEQUENCE: 116

Leu Ser Leu Lys Arg Ser Arg Ser Gly Xaa Leu Leu Leu Pro Ser Leu
1               5                   10                  15

Asp Phe Xaa Arg Asn Gln Lys Ala Val Tyr Asp Ala Asp Arg Arg Ile
            20                  25                  30

Thr Gly Ile Gln Glu
        35

<210> SEQ ID NO 117
<211> LENGTH: 37
<212> TYPE: PRT
<213> ORGANISM: Theobroma
<220> FEATURE:
<221> NAME/KEY: SITE
<222> LOCATION: 10
<223> OTHER INFORMATION: Xaa can be any naturally occuring amino acid
<220> FEATURE:
<221> NAME/KEY: SITE
<222> LOCATION: 19
<223> OTHER INFORMATION: Xaa can be any naturally occuring amino acid

<400> SEQUENCE: 117

Leu Ser Leu Lys Cys Ser Arg Ser Gly Xaa Leu Leu Leu Pro Arg Leu
1               5                   10                  15

Glu Phe Xaa Arg Asn Gln Ile Ala Val Tyr Asp Gln Thr Arg Lys Ile
            20                  25                  30

Thr Gly Ile Arg Glu
        35

<210> SEQ ID NO 118
<211> LENGTH: 37
<212> TYPE: PRT
<213> ORGANISM: Solanum
<220> FEATURE:
<221> NAME/KEY: SITE
<222> LOCATION: 10
<223> OTHER INFORMATION: Xaa can be any naturally occuring amino acid
<220> FEATURE:
<221> NAME/KEY: SITE
<222> LOCATION: 19
<223> OTHER INFORMATION: Xaa can be any naturally occuring amino acid

<400> SEQUENCE: 118

Leu Ser Phe Asn Arg Ser Arg Ser Gly Xaa Val Leu Leu Pro Pro Met
1               5                   10                  15

Ala Phe Xaa Arg Asn Gln Arg Ala Val Tyr Asp Val Ile Leu Phe Thr
            20                  25                  30

Thr Gly Ile Ser Cys

<210> SEQ ID NO 119
<211> LENGTH: 37
<212> TYPE: PRT
<213> ORGANISM: Populus
<220> FEATURE:
<221> NAME/KEY: SITE
<222> LOCATION: 10
<223> OTHER INFORMATION: Xaa can be any naturally occuring amino acid
<220> FEATURE:
<221> NAME/KEY: SITE
<222> LOCATION: 19
<223> OTHER INFORMATION: Xaa can be any naturally occuring amino acid

<400> SEQUENCE: 119

Leu Asn Leu Lys Arg Ser Arg Ser Gly Xaa Leu Leu Leu Pro Thr Leu
1               5                   10                  15

Asp Phe Xaa Arg Asn Gln Ile Pro Val Tyr Asp Glu Val Ser Gly Ile
            20                  25                  30

Ser Gly Ile Phe Pro
        35

<210> SEQ ID NO 120
<211> LENGTH: 37
<212> TYPE: PRT
<213> ORGANISM: Fragaria
<220> FEATURE:
<221> NAME/KEY: SITE
<222> LOCATION: 10
<223> OTHER INFORMATION: Xaa can be any naturally occuring amino acid
<220> FEATURE:
<221> NAME/KEY: SITE
<222> LOCATION: 19
<223> OTHER INFORMATION: Xaa can be any naturally occuring amino acid

<400> SEQUENCE: 120

Leu Ser Thr Gly Arg Ser Arg Ser Gly Xaa Leu Leu Leu Arg Pro Leu
1               5                   10                  15

Glu Phe Xaa Arg Asn Gln Ser Pro Val Tyr Asp Lys Asp His Gly Val
            20                  25                  30

Ile Gly Ile Gln Glu
        35

<210> SEQ ID NO 121
<211> LENGTH: 37
<212> TYPE: PRT
<213> ORGANISM: Fragaria
<220> FEATURE:
<221> NAME/KEY: SITE
<222> LOCATION: 10
<223> OTHER INFORMATION: Xaa can be any naturally occuring amino acid
<220> FEATURE:
<221> NAME/KEY: SITE
<222> LOCATION: 19
<223> OTHER INFORMATION: Xaa can be any naturally occuring amino acid

<400> SEQUENCE: 121

Leu Ser Ala Gly Arg Ser Arg Ser Gly Xaa Leu Arg Leu Arg Pro Leu
1               5                   10                  15

Glu Phe Xaa Arg Asn Gln Ser Ala Val Tyr Asp Lys Asp His Gly Val
            20                  25                  30

Ile Gly Ile Gln Glu
        35

<210> SEQ ID NO 122

```
<211> LENGTH: 37
<212> TYPE: PRT
<213> ORGANISM: Amborella
<220> FEATURE:
<221> NAME/KEY: SITE
<222> LOCATION: 10
<223> OTHER INFORMATION: Xaa can be any naturally occuring amino acid
<220> FEATURE:
<221> NAME/KEY: SITE
<222> LOCATION: 19
<223> OTHER INFORMATION: Xaa can be any naturally occuring amino acid

<400> SEQUENCE: 122

Phe Leu Leu Ser Ile Ser Arg Ser Gly Xaa Ile Ile Val Arg Pro Leu
1               5                   10                  15

Ala Tyr Xaa Cys Asn Glu Arg Ile Val Tyr Gly Lys Asp Gly Ser Ile
            20                  25                  30

Thr Ser Ile Leu Asp
        35

<210> SEQ ID NO 123
<211> LENGTH: 37
<212> TYPE: PRT
<213> ORGANISM: Physcomitrella
<220> FEATURE:
<221> NAME/KEY: SITE
<222> LOCATION: 10
<223> OTHER INFORMATION: Xaa can be any naturally occuring amino acid
<220> FEATURE:
<221> NAME/KEY: SITE
<222> LOCATION: 19
<223> OTHER INFORMATION: Xaa can be any naturally occuring amino acid

<400> SEQUENCE: 123

Phe Gly Leu Lys Thr Ser Arg Ser Gly Xaa Leu Leu Val Pro Ala Leu
1               5                   10                  15

Ala Tyr Xaa Arg Ser Gln Ser Ile Glu Tyr Asp Lys Asp Gly Gly Ile
            20                  25                  30

Ile Ala Ile Phe Asp
        35

<210> SEQ ID NO 124
<211> LENGTH: 13
<212> TYPE: PRT
<213> ORGANISM: Artificial Sequence
<220> FEATURE:
<221> NAME/KEY: SITE
<222> LOCATION: 1
<223> OTHER INFORMATION: Xaa can be R or K
<220> FEATURE:
<223> OTHER INFORMATION: Consensus Sequence
<220> FEATURE:
<221> NAME/KEY: SITE
<222> LOCATION: 2
<223> OTHER INFORMATION: Xaa can be S or T
<220> FEATURE:
<221> NAME/KEY: SITE
<222> LOCATION: 5
<223> OTHER INFORMATION: Xaa can be L or I or V or M or W
<220> FEATURE:
<221> NAME/KEY: SITE
<222> LOCATION: 6
<223> OTHER INFORMATION: Xaa can be L or I or V
<220> FEATURE:
<221> NAME/KEY: SITE
<222> LOCATION: 7
<223> OTHER INFORMATION: Xaa can be L or V
<220> FEATURE:
<221> NAME/KEY: SITE
<222> LOCATION: 8
<223> OTHER INFORMATION: Xaa can be P or S or R
```

```
<220> FEATURE:
<221> NAME/KEY: SITE
<222> LOCATION: 9
<223> OTHER INFORMATION: Xaa can be P or T or S or R or C or K
<220> FEATURE:
<221> NAME/KEY: SITE
<222> LOCATION: 10
<223> OTHER INFORMATION: Xaa can be L or M
<220> FEATURE:
<221> NAME/KEY: SITE
<222> LOCATION: 11
<223> OTHER INFORMATION: Xaa can be A or E or Q or D
<220> FEATURE:
<221> NAME/KEY: SITE
<222> LOCATION: 12
<223> OTHER INFORMATION: Xaa can be F or Y or L or P or K or N
<220> FEATURE:
<221> NAME/KEY: SITE
<222> LOCATION: 13
<223> OTHER INFORMATION: Xaa can be W or G

<400> SEQUENCE: 124

Xaa Xaa Gly Arg Xaa Xaa Xaa Xaa Xaa Xaa Xaa Xaa Xaa
1               5                   10

<210> SEQ ID NO 125
<211> LENGTH: 13
<212> TYPE: PRT
<213> ORGANISM: Artificial Sequence
<220> FEATURE:
<223> OTHER INFORMATION: Consensus Sequence
<220> FEATURE:
<221> NAME/KEY: SITE
<222> LOCATION: 4
<223> OTHER INFORMATION: Xaa can be V or L
<220> FEATURE:
<221> NAME/KEY: SITE
<222> LOCATION: 5
<223> OTHER INFORMATION: Xaa can be V or I
<220> FEATURE:
<221> NAME/KEY: SITE
<222> LOCATION: 8
<223> OTHER INFORMATION: Xaa can be P or T or K
<220> FEATURE:
<221> NAME/KEY: SITE
<222> LOCATION: 10
<223> OTHER INFORMATION: Xaa can be D or A
<220> FEATURE:
<221> NAME/KEY: SITE
<222> LOCATION: 11
<223> OTHER INFORMATION: Xaa can be L or P or K or N
<220> FEATURE:
<221> NAME/KEY: SITE
<222> LOCATION: 12
<223> OTHER INFORMATION: Xaa can be G or W

<400> SEQUENCE: 125

Ser Gly Arg Xaa Xaa Val Pro Xaa Leu Xaa Xaa Xaa Cys
1               5                   10

<210> SEQ ID NO 126
<211> LENGTH: 17
<212> TYPE: PRT
<213> ORGANISM: Artificial Sequence
<220> FEATURE:
<223> OTHER INFORMATION: Consensus sequence
<220> FEATURE:
<221> NAME/KEY: SITE
<222> LOCATION: 3
<223> OTHER INFORMATION: Xaa can be S or T
<220> FEATURE:
<221> NAME/KEY: SITE
<222> LOCATION: 6
<223> OTHER INFORMATION: Xaa can be I or V or L or W or M
<220> FEATURE:
```

```
<221> NAME/KEY: SITE
<222> LOCATION: 7
<223> OTHER INFORMATION: Xaa can be L or I
<220> FEATURE:
<221> NAME/KEY: SITE
<222> LOCATION: 8
<223> OTHER INFORMATION: Xaa can be L or V
<220> FEATURE:
<221> NAME/KEY: SITE
<222> LOCATION: 9
<223> OTHER INFORMATION: Xaa can be P or S or R
<220> FEATURE:
<221> NAME/KEY: SITE
<222> LOCATION: 10
<223> OTHER INFORMATION: Xaa can be P or S or T or C or R
<220> FEATURE:
<221> NAME/KEY: SITE
<222> LOCATION: 11
<223> OTHER INFORMATION: Xaa can be L or M
<220> FEATURE:
<221> NAME/KEY: SITE
<222> LOCATION: 12
<223> OTHER INFORMATION: Xaa can be A or E or D or Q
<220> FEATURE:
<221> NAME/KEY: SITE
<222> LOCATION: 13
<223> OTHER INFORMATION: Xaa can be F or Y
<220> FEATURE:
<221> NAME/KEY: SITE
<222> LOCATION: 15
<223> OTHER INFORMATION: Xaa can be R or C or H
<220> FEATURE:
<221> NAME/KEY: SITE
<222> LOCATION: 17
<223> OTHER INFORMATION: Xaa can be Q or E

<400> SEQUENCE: 126

Ser Arg Xaa Gly Arg Xaa Xaa Xaa Xaa Xaa Xaa Xaa Xaa Trp Xaa Asn
1               5                   10                  15

Xaa

<210> SEQ ID NO 127
<211> LENGTH: 34
<212> TYPE: PRT
<213> ORGANISM: Arabidopsis thaliana

<400> SEQUENCE: 127

Gln Lys Arg Ser Arg Ser Gly Arg Val Leu Val Ser Ser Leu Glu Phe
1               5                   10                  15

Trp Arg Asn Gln Ile Pro Val Tyr Asp Met Asp Arg Asn Leu Ile Gln
            20                  25                  30

Val Lys

<210> SEQ ID NO 128
<211> LENGTH: 34
<212> TYPE: PRT
<213> ORGANISM: Arabidopsis lyrata

<400> SEQUENCE: 128

Gln Lys Arg Ser Arg Ser Gly Arg Val Leu Val Ser Ser Leu Glu Phe
1               5                   10                  15

Trp Arg Asn Gln Ile Pro Val Tyr Asp Met Asp Arg Asn Leu Ile Gln
            20                  25                  30

Val Lys

<210> SEQ ID NO 129
<211> LENGTH: 34
<212> TYPE: PRT
```

<213> ORGANISM: Capsella

<400> SEQUENCE: 129

Gln Lys Arg Ser Arg Ser Gly Arg Val Leu Val Ser Pro Leu Glu Phe
1               5                   10                  15
Trp Arg Asn Gln Ile Pro Val Tyr Asp Met Asp Arg Asn Leu Ile Gln
            20                  25                  30
Val Lys

<210> SEQ ID NO 130
<211> LENGTH: 34
<212> TYPE: PRT
<213> ORGANISM: Glycine

<400> SEQUENCE: 130

Phe Arg Lys Ser Arg Ser Gly Arg Leu Leu Leu Pro Pro Leu Glu Phe
1               5                   10                  15
Trp Arg Asn Gln Ile Pro Ile Tyr Asn Ala Asp His Glu Ile Thr Glu
            20                  25                  30
Ile Gln

<210> SEQ ID NO 131
<211> LENGTH: 34
<212> TYPE: PRT
<213> ORGANISM: Glycine
<220> FEATURE:
<223> OTHER INFORMATION: alternative Sequence of Glycine

<400> SEQUENCE: 131

Phe Arg Lys Ser Arg Ser Gly Arg Leu Leu Leu Pro Pro Leu Glu Phe
1               5                   10                  15
Trp Arg Asn Gln Ile Pro Ile Tyr Asn Ala Asp His Glu Ile Thr Glu
            20                  25                  30
Ile Arg

<210> SEQ ID NO 132
<211> LENGTH: 34
<212> TYPE: PRT
<213> ORGANISM: Phaseolus

<400> SEQUENCE: 132

Phe Arg Thr Ser Arg Ser Gly Arg Met Leu Leu Pro Pro Leu Glu Phe
1               5                   10                  15
Trp Arg Asn Gln Ile Pro Ile Tyr Asp Ala Asp His Glu Leu Lys Glu
            20                  25                  30
Ile Lys

<210> SEQ ID NO 133
<211> LENGTH: 34
<212> TYPE: PRT
<213> ORGANISM: Medicago

<400> SEQUENCE: 133

Leu Lys Lys Ser Arg Ser Gly Arg Trp Leu Leu Pro Arg Leu Glu Phe
1               5                   10                  15
Trp Arg Asn Gln Thr Pro Ile Tyr Asn Met Asp Arg Glu Ile Ile Glu
            20                  25                  30
Ile Gln

```
<210> SEQ ID NO 134
<211> LENGTH: 34
<212> TYPE: PRT
<213> ORGANISM: Medicago

<400> SEQUENCE: 134

Leu Lys Lys Ser Arg Ser Gly Arg Trp Leu Pro Pro Leu Glu Phe
1               5                   10                  15

Trp Arg Asn Gln Gln Pro Ile Tyr Asn Met Asp Arg Glu Ile Thr Glu
            20                  25                  30

Ile Gln

<210> SEQ ID NO 135
<211> LENGTH: 34
<212> TYPE: PRT
<213> ORGANISM: Cicer

<400> SEQUENCE: 135

Leu Lys Lys Ser Arg Ser Gly Arg Leu Leu Pro Pro Leu Glu Phe
1               5                   10                  15

Trp His Asn Gln Lys Pro Ile Tyr Asn Val Asp Arg Glu Ile Thr Glu
            20                  25                  30

Ile Gln

<210> SEQ ID NO 136
<211> LENGTH: 34
<212> TYPE: PRT
<213> ORGANISM: Citrus sinensis

<400> SEQUENCE: 136

Leu Lys Arg Ser Arg Ser Gly Arg Leu Leu Val Pro Cys Leu Asp Phe
1               5                   10                  15

Trp Arg Asn Gln Ile Ala Val Tyr Asp Ala Asp Arg Asn Ile Thr Gly
            20                  25                  30

Ile Gln

<210> SEQ ID NO 137
<211> LENGTH: 34
<212> TYPE: PRT
<213> ORGANISM: Vitis

<400> SEQUENCE: 137

Leu Lys Arg Ser Arg Ser Gly Arg Leu Leu Leu Pro Ser Leu Asp Phe
1               5                   10                  15

Trp Arg Asn Gln Lys Ala Val Tyr Asp Ala Asp Arg Arg Ile Thr Gly
            20                  25                  30

Ile Gln

<210> SEQ ID NO 138
<211> LENGTH: 34
<212> TYPE: PRT
<213> ORGANISM: Theobroma

<400> SEQUENCE: 138

Leu Lys Cys Ser Arg Ser Gly Arg Leu Leu Pro Arg Leu Glu Phe
1               5                   10                  15

Trp Arg Asn Gln Ile Ala Val Tyr Asp Gln Thr Arg Lys Ile Thr Gly
            20                  25                  30

Ile Arg
```

<210> SEQ ID NO 139
<211> LENGTH: 34
<212> TYPE: PRT
<213> ORGANISM: Solanum

<400> SEQUENCE: 139

Phe Asn Arg Ser Arg Ser Gly Arg Val Leu Leu Pro Pro Met Ala Phe
1               5                   10                  15

Trp Arg Asn Gln Arg Ala Val Tyr Asp Val Ile Leu Phe Thr Thr Gly
            20                  25                  30

Ile Ser

<210> SEQ ID NO 140
<211> LENGTH: 34
<212> TYPE: PRT
<213> ORGANISM: Populus

<400> SEQUENCE: 140

Leu Lys Arg Ser Arg Ser Gly Arg Leu Leu Pro Thr Leu Asp Phe
1               5                   10                  15

Trp Arg Asn Gln Ile Pro Val Tyr Asp Glu Val Ser Gly Ile Ser Gly
            20                  25                  30

Ile Phe

<210> SEQ ID NO 141
<211> LENGTH: 34
<212> TYPE: PRT
<213> ORGANISM: Fragaria

<400> SEQUENCE: 141

Thr Gly Arg Ser Arg Ser Gly Arg Leu Leu Leu Arg Pro Leu Glu Phe
1               5                   10                  15

Trp Arg Asn Gln Ser Pro Val Tyr Asp Lys Asp His Gly Val Ile Gly
            20                  25                  30

Ile Gln

<210> SEQ ID NO 142
<211> LENGTH: 34
<212> TYPE: PRT
<213> ORGANISM: Fragaria

<400> SEQUENCE: 142

Ala Gly Arg Ser Arg Ser Gly Arg Leu Arg Leu Arg Pro Leu Glu Phe
1               5                   10                  15

Trp Arg Asn Gln Ser Ala Val Tyr Asp Lys Asp His Gly Val Ile Gly
            20                  25                  30

Ile Gln

<210> SEQ ID NO 143
<211> LENGTH: 34
<212> TYPE: PRT
<213> ORGANISM: Amborella

<400> SEQUENCE: 143

Leu Ser Ile Ser Arg Ser Gly Arg Ile Ile Val Arg Pro Leu Ala Tyr
1               5                   10                  15

Trp Cys Asn Glu Arg Ile Val Tyr Gly Lys Asp Gly Ser Ile Thr Ser
            20                  25                  30

Ile Leu

<210> SEQ ID NO 144
<211> LENGTH: 34
<212> TYPE: PRT
<213> ORGANISM: Brachypodium

<400> SEQUENCE: 144

Met Thr Arg Thr Lys Ser Gly Arg Val Val Pro Pro Leu Asp Leu
1               5                   10                  15

Gly Cys Glu Arg Ile Leu Tyr Gly Asn Asn His Leu Val Leu Gly Val
            20                  25                  30

Ala Pro

<210> SEQ ID NO 145
<211> LENGTH: 34
<212> TYPE: PRT
<213> ORGANISM: Oryza

<400> SEQUENCE: 145

Leu Arg Arg Thr Arg Ser Gly Arg Val Val Val Pro Thr Leu Asp Pro
1               5                   10                  15

Gly Cys Gln Arg Ile Val Tyr Asp Arg Asp Gly Leu Val Ser Gly Val
            20                  25                  30

Ala Gly

<210> SEQ ID NO 146
<211> LENGTH: 34
<212> TYPE: PRT
<213> ORGANISM: Setaria <grass>

<400> SEQUENCE: 146

Leu Arg Lys Thr Arg Ser Gly Arg Val Val Val Pro Thr Leu Asp Lys
1               5                   10                  15

Gly Cys Gln Arg Ile Val Tyr Asp Met Asp Gly Ala Ile Val Gly Val
            20                  25                  30

Val Gly

<210> SEQ ID NO 147
<211> LENGTH: 34
<212> TYPE: PRT
<213> ORGANISM: Sorghum <genus>

<400> SEQUENCE: 147

Leu Lys Arg Ser Arg Ser Gly Arg Val Ile Val Pro Lys Leu Asp Asn
1               5                   10                  15

Trp Cys Gln Thr Ile Val Tyr Gly Arg Asp Gly Leu Ile Ala Ala Val
            20                  25                  30

Ile Gly

<210> SEQ ID NO 148
<211> LENGTH: 33
<212> TYPE: PRT
<213> ORGANISM: Musa

<400> SEQUENCE: 148

Phe Arg Arg Ser Arg Ser Gly Arg Leu Ile Val Pro Pro Leu Asp Asn
1               5                   10                  15

Gly Cys Gln Gln Ile Ile Tyr Asp Ala Asp Gly Ser Thr Gly Ile
            20                  25                  30

Met

<210> SEQ ID NO 149
<211> LENGTH: 34
<212> TYPE: PRT
<213> ORGANISM: Elaeis

<400> SEQUENCE: 149

Leu Lys Arg Ser Arg Ser Gly Arg Leu Ile Val Pro Pro Leu Ala Asn
1               5                   10                  15

Trp Cys Gln Gln Ile Ile Tyr Asp Ala Asp Gly Ser Ile Ala Gly Ile
            20                  25                  30

Arg Gly

<210> SEQ ID NO 150
<211> LENGTH: 34
<212> TYPE: PRT
<213> ORGANISM: Phoenix

<400> SEQUENCE: 150

Leu Lys Arg Ser Arg Ser Gly Arg Leu Ile Val Pro Pro Leu Ala Asn
1               5                   10                  15

Trp Cys Gln Gln Ile Ile Tyr Asn Ala Asp Gly Ser Ile Ala Gly Ile
            20                  25                  30

Arg Gly

<210> SEQ ID NO 151
<211> LENGTH: 34
<212> TYPE: PRT
<213> ORGANISM: Camelina

<400> SEQUENCE: 151

Gln Lys Arg Ser Arg Ser Gly Arg Val Leu Val Ser Ser Leu Glu Tyr
1               5                   10                  15

Trp Arg Asn Gln Ile Pro Val Tyr Asp Met Glu Arg Leu Ile Glu
            20                  25                  30

Val Lys

<210> SEQ ID NO 152
<211> LENGTH: 33
<212> TYPE: PRT
<213> ORGANISM: Brassica

<400> SEQUENCE: 152

Gln Lys Arg Ser Arg Ser Gly Arg Val Leu Val Ser Pro Leu Glu Tyr
1               5                   10                  15

Trp Arg Asn Gln Leu Pro Val Tyr Asp Lys Asp Arg Asn Leu Ile Gln
            20                  25                  30

Val

<210> SEQ ID NO 153
<211> LENGTH: 33
<212> TYPE: PRT
<213> ORGANISM: Vigna

<400> SEQUENCE: 153

Arg Thr Ser Arg Ser Gly Arg Leu Leu Val Pro Pro Leu Glu Phe Trp
1               5                   10                  15

Arg Asn Gln Ile Pro Ile Tyr Asp Ala Asp His Val Leu Lys Glu Ile
            20                  25                  30

Lys

<210> SEQ ID NO 154
<211> LENGTH: 33
<212> TYPE: PRT
<213> ORGANISM: Daucus

<400> SEQUENCE: 154

Lys Arg Ser Arg Ser Gly Arg Ile Leu Leu Pro Thr Leu Glu Tyr Trp
1               5                   10                  15

Arg Asn Gln Thr Ala Ile Tyr Asp Ala Glu His Gln Val Ile Gly Ile
            20                  25                  30

Lys

<210> SEQ ID NO 155
<211> LENGTH: 33
<212> TYPE: PRT
<213> ORGANISM: Ziziphus

<400> SEQUENCE: 155

Lys Arg Ser Arg Ser Gly Arg Leu Leu Leu Pro Thr Leu Glu Phe Trp
1               5                   10                  15

Arg Asn Gln Met Pro Ile Tyr Asp Ala Asp His Lys Leu Ile Gly Ile
            20                  25                  30

Gln

<210> SEQ ID NO 156
<211> LENGTH: 33
<212> TYPE: PRT
<213> ORGANISM: Coffea

<400> SEQUENCE: 156

Gln Arg Ser Arg Ser Gly Arg Leu Leu Leu Pro Thr Met Gln Phe Trp
1               5                   10                  15

Arg Asn Gln Arg Ala Val Tyr Asp Ala Asp Arg Arg Ile Met Gly Ile
            20                  25                  30

Lys

<210> SEQ ID NO 157
<211> LENGTH: 33
<212> TYPE: PRT
<213> ORGANISM: Malus

<400> SEQUENCE: 157

Lys Arg Ser Arg Thr Gly Arg Leu Leu Leu Pro Thr Met Glu Phe Trp
1               5                   10                  15

Arg Asn Gln Ala Ala Val Tyr Asp Leu Asp Arg Asn Ile Thr Gly Ile
            20                  25                  30

Gln

<210> SEQ ID NO 158
<211> LENGTH: 33
<212> TYPE: PRT
<213> ORGANISM: Pyrus

<400> SEQUENCE: 158

Lys Arg Ser Arg Thr Gly Arg Leu Leu Leu Pro Thr Met Glu Phe Trp
1               5                   10                  15

Arg Asn Gln Ala Ala Val Tyr Asp Leu Asp Arg Asn Ile Thr Gly Ile

```
                20                  25                  30
Gln

<210> SEQ ID NO 159
<211> LENGTH: 33
<212> TYPE: PRT
<213> ORGANISM: Ricinus <angiosperm>

<400> SEQUENCE: 159

Lys Arg Ser Arg Ser Gly Arg Leu Leu Pro Thr Leu Asp Phe Trp
1               5                   10                  15

Arg Asn Gln Ile Pro Val Tyr Asp Ala Asp Arg Asn Ile Thr Gly Ile
                20                  25                  30

Gln

<210> SEQ ID NO 160
<211> LENGTH: 33
<212> TYPE: PRT
<213> ORGANISM: Nicotiana

<400> SEQUENCE: 160

Lys Arg Ser Arg Ser Gly Arg Leu Leu Leu Pro Pro Met Glu Phe Trp
1               5                   10                  15

Arg Asn Gln Met Ala Ile Tyr Asp Ala Asp Arg Arg Val Thr Ala Ile
                20                  25                  30

Lys

<210> SEQ ID NO 161
<211> LENGTH: 33
<212> TYPE: PRT
<213> ORGANISM: Gossypium

<400> SEQUENCE: 161

Lys Arg Ser Arg Ser Gly Arg Val Leu Leu Pro Arg Met Glu Phe Trp
1               5                   10                  15

Arg Asn Gln Ile Pro Val Tyr Asp Gln Asp Arg Arg Ile Thr Gly Ile
                20                  25                  30

Lys

<210> SEQ ID NO 162
<211> LENGTH: 33
<212> TYPE: PRT
<213> ORGANISM: Prunus

<400> SEQUENCE: 162

Arg Arg Ser Arg Ser Gly Arg Leu Leu Leu Pro Thr Met Glu Phe Trp
1               5                   10                  15

Arg Asn Gln Leu Ala Ile Tyr Asp Ser Asp Arg Lys Val Thr Gly Ile
                20                  25                  30

Gln

<210> SEQ ID NO 163
<211> LENGTH: 28
<212> TYPE: PRT
<213> ORGANISM: Cucumis

<400> SEQUENCE: 163

Arg Ser Arg Ser Gly Arg Val Leu Leu Pro Thr Met Glu Phe Trp Arg
1               5                   10                  15
```

```
Asn Gln Leu Pro Val Tyr Asp Ser Asp Arg Lys Leu
            20                  25
```

```
<210> SEQ ID NO 164
<211> LENGTH: 34
<212> TYPE: PRT
<213> ORGANISM: Arabidopsis thaliana
<220> FEATURE:
<223> OTHER INFORMATION: X is not R
<220> FEATURE:
<221> NAME/KEY: SITE
<222> LOCATION: 8
<223> OTHER INFORMATION: X is not R

<400> SEQUENCE: 164
```

```
Gln Lys Arg Ser Arg Ser Gly Xaa Val Leu Val Ser Ser Leu Glu Phe
1               5                   10                  15

Trp Arg Asn Gln Ile Pro Val Tyr Asp Met Asp Arg Asn Leu Ile Gln
            20                  25                  30

Val Lys
```

```
<210> SEQ ID NO 165
<211> LENGTH: 34
<212> TYPE: PRT
<213> ORGANISM: Arabidopsis lyrata
<220> FEATURE:
<223> OTHER INFORMATION: X is not R
<220> FEATURE:
<221> NAME/KEY: SITE
<222> LOCATION: 8
<223> OTHER INFORMATION: X is not R

<400> SEQUENCE: 165
```

```
Gln Lys Arg Ser Arg Ser Gly Xaa Val Leu Val Ser Ser Leu Glu Phe
1               5                   10                  15

Trp Arg Asn Gln Ile Pro Val Tyr Asp Met Asp Arg Asn Leu Ile Gln
            20                  25                  30

Val Lys
```

```
<210> SEQ ID NO 166
<211> LENGTH: 34
<212> TYPE: PRT
<213> ORGANISM: Capsella
<220> FEATURE:
<223> OTHER INFORMATION: X is not R
<220> FEATURE:
<221> NAME/KEY: SITE
<222> LOCATION: 8
<223> OTHER INFORMATION: X is not R

<400> SEQUENCE: 166
```

```
Gln Lys Arg Ser Arg Ser Gly Xaa Val Leu Val Ser Pro Leu Glu Phe
1               5                   10                  15

Trp Arg Asn Gln Ile Pro Val Tyr Asp Met Asp Arg Asn Leu Ile Gln
            20                  25                  30

Val Lys
```

```
<210> SEQ ID NO 167
<211> LENGTH: 34
<212> TYPE: PRT
<213> ORGANISM: Glycine
<220> FEATURE:
<223> OTHER INFORMATION: X is not R
<220> FEATURE:
<221> NAME/KEY: SITE
<222> LOCATION: 8
```

<223> OTHER INFORMATION: X is not R

<400> SEQUENCE: 167

Phe Arg Lys Ser Arg Ser Gly Xaa Leu Leu Leu Pro Pro Leu Glu Phe
1               5                   10                  15

Trp Arg Asn Gln Ile Pro Ile Tyr Asn Ala Asp His Glu Ile Thr Glu
            20                  25                  30

Ile Gln

<210> SEQ ID NO 168
<211> LENGTH: 34
<212> TYPE: PRT
<213> ORGANISM: Glycine
<220> FEATURE:
<223> OTHER INFORMATION: alternative Sequence of Glycine; X is not R
<220> FEATURE:
<221> NAME/KEY: SITE
<222> LOCATION: 8
<223> OTHER INFORMATION: X is not R

<400> SEQUENCE: 168

Phe Arg Lys Ser Arg Ser Gly Xaa Leu Leu Leu Pro Pro Leu Glu Phe
1               5                   10                  15

Trp Arg Asn Gln Ile Pro Ile Tyr Asn Ala Asp His Glu Ile Thr Glu
            20                  25                  30

Ile Arg

<210> SEQ ID NO 169
<211> LENGTH: 34
<212> TYPE: PRT
<213> ORGANISM: Phaseolus
<220> FEATURE:
<223> OTHER INFORMATION: X is not R
<220> FEATURE:
<221> NAME/KEY: SITE
<222> LOCATION: 8
<223> OTHER INFORMATION: X is not R

<400> SEQUENCE: 169

Phe Arg Thr Ser Arg Ser Gly Xaa Met Leu Leu Pro Pro Leu Glu Phe
1               5                   10                  15

Trp Arg Asn Gln Ile Pro Ile Tyr Asp Ala Asp His Glu Leu Lys Glu
            20                  25                  30

Ile Lys

<210> SEQ ID NO 170
<211> LENGTH: 34
<212> TYPE: PRT
<213> ORGANISM: Medicago
<220> FEATURE:
<223> OTHER INFORMATION: X is not R
<220> FEATURE:
<221> NAME/KEY: SITE
<222> LOCATION: 8
<223> OTHER INFORMATION: X is not R

<400> SEQUENCE: 170

Leu Lys Lys Ser Arg Ser Gly Xaa Trp Leu Leu Pro Arg Leu Glu Phe
1               5                   10                  15

Trp Arg Asn Gln Thr Pro Ile Tyr Asn Met Asp Arg Glu Ile Ile Glu
            20                  25                  30

Ile Gln

-continued

```
<210> SEQ ID NO 171
<211> LENGTH: 34
<212> TYPE: PRT
<213> ORGANISM: Medicago
<220> FEATURE:
<223> OTHER INFORMATION: X is not R
<220> FEATURE:
<221> NAME/KEY: SITE
<222> LOCATION: 8
<223> OTHER INFORMATION: X is not R

<400> SEQUENCE: 171

Leu Lys Lys Ser Arg Ser Gly Xaa Trp Leu Leu Pro Pro Leu Glu Phe
1               5                   10                  15

Trp Arg Asn Gln Gln Pro Ile Tyr Asn Met Asp Arg Glu Ile Thr Glu
            20                  25                  30

Ile Gln

<210> SEQ ID NO 172
<211> LENGTH: 34
<212> TYPE: PRT
<213> ORGANISM: Cicer
<220> FEATURE:
<223> OTHER INFORMATION: X is not R
<220> FEATURE:
<221> NAME/KEY: SITE
<222> LOCATION: 8
<223> OTHER INFORMATION: X is not R

<400> SEQUENCE: 172

Leu Lys Lys Ser Arg Ser Gly Xaa Leu Leu Leu Pro Pro Leu Glu Phe
1               5                   10                  15

Trp His Asn Gln Lys Pro Ile Tyr Asn Val Asp Arg Glu Ile Thr Glu
            20                  25                  30

Ile Gln

<210> SEQ ID NO 173
<211> LENGTH: 34
<212> TYPE: PRT
<213> ORGANISM: Citrus sinensis
<220> FEATURE:
<223> OTHER INFORMATION: X is not R
<220> FEATURE:
<221> NAME/KEY: SITE
<222> LOCATION: 8
<223> OTHER INFORMATION: X is not R

<400> SEQUENCE: 173

Leu Lys Arg Ser Arg Ser Gly Xaa Leu Leu Val Pro Cys Leu Asp Phe
1               5                   10                  15

Trp Arg Asn Gln Ile Ala Val Tyr Asp Ala Asp Arg Asn Ile Thr Gly
            20                  25                  30

Ile Gln

<210> SEQ ID NO 174
<211> LENGTH: 34
<212> TYPE: PRT
<213> ORGANISM: Vitis
<220> FEATURE:
<223> OTHER INFORMATION: X is not R
<220> FEATURE:
<221> NAME/KEY: SITE
<222> LOCATION: 8
<223> OTHER INFORMATION: X is not R

<400> SEQUENCE: 174
```

Leu Lys Arg Ser Arg Ser Gly Xaa Leu Leu Pro Ser Leu Asp Phe
1               5                   10                  15

Trp Arg Asn Gln Lys Ala Val Tyr Asp Ala Asp Arg Ile Thr Gly
            20                  25                  30

Ile Gln

<210> SEQ ID NO 175
<211> LENGTH: 34
<212> TYPE: PRT
<213> ORGANISM: Theobroma
<220> FEATURE:
<223> OTHER INFORMATION: X is not R
<220> FEATURE:
<221> NAME/KEY: SITE
<222> LOCATION: 8
<223> OTHER INFORMATION: X is not R

<400> SEQUENCE: 175

Leu Lys Cys Ser Arg Ser Gly Xaa Leu Leu Pro Arg Leu Glu Phe
1               5                   10                  15

Trp Arg Asn Gln Ile Ala Val Tyr Asp Gln Thr Arg Lys Ile Thr Gly
            20                  25                  30

Ile Arg

<210> SEQ ID NO 176
<211> LENGTH: 34
<212> TYPE: PRT
<213> ORGANISM: Solanum
<220> FEATURE:
<223> OTHER INFORMATION: X is not R
<220> FEATURE:
<221> NAME/KEY: SITE
<222> LOCATION: 8
<223> OTHER INFORMATION: X is not R

<400> SEQUENCE: 176

Phe Asn Arg Ser Arg Ser Gly Xaa Val Leu Leu Pro Pro Met Ala Phe
1               5                   10                  15

Trp Arg Asn Gln Arg Ala Val Tyr Asp Val Ile Leu Phe Thr Thr Gly
            20                  25                  30

Ile Ser

<210> SEQ ID NO 177
<211> LENGTH: 34
<212> TYPE: PRT
<213> ORGANISM: Populus
<220> FEATURE:
<223> OTHER INFORMATION: X is not R
<220> FEATURE:
<221> NAME/KEY: SITE
<222> LOCATION: 8
<223> OTHER INFORMATION: X is not R

<400> SEQUENCE: 177

Leu Lys Arg Ser Arg Ser Gly Xaa Leu Leu Pro Thr Leu Asp Phe
1               5                   10                  15

Trp Arg Asn Gln Ile Pro Val Tyr Asp Glu Val Ser Gly Ile Ser Gly
            20                  25                  30

Ile Phe

<210> SEQ ID NO 178
<211> LENGTH: 34
<212> TYPE: PRT
<213> ORGANISM: Fragaria

```
-continued

<220> FEATURE:
<223> OTHER INFORMATION: X is not R
<220> FEATURE:
<221> NAME/KEY: SITE
<222> LOCATION: 8
<223> OTHER INFORMATION: X is not R

<400> SEQUENCE: 178

Thr Gly Arg Ser Arg Ser Gly Xaa Leu Leu Leu Arg Pro Leu Glu Phe
1               5                   10                  15

Trp Arg Asn Gln Ser Pro Val Tyr Asp Lys Asp His Gly Val Ile Gly
            20                  25                  30

Ile Gln

<210> SEQ ID NO 179
<211> LENGTH: 34
<212> TYPE: PRT
<213> ORGANISM: Fragaria
<220> FEATURE:
<223> OTHER INFORMATION: X is not R
<220> FEATURE:
<221> NAME/KEY: SITE
<222> LOCATION: 8
<223> OTHER INFORMATION: X is not R

<400> SEQUENCE: 179

Ala Gly Arg Ser Arg Ser Gly Xaa Leu Arg Leu Arg Pro Leu Glu Phe
1               5                   10                  15

Trp Arg Asn Gln Ser Ala Val Tyr Asp Lys Asp His Gly Val Ile Gly
            20                  25                  30

Ile Gln

<210> SEQ ID NO 180
<211> LENGTH: 34
<212> TYPE: PRT
<213> ORGANISM: Amborella
<220> FEATURE:
<223> OTHER INFORMATION: X is not R
<220> FEATURE:
<221> NAME/KEY: SITE
<222> LOCATION: 8
<223> OTHER INFORMATION: X is not R

<400> SEQUENCE: 180

Leu Ser Ile Ser Arg Ser Gly Xaa Ile Ile Val Arg Pro Leu Ala Tyr
1               5                   10                  15

Trp Cys Asn Glu Arg Ile Val Tyr Gly Lys Asp Gly Ser Ile Thr Ser
            20                  25                  30

Ile Leu

<210> SEQ ID NO 181
<211> LENGTH: 34
<212> TYPE: PRT
<213> ORGANISM: Brachypodium
<220> FEATURE:
<223> OTHER INFORMATION: X is not R
<220> FEATURE:
<221> NAME/KEY: SITE
<222> LOCATION: 8
<223> OTHER INFORMATION: X is not R

<400> SEQUENCE: 181

Met Thr Arg Thr Lys Ser Gly Xaa Val Val Val Pro Pro Leu Asp Leu
1               5                   10                  15

Gly Cys Glu Arg Ile Leu Tyr Gly Asn Asn His Leu Val Leu Gly Val
```

Ala Pro

<210> SEQ ID NO 182
<211> LENGTH: 34
<212> TYPE: PRT
<213> ORGANISM: Oryza
<220> FEATURE:
<223> OTHER INFORMATION: X is not R
<220> FEATURE:
<221> NAME/KEY: SITE
<222> LOCATION: 8
<223> OTHER INFORMATION: X is not R

<400> SEQUENCE: 182

Leu Arg Arg Thr Arg Ser Gly Xaa Val Val Pro Thr Leu Asp Pro
1               5                   10                  15

Gly Cys Gln Arg Ile Val Tyr Asp Arg Asp Gly Leu Val Ser Gly Val
            20                  25                  30

Ala Gly

<210> SEQ ID NO 183
<211> LENGTH: 34
<212> TYPE: PRT
<213> ORGANISM: Setaria <grass>
<220> FEATURE:
<223> OTHER INFORMATION: X is not R
<220> FEATURE:
<221> NAME/KEY: SITE
<222> LOCATION: 8
<223> OTHER INFORMATION: X is not R

<400> SEQUENCE: 183

Leu Arg Lys Thr Arg Ser Gly Xaa Val Val Pro Thr Leu Asp Lys
1               5                   10                  15

Gly Cys Gln Arg Ile Val Tyr Asp Met Asp Gly Ala Ile Val Gly Val
            20                  25                  30

Val Gly

<210> SEQ ID NO 184
<211> LENGTH: 34
<212> TYPE: PRT
<213> ORGANISM: Sorghum <genus>
<220> FEATURE:
<223> OTHER INFORMATION: X is not R
<220> FEATURE:
<221> NAME/KEY: SITE
<222> LOCATION: 8
<223> OTHER INFORMATION: X is not R

<400> SEQUENCE: 184

Leu Lys Arg Ser Arg Ser Gly Xaa Val Ile Val Pro Lys Leu Asp Asn
1               5                   10                  15

Trp Cys Gln Thr Ile Val Tyr Gly Arg Asp Gly Leu Ile Ala Ala Val
            20                  25                  30

Ile Gly

<210> SEQ ID NO 185
<211> LENGTH: 33
<212> TYPE: PRT
<213> ORGANISM: Musa
<220> FEATURE:
<223> OTHER INFORMATION: X is not R
<220> FEATURE:
<221> NAME/KEY: SITE

```
<222> LOCATION: 8
<223> OTHER INFORMATION: X is not R

<400> SEQUENCE: 185

Phe Arg Arg Ser Arg Ser Gly Xaa Leu Ile Val Pro Pro Leu Asp Asn
1               5                   10                  15

Gly Cys Gln Gln Ile Ile Tyr Asp Ala Asp Gly Ser Ile Thr Gly Ile
            20                  25                  30

Met

<210> SEQ ID NO 186
<211> LENGTH: 34
<212> TYPE: PRT
<213> ORGANISM: Elaeis
<220> FEATURE:
<223> OTHER INFORMATION: X is not R
<220> FEATURE:
<221> NAME/KEY: SITE
<222> LOCATION: 8
<223> OTHER INFORMATION: X is not R

<400> SEQUENCE: 186

Leu Lys Arg Ser Arg Ser Gly Xaa Leu Ile Val Pro Pro Leu Ala Asn
1               5                   10                  15

Trp Cys Gln Gln Ile Ile Tyr Asp Ala Asp Gly Ser Ile Ala Gly Ile
            20                  25                  30

Arg Gly

<210> SEQ ID NO 187
<211> LENGTH: 34
<212> TYPE: PRT
<213> ORGANISM: Phoenix
<220> FEATURE:
<223> OTHER INFORMATION: X is not R
<220> FEATURE:
<221> NAME/KEY: SITE
<222> LOCATION: 8
<223> OTHER INFORMATION: X is not R

<400> SEQUENCE: 187

Leu Lys Arg Ser Arg Ser Gly Xaa Leu Ile Val Pro Pro Leu Ala Asn
1               5                   10                  15

Trp Cys Gln Gln Ile Ile Tyr Asn Ala Asp Gly Ser Ile Ala Gly Ile
            20                  25                  30

Arg Gly

<210> SEQ ID NO 188
<211> LENGTH: 34
<212> TYPE: PRT
<213> ORGANISM: Camelina
<220> FEATURE:
<223> OTHER INFORMATION: X is not R
<220> FEATURE:
<221> NAME/KEY: SITE
<222> LOCATION: 8
<223> OTHER INFORMATION: X is not R

<400> SEQUENCE: 188

Gln Lys Arg Ser Arg Ser Gly Xaa Val Leu Val Ser Ser Leu Glu Tyr
1               5                   10                  15

Trp Arg Asn Gln Ile Pro Val Tyr Asp Met Glu Arg Arg Leu Ile Glu
            20                  25                  30

Val Lys
```

<210> SEQ ID NO 189
<211> LENGTH: 33
<212> TYPE: PRT
<213> ORGANISM: Brassica
<220> FEATURE:
<223> OTHER INFORMATION: X is not R
<220> FEATURE:
<221> NAME/KEY: SITE
<222> LOCATION: 8
<223> OTHER INFORMATION: X is not R

<400> SEQUENCE: 189

Gln Lys Arg Ser Arg Ser Gly Xaa Val Leu Val Ser Pro Leu Glu Tyr
1               5                   10                  15

Trp Arg Asn Gln Leu Pro Val Tyr Asp Lys Asp Arg Asn Leu Ile Gln
            20                  25                  30

Val

<210> SEQ ID NO 190
<211> LENGTH: 33
<212> TYPE: PRT
<213> ORGANISM: Vigna
<220> FEATURE:
<223> OTHER INFORMATION: X is not R
<220> FEATURE:
<221> NAME/KEY: SITE
<222> LOCATION: 7
<223> OTHER INFORMATION: X is not R

<400> SEQUENCE: 190

Arg Thr Ser Arg Ser Gly Xaa Leu Leu Val Pro Pro Leu Glu Phe Trp
1               5                   10                  15

Arg Asn Gln Ile Pro Ile Tyr Asp Ala Asp His Val Leu Lys Glu Ile
            20                  25                  30

Lys

<210> SEQ ID NO 191
<211> LENGTH: 33
<212> TYPE: PRT
<213> ORGANISM: Daucus
<220> FEATURE:
<223> OTHER INFORMATION: X is not R
<220> FEATURE:
<221> NAME/KEY: SITE
<222> LOCATION: 7
<223> OTHER INFORMATION: X is not R

<400> SEQUENCE: 191

Lys Arg Ser Arg Ser Gly Xaa Ile Leu Leu Pro Thr Leu Glu Tyr Trp
1               5                   10                  15

Arg Asn Gln Thr Ala Ile Tyr Asp Ala Glu His Gln Val Ile Gly Ile
            20                  25                  30

Lys

<210> SEQ ID NO 192
<211> LENGTH: 33
<212> TYPE: PRT
<213> ORGANISM: Ziziphus
<220> FEATURE:
<223> OTHER INFORMATION: X is not R
<220> FEATURE:
<221> NAME/KEY: SITE
<222> LOCATION: 7
<223> OTHER INFORMATION: X is not R

<400> SEQUENCE: 192

-continued

```
Lys Arg Ser Arg Ser Gly Xaa Leu Leu Leu Pro Thr Leu Glu Phe Trp
1               5                   10                  15

Arg Asn Gln Met Pro Ile Tyr Asp Ala Asp His Lys Leu Ile Gly Ile
            20                  25                  30

Gln

<210> SEQ ID NO 193
<211> LENGTH: 33
<212> TYPE: PRT
<213> ORGANISM: Coffea
<220> FEATURE:
<223> OTHER INFORMATION: X is not R
<220> FEATURE:
<221> NAME/KEY: SITE
<222> LOCATION: 7
<223> OTHER INFORMATION: X is not R

<400> SEQUENCE: 193

Gln Arg Ser Arg Ser Gly Xaa Leu Leu Leu Pro Thr Met Gln Phe Trp
1               5                   10                  15

Arg Asn Gln Arg Ala Val Tyr Asp Ala Asp Arg Arg Ile Met Gly Ile
            20                  25                  30

Lys

<210> SEQ ID NO 194
<211> LENGTH: 33
<212> TYPE: PRT
<213> ORGANISM: Malus
<220> FEATURE:
<223> OTHER INFORMATION: X is not R
<220> FEATURE:
<221> NAME/KEY: SITE
<222> LOCATION: 7
<223> OTHER INFORMATION: X is not R

<400> SEQUENCE: 194

Lys Arg Ser Arg Thr Gly Xaa Leu Leu Leu Pro Thr Met Glu Phe Trp
1               5                   10                  15

Arg Asn Gln Ala Ala Val Tyr Asp Leu Asp Arg Asn Ile Thr Gly Ile
            20                  25                  30

Gln

<210> SEQ ID NO 195
<211> LENGTH: 33
<212> TYPE: PRT
<213> ORGANISM: Pyrus
<220> FEATURE:
<223> OTHER INFORMATION: X is not R
<220> FEATURE:
<221> NAME/KEY: SITE
<222> LOCATION: 7
<223> OTHER INFORMATION: X is not R

<400> SEQUENCE: 195

Lys Arg Ser Arg Thr Gly Xaa Leu Leu Leu Pro Thr Met Glu Phe Trp
1               5                   10                  15

Arg Asn Gln Ala Ala Val Tyr Asp Leu Asp Arg Asn Ile Thr Gly Ile
            20                  25                  30

Gln

<210> SEQ ID NO 196
<211> LENGTH: 33
<212> TYPE: PRT
```

-continued

```
<213> ORGANISM: Ricinus <angiosperm>
<220> FEATURE:
<223> OTHER INFORMATION: X is not R
<220> FEATURE:
<221> NAME/KEY: SITE
<222> LOCATION: 7
<223> OTHER INFORMATION: X is not R

<400> SEQUENCE: 196

Lys Arg Ser Arg Ser Gly Xaa Leu Leu Leu Pro Thr Leu Asp Phe Trp
1               5                   10                  15

Arg Asn Gln Ile Pro Val Tyr Asp Ala Asp Arg Asn Ile Thr Gly Ile
            20                  25                  30

Gln

<210> SEQ ID NO 197
<211> LENGTH: 33
<212> TYPE: PRT
<213> ORGANISM: Nicotiana
<220> FEATURE:
<223> OTHER INFORMATION: X is not R
<220> FEATURE:
<221> NAME/KEY: SITE
<222> LOCATION: 7
<223> OTHER INFORMATION: X is not R

<400> SEQUENCE: 197

Lys Arg Ser Arg Ser Gly Xaa Leu Leu Leu Pro Pro Met Glu Phe Trp
1               5                   10                  15

Arg Asn Gln Met Ala Ile Tyr Asp Ala Asp Arg Arg Val Thr Ala Ile
            20                  25                  30

Lys

<210> SEQ ID NO 198
<211> LENGTH: 33
<212> TYPE: PRT
<213> ORGANISM: Gossypium
<220> FEATURE:
<223> OTHER INFORMATION: X is not R
<220> FEATURE:
<221> NAME/KEY: SITE
<222> LOCATION: 7
<223> OTHER INFORMATION: X is not R

<400> SEQUENCE: 198

Lys Arg Ser Arg Ser Gly Xaa Val Leu Leu Pro Arg Met Glu Phe Trp
1               5                   10                  15

Arg Asn Gln Ile Pro Val Tyr Asp Gln Asp Arg Arg Ile Thr Gly Ile
            20                  25                  30

Lys

<210> SEQ ID NO 199
<211> LENGTH: 33
<212> TYPE: PRT
<213> ORGANISM: Prunus
<220> FEATURE:
<223> OTHER INFORMATION: X is not R
<220> FEATURE:
<221> NAME/KEY: SITE
<222> LOCATION: 7
<223> OTHER INFORMATION: X is not R

<400> SEQUENCE: 199

Arg Arg Ser Arg Ser Gly Xaa Leu Leu Leu Pro Thr Met Glu Phe Trp
1               5                   10                  15
```

```
Arg Asn Gln Leu Ala Ile Tyr Asp Ser Asp Arg Lys Val Thr Gly Ile
             20                  25                  30

Gln
```

```
<210> SEQ ID NO 200
<211> LENGTH: 28
<212> TYPE: PRT
<213> ORGANISM: Cucumis
<220> FEATURE:
<223> OTHER INFORMATION: X is not R
<220> FEATURE:
<221> NAME/KEY: SITE
<222> LOCATION: 6
<223> OTHER INFORMATION: X is not R

<400> SEQUENCE: 200

Arg Ser Arg Ser Gly Xaa Val Leu Leu Pro Thr Met Glu Phe Trp Arg
1               5                   10                  15

Asn Gln Leu Pro Val Tyr Asp Ser Asp Arg Lys Leu
             20                  25
```

```
<210> SEQ ID NO 201
<211> LENGTH: 34
<212> TYPE: PRT
<213> ORGANISM: Arabidopsis thaliana
<220> FEATURE:
<223> OTHER INFORMATION: X is not W
<220> FEATURE:
<221> NAME/KEY: SITE
<222> LOCATION: 17
<223> OTHER INFORMATION: X is not W

<400> SEQUENCE: 201

Gln Lys Arg Ser Arg Ser Gly Arg Val Leu Val Ser Ser Leu Glu Phe
1               5                   10                  15

Xaa Arg Asn Gln Ile Pro Val Tyr Asp Met Asp Arg Asn Leu Ile Gln
             20                  25                  30

Val Lys
```

```
<210> SEQ ID NO 202
<211> LENGTH: 34
<212> TYPE: PRT
<213> ORGANISM: Arabidopsis lyrata
<220> FEATURE:
<223> OTHER INFORMATION: X is not W
<220> FEATURE:
<221> NAME/KEY: SITE
<222> LOCATION: 17
<223> OTHER INFORMATION: X is not W

<400> SEQUENCE: 202

Gln Lys Arg Ser Arg Ser Gly Arg Val Leu Val Ser Ser Leu Glu Phe
1               5                   10                  15

Xaa Arg Asn Gln Ile Pro Val Tyr Asp Met Asp Arg Asn Leu Ile Gln
             20                  25                  30

Val Lys
```

```
<210> SEQ ID NO 203
<211> LENGTH: 34
<212> TYPE: PRT
<213> ORGANISM: Capsella
<220> FEATURE:
<223> OTHER INFORMATION: X is not W
<220> FEATURE:
<221> NAME/KEY: SITE
<222> LOCATION: 17
```

-continued

<223> OTHER INFORMATION: X is not W

<400> SEQUENCE: 203

Gln Lys Arg Ser Arg Ser Gly Arg Val Leu Val Ser Pro Leu Glu Phe
1               5                   10                  15

Xaa Arg Asn Gln Ile Pro Val Tyr Asp Met Asp Arg Asn Leu Ile Gln
            20                  25                  30

Val Lys

<210> SEQ ID NO 204
<211> LENGTH: 34
<212> TYPE: PRT
<213> ORGANISM: Glycine
<220> FEATURE:
<223> OTHER INFORMATION: X is not W
<220> FEATURE:
<221> NAME/KEY: SITE
<222> LOCATION: 17
<223> OTHER INFORMATION: X is not W

<400> SEQUENCE: 204

Phe Arg Lys Ser Arg Ser Gly Arg Leu Leu Leu Pro Pro Leu Glu Phe
1               5                   10                  15

Xaa Arg Asn Gln Ile Pro Ile Tyr Asn Ala Asp His Glu Ile Thr Glu
            20                  25                  30

Ile Gln

<210> SEQ ID NO 205
<211> LENGTH: 34
<212> TYPE: PRT
<213> ORGANISM: Glycine
<220> FEATURE:
<223> OTHER INFORMATION: alternative Sequence of Glycine; X is not W
<220> FEATURE:
<221> NAME/KEY: SITE
<222> LOCATION: 17
<223> OTHER INFORMATION: X is not W

<400> SEQUENCE: 205

Phe Arg Lys Ser Arg Ser Gly Arg Leu Leu Leu Pro Pro Leu Glu Phe
1               5                   10                  15

Xaa Arg Asn Gln Ile Pro Ile Tyr Asn Ala Asp His Glu Ile Thr Glu
            20                  25                  30

Ile Arg

<210> SEQ ID NO 206
<211> LENGTH: 34
<212> TYPE: PRT
<213> ORGANISM: Phaseolus
<220> FEATURE:
<223> OTHER INFORMATION: X is not W
<220> FEATURE:
<221> NAME/KEY: SITE
<222> LOCATION: 17
<223> OTHER INFORMATION: X is not W

<400> SEQUENCE: 206

Phe Arg Thr Ser Arg Ser Gly Arg Met Leu Leu Pro Pro Leu Glu Phe
1               5                   10                  15

Xaa Arg Asn Gln Ile Pro Ile Tyr Asp Ala Asp His Glu Leu Lys Glu
            20                  25                  30

Ile Lys

-continued

```
<210> SEQ ID NO 207
<211> LENGTH: 34
<212> TYPE: PRT
<213> ORGANISM: Medicago
<220> FEATURE:
<223> OTHER INFORMATION: X is not W
<220> FEATURE:
<221> NAME/KEY: SITE
<222> LOCATION: 17
<223> OTHER INFORMATION: X is not W

<400> SEQUENCE: 207

Leu Lys Lys Ser Arg Ser Gly Arg Trp Leu Leu Pro Arg Leu Glu Phe
1               5                   10                  15

Xaa Arg Asn Gln Thr Pro Ile Tyr Asn Met Asp Arg Glu Ile Ile Glu
            20                  25                  30

Ile Gln

<210> SEQ ID NO 208
<211> LENGTH: 34
<212> TYPE: PRT
<213> ORGANISM: Medicago
<220> FEATURE:
<223> OTHER INFORMATION: X is not W
<220> FEATURE:
<221> NAME/KEY: SITE
<222> LOCATION: 17
<223> OTHER INFORMATION: X is not W

<400> SEQUENCE: 208

Leu Lys Lys Ser Arg Ser Gly Arg Trp Leu Leu Pro Pro Leu Glu Phe
1               5                   10                  15

Xaa Arg Asn Gln Gln Pro Ile Tyr Asn Met Asp Arg Glu Ile Thr Glu
            20                  25                  30

Ile Gln

<210> SEQ ID NO 209
<211> LENGTH: 34
<212> TYPE: PRT
<213> ORGANISM: Cicer
<220> FEATURE:
<223> OTHER INFORMATION: X is not W
<220> FEATURE:
<221> NAME/KEY: SITE
<222> LOCATION: 17
<223> OTHER INFORMATION: X is not W

<400> SEQUENCE: 209

Leu Lys Lys Ser Arg Ser Gly Arg Leu Leu Leu Pro Pro Leu Glu Phe
1               5                   10                  15

Xaa His Asn Gln Lys Pro Ile Tyr Asn Val Asp Arg Glu Ile Thr Glu
            20                  25                  30

Ile Gln

<210> SEQ ID NO 210
<211> LENGTH: 34
<212> TYPE: PRT
<213> ORGANISM: Citrus sinensis
<220> FEATURE:
<223> OTHER INFORMATION: X is not W
<220> FEATURE:
<221> NAME/KEY: SITE
<222> LOCATION: 17
<223> OTHER INFORMATION: X is not W

<400> SEQUENCE: 210
```

```
Leu Lys Arg Ser Arg Ser Gly Arg Leu Leu Val Pro Cys Leu Asp Phe
1               5                   10                  15

Xaa Arg Asn Gln Ile Ala Val Tyr Asp Ala Asp Arg Asn Ile Thr Gly
            20                  25                  30

Ile Gln

<210> SEQ ID NO 211
<211> LENGTH: 34
<212> TYPE: PRT
<213> ORGANISM: Vitis
<220> FEATURE:
<223> OTHER INFORMATION: X is not W
<220> FEATURE:
<221> NAME/KEY: SITE
<222> LOCATION: 17
<223> OTHER INFORMATION: X is not W

<400> SEQUENCE: 211

Leu Lys Arg Ser Arg Ser Gly Arg Leu Leu Pro Ser Leu Asp Phe
1               5                   10                  15

Xaa Arg Asn Gln Lys Ala Val Tyr Asp Ala Asp Arg Arg Ile Thr Gly
            20                  25                  30

Ile Gln

<210> SEQ ID NO 212
<211> LENGTH: 34
<212> TYPE: PRT
<213> ORGANISM: Theobroma
<220> FEATURE:
<223> OTHER INFORMATION: X is not W
<220> FEATURE:
<221> NAME/KEY: SITE
<222> LOCATION: 17
<223> OTHER INFORMATION: X is not W

<400> SEQUENCE: 212

Leu Lys Cys Ser Arg Ser Gly Arg Leu Leu Pro Arg Leu Glu Phe
1               5                   10                  15

Xaa Arg Asn Gln Ile Ala Val Tyr Asp Gln Thr Arg Lys Ile Thr Gly
            20                  25                  30

Ile Arg

<210> SEQ ID NO 213
<211> LENGTH: 34
<212> TYPE: PRT
<213> ORGANISM: Solanum
<220> FEATURE:
<223> OTHER INFORMATION: X is not W
<220> FEATURE:
<221> NAME/KEY: SITE
<222> LOCATION: 17
<223> OTHER INFORMATION: X is not W

<400> SEQUENCE: 213

Phe Asn Arg Ser Arg Ser Gly Arg Val Leu Pro Pro Met Ala Phe
1               5                   10                  15

Xaa Arg Asn Gln Arg Ala Val Tyr Asp Val Ile Leu Phe Thr Thr Gly
            20                  25                  30

Ile Ser

<210> SEQ ID NO 214
<211> LENGTH: 34
<212> TYPE: PRT
<213> ORGANISM: Populus
```

-continued

```
<220> FEATURE:
<223> OTHER INFORMATION: X is not W
<220> FEATURE:
<221> NAME/KEY: SITE
<222> LOCATION: 17
<223> OTHER INFORMATION: X is not W

<400> SEQUENCE: 214

Leu Lys Arg Ser Arg Ser Gly Arg Leu Leu Leu Pro Thr Leu Asp Phe
1               5                   10                  15

Xaa Arg Asn Gln Ile Pro Val Tyr Asp Glu Val Ser Gly Ile Ser Gly
            20                  25                  30

Ile Phe

<210> SEQ ID NO 215
<211> LENGTH: 34
<212> TYPE: PRT
<213> ORGANISM: Fragaria
<220> FEATURE:
<223> OTHER INFORMATION: X is not W
<220> FEATURE:
<221> NAME/KEY: SITE
<222> LOCATION: 17
<223> OTHER INFORMATION: X is not W

<400> SEQUENCE: 215

Thr Gly Arg Ser Arg Ser Gly Arg Leu Leu Leu Arg Pro Leu Glu Phe
1               5                   10                  15

Xaa Arg Asn Gln Ser Pro Val Tyr Asp Lys Asp His Gly Val Ile Gly
            20                  25                  30

Ile Gln

<210> SEQ ID NO 216
<211> LENGTH: 34
<212> TYPE: PRT
<213> ORGANISM: Fragaria
<220> FEATURE:
<223> OTHER INFORMATION: X is not W
<220> FEATURE:
<221> NAME/KEY: SITE
<222> LOCATION: 17
<223> OTHER INFORMATION: X is not W

<400> SEQUENCE: 216

Ala Gly Arg Ser Arg Ser Gly Arg Leu Arg Leu Arg Pro Leu Glu Phe
1               5                   10                  15

Xaa Arg Asn Gln Ser Ala Val Tyr Asp Lys Asp His Gly Val Ile Gly
            20                  25                  30

Ile Gln

<210> SEQ ID NO 217
<211> LENGTH: 34
<212> TYPE: PRT
<213> ORGANISM: Amborella
<220> FEATURE:
<223> OTHER INFORMATION: X is not W
<220> FEATURE:
<221> NAME/KEY: SITE
<222> LOCATION: 17
<223> OTHER INFORMATION: X is not W

<400> SEQUENCE: 217

Leu Ser Ile Ser Arg Ser Gly Arg Ile Ile Val Arg Pro Leu Ala Tyr
1               5                   10                  15

Xaa Cys Asn Glu Arg Ile Val Tyr Gly Lys Asp Gly Ser Ile Thr Ser
```

```
            20                  25                  30

Ile Leu

<210> SEQ ID NO 218
<211> LENGTH: 34
<212> TYPE: PRT
<213> ORGANISM: Brachypodium
<220> FEATURE:
<223> OTHER INFORMATION: X is not G
<220> FEATURE:
<221> NAME/KEY: SITE
<222> LOCATION: 17
<223> OTHER INFORMATION: X is not G

<400> SEQUENCE: 218

Met Thr Arg Thr Lys Ser Gly Arg Val Val Pro Pro Leu Asp Leu
1               5                   10                  15

Xaa Cys Glu Arg Ile Leu Tyr Gly Asn Asn His Leu Val Leu Gly Val
            20                  25                  30

Ala Pro

<210> SEQ ID NO 219
<211> LENGTH: 34
<212> TYPE: PRT
<213> ORGANISM: Oryza
<220> FEATURE:
<223> OTHER INFORMATION: X is not G
<220> FEATURE:
<221> NAME/KEY: SITE
<222> LOCATION: 17
<223> OTHER INFORMATION: X is not G

<400> SEQUENCE: 219

Leu Arg Arg Thr Arg Ser Gly Arg Val Val Pro Thr Leu Asp Pro
1               5                   10                  15

Xaa Cys Gln Arg Ile Val Tyr Asp Arg Asp Gly Leu Val Ser Gly Val
            20                  25                  30

Ala Gly

<210> SEQ ID NO 220
<211> LENGTH: 34
<212> TYPE: PRT
<213> ORGANISM: Setaria <grass>
<220> FEATURE:
<223> OTHER INFORMATION: X is not G
<220> FEATURE:
<221> NAME/KEY: SITE
<222> LOCATION: 17
<223> OTHER INFORMATION: X is not G

<400> SEQUENCE: 220

Leu Arg Lys Thr Arg Ser Gly Arg Val Val Pro Thr Leu Asp Lys
1               5                   10                  15

Xaa Cys Gln Arg Ile Val Tyr Asp Met Asp Gly Ala Ile Val Gly Val
            20                  25                  30

Val Gly

<210> SEQ ID NO 221
<211> LENGTH: 34
<212> TYPE: PRT
<213> ORGANISM: Sorghum <genus>
<220> FEATURE:
<223> OTHER INFORMATION: X is not W
<220> FEATURE:
<221> NAME/KEY: SITE
```

-continued

<222> LOCATION: 17
<223> OTHER INFORMATION: X is not W

<400> SEQUENCE: 221

Leu Lys Arg Ser Arg Ser Gly Arg Val Ile Val Pro Lys Leu Asp Asn
1               5                   10                  15

Xaa Cys Gln Thr Ile Val Tyr Gly Arg Asp Gly Leu Ile Ala Ala Val
            20                  25                  30

Ile Gly

<210> SEQ ID NO 222
<211> LENGTH: 33
<212> TYPE: PRT
<213> ORGANISM: Musa
<220> FEATURE:
<223> OTHER INFORMATION: X is not G
<220> FEATURE:
<221> NAME/KEY: SITE
<222> LOCATION: 17
<223> OTHER INFORMATION: X is not G

<400> SEQUENCE: 222

Phe Arg Arg Ser Arg Ser Gly Arg Leu Ile Val Pro Pro Leu Asp Asn
1               5                   10                  15

Xaa Cys Gln Gln Ile Ile Tyr Asp Ala Asp Gly Ser Ile Thr Gly Ile
            20                  25                  30

Met

<210> SEQ ID NO 223
<211> LENGTH: 34
<212> TYPE: PRT
<213> ORGANISM: Elaeis
<220> FEATURE:
<223> OTHER INFORMATION: X is not W
<220> FEATURE:
<221> NAME/KEY: SITE
<222> LOCATION: 17
<223> OTHER INFORMATION: X is not W

<400> SEQUENCE: 223

Leu Lys Arg Ser Arg Ser Gly Arg Leu Ile Val Pro Pro Leu Ala Asn
1               5                   10                  15

Xaa Cys Gln Gln Ile Ile Tyr Asp Ala Asp Gly Ser Ile Ala Gly Ile
            20                  25                  30

Arg Gly

<210> SEQ ID NO 224
<211> LENGTH: 34
<212> TYPE: PRT
<213> ORGANISM: Phoenix
<220> FEATURE:
<223> OTHER INFORMATION: X is not W
<220> FEATURE:
<221> NAME/KEY: SITE
<222> LOCATION: 17
<223> OTHER INFORMATION: X is not W

<400> SEQUENCE: 224

Leu Lys Arg Ser Arg Ser Gly Arg Leu Ile Val Pro Pro Leu Ala Asn
1               5                   10                  15

Xaa Cys Gln Gln Ile Ile Tyr Asn Ala Asp Gly Ser Ile Ala Gly Ile
            20                  25                  30

Arg Gly

```
<210> SEQ ID NO 225
<211> LENGTH: 34
<212> TYPE: PRT
<213> ORGANISM: Camelina
<220> FEATURE:
<223> OTHER INFORMATION: X is not W
<220> FEATURE:
<221> NAME/KEY: SITE
<222> LOCATION: 17
<223> OTHER INFORMATION: X is not W

<400> SEQUENCE: 225

Gln Lys Arg Ser Arg Ser Gly Arg Val Leu Val Ser Ser Leu Glu Tyr
1               5                   10                  15

Xaa Arg Asn Gln Ile Pro Val Tyr Asp Met Glu Arg Arg Leu Ile Glu
            20                  25                  30

Val Lys

<210> SEQ ID NO 226
<211> LENGTH: 33
<212> TYPE: PRT
<213> ORGANISM: Brassica
<220> FEATURE:
<223> OTHER INFORMATION: X is not W
<220> FEATURE:
<221> NAME/KEY: SITE
<222> LOCATION: 17
<223> OTHER INFORMATION: X is not W

<400> SEQUENCE: 226

Gln Lys Arg Ser Arg Ser Gly Arg Val Leu Val Ser Pro Leu Glu Tyr
1               5                   10                  15

Xaa Arg Asn Gln Leu Pro Val Tyr Asp Lys Asp Arg Asn Leu Ile Gln
            20                  25                  30

Val

<210> SEQ ID NO 227
<211> LENGTH: 33
<212> TYPE: PRT
<213> ORGANISM: Vigna
<220> FEATURE:
<223> OTHER INFORMATION: X is not W
<220> FEATURE:
<221> NAME/KEY: SITE
<222> LOCATION: 16
<223> OTHER INFORMATION: X is not W

<400> SEQUENCE: 227

Arg Thr Ser Arg Ser Gly Arg Leu Leu Val Pro Pro Leu Glu Phe Xaa
1               5                   10                  15

Arg Asn Gln Ile Pro Ile Tyr Asp Ala Asp His Val Leu Lys Glu Ile
            20                  25                  30

Lys

<210> SEQ ID NO 228
<211> LENGTH: 33
<212> TYPE: PRT
<213> ORGANISM: Daucus
<220> FEATURE:
<223> OTHER INFORMATION: X is not W
<220> FEATURE:
<221> NAME/KEY: SITE
<222> LOCATION: 16
<223> OTHER INFORMATION: X is not W

<400> SEQUENCE: 228
```

```
Lys Arg Ser Arg Ser Gly Arg Ile Leu Leu Pro Thr Leu Glu Tyr Xaa
1               5                   10                  15

Arg Asn Gln Thr Ala Ile Tyr Asp Ala Glu His Gln Val Ile Gly Ile
            20                  25                  30

Lys
```

<210> SEQ ID NO 229
<211> LENGTH: 33
<212> TYPE: PRT
<213> ORGANISM: Ziziphus
<220> FEATURE:
<223> OTHER INFORMATION: X is not W
<220> FEATURE:
<221> NAME/KEY: SITE
<222> LOCATION: 16
<223> OTHER INFORMATION: X is not W

<400> SEQUENCE: 229

```
Lys Arg Ser Arg Ser Gly Arg Leu Leu Leu Pro Thr Leu Glu Phe Xaa
1               5                   10                  15

Arg Asn Gln Met Pro Ile Tyr Asp Ala Asp His Lys Leu Ile Gly Ile
            20                  25                  30

Gln
```

<210> SEQ ID NO 230
<211> LENGTH: 33
<212> TYPE: PRT
<213> ORGANISM: Coffea
<220> FEATURE:
<223> OTHER INFORMATION: X is not W
<220> FEATURE:
<221> NAME/KEY: SITE
<222> LOCATION: 16
<223> OTHER INFORMATION: X is not W

<400> SEQUENCE: 230

```
Gln Arg Ser Arg Ser Gly Arg Leu Leu Leu Pro Thr Met Gln Phe Xaa
1               5                   10                  15

Arg Asn Gln Arg Ala Val Tyr Asp Ala Asp Arg Arg Ile Met Gly Ile
            20                  25                  30

Lys
```

<210> SEQ ID NO 231
<211> LENGTH: 33
<212> TYPE: PRT
<213> ORGANISM: Malus
<220> FEATURE:
<223> OTHER INFORMATION: X is not W
<220> FEATURE:
<221> NAME/KEY: SITE
<222> LOCATION: 16
<223> OTHER INFORMATION: X is not W

<400> SEQUENCE: 231

```
Lys Arg Ser Arg Thr Gly Arg Leu Leu Leu Pro Thr Met Glu Phe Xaa
1               5                   10                  15

Arg Asn Gln Ala Ala Val Tyr Asp Leu Asp Arg Asn Ile Thr Gly Ile
            20                  25                  30

Gln
```

<210> SEQ ID NO 232
<211> LENGTH: 33
<212> TYPE: PRT

```
<213> ORGANISM: Pyrus
<220> FEATURE:
<223> OTHER INFORMATION: X is not W
<220> FEATURE:
<221> NAME/KEY: SITE
<222> LOCATION: 16
<223> OTHER INFORMATION: X is not W

<400> SEQUENCE: 232

Lys Arg Ser Arg Thr Gly Arg Leu Leu Pro Thr Met Glu Phe Xaa
1               5                   10                  15

Arg Asn Gln Ala Ala Val Tyr Asp Leu Asp Arg Asn Ile Thr Gly Ile
            20                  25                  30

Gln

<210> SEQ ID NO 233
<211> LENGTH: 33
<212> TYPE: PRT
<213> ORGANISM: Ricinus <angiosperm>
<220> FEATURE:
<223> OTHER INFORMATION: X is not W
<220> FEATURE:
<221> NAME/KEY: SITE
<222> LOCATION: 16
<223> OTHER INFORMATION: X is not W

<400> SEQUENCE: 233

Lys Arg Ser Arg Ser Gly Arg Leu Leu Pro Thr Leu Asp Phe Xaa
1               5                   10                  15

Arg Asn Gln Ile Pro Val Tyr Asp Ala Asp Arg Asn Ile Thr Gly Ile
            20                  25                  30

Gln

<210> SEQ ID NO 234
<211> LENGTH: 33
<212> TYPE: PRT
<213> ORGANISM: Nicotiana
<220> FEATURE:
<223> OTHER INFORMATION: X is not W
<220> FEATURE:
<221> NAME/KEY: SITE
<222> LOCATION: 16
<223> OTHER INFORMATION: X is not W

<400> SEQUENCE: 234

Lys Arg Ser Arg Ser Gly Arg Leu Leu Leu Pro Pro Met Glu Phe Xaa
1               5                   10                  15

Arg Asn Gln Met Ala Ile Tyr Asp Ala Asp Arg Arg Val Thr Ala Ile
            20                  25                  30

Lys

<210> SEQ ID NO 235
<211> LENGTH: 33
<212> TYPE: PRT
<213> ORGANISM: Gossypium
<220> FEATURE:
<223> OTHER INFORMATION: X is not W
<220> FEATURE:
<221> NAME/KEY: SITE
<222> LOCATION: 16
<223> OTHER INFORMATION: X is not W

<400> SEQUENCE: 235

Lys Arg Ser Arg Ser Gly Arg Val Leu Leu Pro Arg Met Glu Phe Xaa
1               5                   10                  15
```

```
Arg Asn Gln Ile Pro Val Tyr Asp Gln Asp Arg Arg Ile Thr Gly Ile
            20                  25                  30
Lys

<210> SEQ ID NO 236
<211> LENGTH: 33
<212> TYPE: PRT
<213> ORGANISM: Prunus
<220> FEATURE:
<223> OTHER INFORMATION: X is not W
<220> FEATURE:
<221> NAME/KEY: SITE
<222> LOCATION: 16
<223> OTHER INFORMATION: X is not W

<400> SEQUENCE: 236

Arg Arg Ser Arg Ser Gly Arg Leu Leu Leu Pro Thr Met Glu Phe Xaa
1               5                   10                  15

Arg Asn Gln Leu Ala Ile Tyr Asp Ser Asp Arg Lys Val Thr Gly Ile
            20                  25                  30

Gln

<210> SEQ ID NO 237
<211> LENGTH: 28
<212> TYPE: PRT
<213> ORGANISM: Cucumis
<220> FEATURE:
<223> OTHER INFORMATION: X is not W
<220> FEATURE:
<221> NAME/KEY: SITE
<222> LOCATION: 15
<223> OTHER INFORMATION: X is not W

<400> SEQUENCE: 237

Arg Ser Arg Ser Gly Arg Val Leu Leu Pro Thr Met Glu Phe Xaa Arg
1               5                   10                  15

Asn Gln Leu Pro Val Tyr Asp Ser Asp Arg Lys Leu
            20                  25

<210> SEQ ID NO 238
<211> LENGTH: 34
<212> TYPE: PRT
<213> ORGANISM: Arabidopsis thaliana
<220> FEATURE:
<223> OTHER INFORMATION: X on position 8 is not R and X on position 17
      is not W
<220> FEATURE:
<221> NAME/KEY: SITE
<222> LOCATION: 8
<223> OTHER INFORMATION: X on position 8 is not R
<220> FEATURE:
<221> NAME/KEY: SITE
<222> LOCATION: 17
<223> OTHER INFORMATION: X on position 17 is not W

<400> SEQUENCE: 238

Gln Lys Arg Ser Arg Ser Gly Xaa Val Leu Val Ser Ser Leu Glu Phe
1               5                   10                  15

Xaa Arg Asn Gln Ile Pro Val Tyr Asp Met Asp Arg Asn Leu Ile Gln
            20                  25                  30

Val Lys

<210> SEQ ID NO 239
<211> LENGTH: 34
<212> TYPE: PRT
<213> ORGANISM: Arabidopsis lyrata
```

```
<220> FEATURE:
<223> OTHER INFORMATION: X on position 8 is not R and X on position 17
      is not W
<220> FEATURE:
<221> NAME/KEY: SITE
<222> LOCATION: 8
<223> OTHER INFORMATION: X on position 8 is not R
<220> FEATURE:
<221> NAME/KEY: SITE
<222> LOCATION: 17
<223> OTHER INFORMATION: X on position 17 is not W

<400> SEQUENCE: 239

Gln Lys Arg Ser Arg Ser Gly Xaa Val Leu Val Ser Ser Leu Glu Phe
1               5                   10                  15

Xaa Arg Asn Gln Ile Pro Val Tyr Asp Met Asp Arg Asn Leu Ile Gln
            20                  25                  30

Val Lys

<210> SEQ ID NO 240
<211> LENGTH: 34
<212> TYPE: PRT
<213> ORGANISM: Capsella
<220> FEATURE:
<223> OTHER INFORMATION: X on position 8 is not R and X on position 17
      is not W
<220> FEATURE:
<221> NAME/KEY: SITE
<222> LOCATION: 8
<223> OTHER INFORMATION: X on position 8 is not R
<220> FEATURE:
<221> NAME/KEY: SITE
<222> LOCATION: 17
<223> OTHER INFORMATION: X on position 17 is not W

<400> SEQUENCE: 240

Gln Lys Arg Ser Arg Ser Gly Xaa Val Leu Val Ser Pro Leu Glu Phe
1               5                   10                  15

Xaa Arg Asn Gln Ile Pro Val Tyr Asp Met Asp Arg Asn Leu Ile Gln
            20                  25                  30

Val Lys

<210> SEQ ID NO 241
<211> LENGTH: 34
<212> TYPE: PRT
<213> ORGANISM: Glycine
<220> FEATURE:
<223> OTHER INFORMATION: X on position 8 is not R and X on position 17
      is not W
<220> FEATURE:
<221> NAME/KEY: SITE
<222> LOCATION: 8
<223> OTHER INFORMATION: X on position 8 is not R
<220> FEATURE:
<221> NAME/KEY: SITE
<222> LOCATION: 17
<223> OTHER INFORMATION: X on position 17 is not W

<400> SEQUENCE: 241

Phe Arg Lys Ser Arg Ser Gly Xaa Leu Leu Leu Pro Pro Leu Glu Phe
1               5                   10                  15

Xaa Arg Asn Gln Ile Pro Ile Tyr Asn Ala Asp His Glu Ile Thr Glu
            20                  25                  30

Ile Gln

<210> SEQ ID NO 242
<211> LENGTH: 34
```

```
<212> TYPE: PRT
<213> ORGANISM: Glycine
<220> FEATURE:
<223> OTHER INFORMATION: alternative Sequence of Glycine; X on position
      8 is not R and X on position 17 is not W
<220> FEATURE:
<221> NAME/KEY: SITE
<222> LOCATION: 8
<223> OTHER INFORMATION: X on position 8 is not R
<220> FEATURE:
<221> NAME/KEY: SITE
<222> LOCATION: 17
<223> OTHER INFORMATION: X on position 17 is not W

<400> SEQUENCE: 242

Phe Arg Lys Ser Arg Ser Gly Xaa Leu Leu Leu Pro Pro Leu Glu Phe
1               5                   10                  15

Xaa Arg Asn Gln Ile Pro Ile Tyr Asn Ala Asp His Glu Ile Thr Glu
            20                  25                  30

Ile Arg

<210> SEQ ID NO 243
<211> LENGTH: 34
<212> TYPE: PRT
<213> ORGANISM: Phaseolus
<220> FEATURE:
<223> OTHER INFORMATION: X on position 8 is not R and X on position 17
      is not W
<220> FEATURE:
<221> NAME/KEY: SITE
<222> LOCATION: 8
<223> OTHER INFORMATION: X on position 8 is not R
<220> FEATURE:
<221> NAME/KEY: SITE
<222> LOCATION: 17
<223> OTHER INFORMATION: X on position 17 is not W

<400> SEQUENCE: 243

Phe Arg Thr Ser Arg Ser Gly Xaa Met Leu Leu Pro Pro Leu Glu Phe
1               5                   10                  15

Xaa Arg Asn Gln Ile Pro Ile Tyr Asp Ala Asp His Glu Leu Lys Glu
            20                  25                  30

Ile Lys

<210> SEQ ID NO 244
<211> LENGTH: 34
<212> TYPE: PRT
<213> ORGANISM: Medicago
<220> FEATURE:
<223> OTHER INFORMATION: X on position 8 is not R and X on position 17
      is not W
<220> FEATURE:
<221> NAME/KEY: SITE
<222> LOCATION: 8
<223> OTHER INFORMATION: X on position 8 is not R
<220> FEATURE:
<221> NAME/KEY: SITE
<222> LOCATION: 17
<223> OTHER INFORMATION: X on position 17 is not W

<400> SEQUENCE: 244

Leu Lys Lys Ser Arg Ser Gly Xaa Trp Leu Leu Pro Arg Leu Glu Phe
1               5                   10                  15

Xaa Arg Asn Gln Thr Pro Ile Tyr Asn Met Asp Arg Glu Ile Ile Glu
            20                  25                  30

Ile Gln
```

```
<210> SEQ ID NO 245
<211> LENGTH: 34
<212> TYPE: PRT
<213> ORGANISM: Medicago
<220> FEATURE:
<223> OTHER INFORMATION: X on position 8 is not R and X on position 17
      is not W
<220> FEATURE:
<221> NAME/KEY: SITE
<222> LOCATION: 8
<223> OTHER INFORMATION: X on position 8 is not R
<220> FEATURE:
<221> NAME/KEY: SITE
<222> LOCATION: 17
<223> OTHER INFORMATION: X on position 17 is not W

<400> SEQUENCE: 245

Leu Lys Lys Ser Arg Ser Gly Xaa Trp Leu Leu Pro Pro Leu Glu Phe
1               5                   10                  15

Xaa Arg Asn Gln Gln Pro Ile Tyr Asn Met Asp Arg Glu Ile Thr Glu
            20                  25                  30

Ile Gln

<210> SEQ ID NO 246
<211> LENGTH: 34
<212> TYPE: PRT
<213> ORGANISM: Cicer
<220> FEATURE:
<223> OTHER INFORMATION: X on position 8 is not R and X on position 17
      is not W
<220> FEATURE:
<221> NAME/KEY: SITE
<222> LOCATION: 8
<223> OTHER INFORMATION: X on position 8 is not R
<220> FEATURE:
<221> NAME/KEY: SITE
<222> LOCATION: 17
<223> OTHER INFORMATION: X on position 17 is not W

<400> SEQUENCE: 246

Leu Lys Lys Ser Arg Ser Gly Xaa Leu Leu Leu Pro Pro Leu Glu Phe
1               5                   10                  15

Xaa His Asn Gln Lys Pro Ile Tyr Asn Val Asp Arg Glu Ile Thr Glu
            20                  25                  30

Ile Gln

<210> SEQ ID NO 247
<211> LENGTH: 34
<212> TYPE: PRT
<213> ORGANISM: Citrus sinensis
<220> FEATURE:
<223> OTHER INFORMATION: X on position 8 is not R and X on position 17
      is not W
<220> FEATURE:
<221> NAME/KEY: SITE
<222> LOCATION: 8
<223> OTHER INFORMATION: X on position 8 is not R
<220> FEATURE:
<221> NAME/KEY: SITE
<222> LOCATION: 17
<223> OTHER INFORMATION: X on position 17 is not W

<400> SEQUENCE: 247

Leu Lys Arg Ser Arg Ser Gly Xaa Leu Leu Val Pro Cys Leu Asp Phe
1               5                   10                  15

Xaa Arg Asn Gln Ile Ala Val Tyr Asp Ala Asp Arg Asn Ile Thr Gly
            20                  25                  30

Ile Gln
```

<210> SEQ ID NO 248
<211> LENGTH: 34
<212> TYPE: PRT
<213> ORGANISM: Vitis
<220> FEATURE:
<223> OTHER INFORMATION: X on position 8 is not R and X on position 17
     is not W
<220> FEATURE:
<221> NAME/KEY: SITE
<222> LOCATION: 8
<223> OTHER INFORMATION: X on position 8 is not R
<220> FEATURE:
<221> NAME/KEY: SITE
<222> LOCATION: 17
<223> OTHER INFORMATION: X on position 17 is not W

<400> SEQUENCE: 248

Leu Lys Arg Ser Arg Ser Gly Xaa Leu Leu Leu Pro Ser Leu Asp Phe
1               5                   10                  15

Xaa Arg Asn Gln Lys Ala Val Tyr Asp Ala Asp Arg Arg Ile Thr Gly
            20                  25                  30

Ile Gln

<210> SEQ ID NO 249
<211> LENGTH: 34
<212> TYPE: PRT
<213> ORGANISM: Theobroma
<220> FEATURE:
<223> OTHER INFORMATION: X on position 8 is not R and X on position 17
     is not W
<220> FEATURE:
<221> NAME/KEY: SITE
<222> LOCATION: 8
<223> OTHER INFORMATION: X on position 8 is not R
<220> FEATURE:
<221> NAME/KEY: SITE
<222> LOCATION: 17
<223> OTHER INFORMATION: X on position 17 is not W

<400> SEQUENCE: 249

Leu Lys Cys Ser Arg Ser Gly Xaa Leu Leu Leu Pro Arg Leu Glu Phe
1               5                   10                  15

Xaa Arg Asn Gln Ile Ala Val Tyr Asp Gln Thr Arg Lys Ile Thr Gly
            20                  25                  30

Ile Arg

<210> SEQ ID NO 250
<211> LENGTH: 34
<212> TYPE: PRT
<213> ORGANISM: Solanum
<220> FEATURE:
<223> OTHER INFORMATION: X on position 8 is not R and X on position 17
     is not W
<220> FEATURE:
<221> NAME/KEY: SITE
<222> LOCATION: 8
<223> OTHER INFORMATION: X on position 8 is not R
<220> FEATURE:
<221> NAME/KEY: SITE
<222> LOCATION: 17
<223> OTHER INFORMATION: X on position 17 is not W

<400> SEQUENCE: 250

Phe Asn Arg Ser Arg Ser Gly Xaa Val Leu Leu Pro Pro Met Ala Phe
1               5                   10                  15

Xaa Arg Asn Gln Arg Ala Val Tyr Asp Val Ile Leu Phe Thr Thr Gly
            20                  25                  30

Ile Ser

<210> SEQ ID NO 251
<211> LENGTH: 34
<212> TYPE: PRT
<213> ORGANISM: Populus
<220> FEATURE:
<223> OTHER INFORMATION: X on position 8 is not R and X on position 17
      is not W
<220> FEATURE:
<221> NAME/KEY: SITE
<222> LOCATION: 8
<223> OTHER INFORMATION: X on position 8 is not R
<220> FEATURE:
<221> NAME/KEY: SITE
<222> LOCATION: 17
<223> OTHER INFORMATION: X on position 17 is not W

<400> SEQUENCE: 251

Leu Lys Arg Ser Arg Ser Gly Xaa Leu Leu Leu Pro Thr Leu Asp Phe
1               5                   10                  15

Xaa Arg Asn Gln Ile Pro Val Tyr Asp Glu Val Ser Gly Ile Ser Gly
            20                  25                  30

Ile Phe

<210> SEQ ID NO 252
<211> LENGTH: 34
<212> TYPE: PRT
<213> ORGANISM: Fragaria
<220> FEATURE:
<223> OTHER INFORMATION: X on position 8 is not R and X on position 17
      is not W
<220> FEATURE:
<221> NAME/KEY: SITE
<222> LOCATION: 8
<223> OTHER INFORMATION: X on position 8 is not R
<220> FEATURE:
<221> NAME/KEY: SITE
<222> LOCATION: 17
<223> OTHER INFORMATION: X on position 17 is not W

<400> SEQUENCE: 252

Thr Gly Arg Ser Arg Ser Gly Xaa Leu Leu Leu Arg Pro Leu Glu Phe
1               5                   10                  15

Xaa Arg Asn Gln Ser Pro Val Tyr Asp Lys Asp His Gly Val Ile Gly
            20                  25                  30

Ile Gln

<210> SEQ ID NO 253
<211> LENGTH: 34
<212> TYPE: PRT
<213> ORGANISM: Fragaria
<220> FEATURE:
<223> OTHER INFORMATION: X on position 8 is not R and X on position 17
      is not W
<220> FEATURE:
<221> NAME/KEY: SITE
<222> LOCATION: 8
<223> OTHER INFORMATION: X on position 8 is not R
<220> FEATURE:
<221> NAME/KEY: SITE
<222> LOCATION: 17
<223> OTHER INFORMATION: X on position 17 is not W

<400> SEQUENCE: 253

Ala Gly Arg Ser Arg Ser Gly Xaa Leu Arg Leu Arg Pro Leu Glu Phe
1               5                   10                  15

```
Xaa Arg Asn Gln Ser Ala Val Tyr Asp Lys Asp His Gly Val Ile Gly
            20                  25                  30

Ile Gln

<210> SEQ ID NO 254
<211> LENGTH: 34
<212> TYPE: PRT
<213> ORGANISM: Amborella
<220> FEATURE:
<223> OTHER INFORMATION: X on position 8 is not R and X on position 17
      is not W
<220> FEATURE:
<221> NAME/KEY: SITE
<222> LOCATION: 8
<223> OTHER INFORMATION: X on position 8 is not R
<220> FEATURE:
<221> NAME/KEY: SITE
<222> LOCATION: 17
<223> OTHER INFORMATION: X on position 17 is not W

<400> SEQUENCE: 254

Leu Ser Ile Ser Arg Ser Gly Xaa Ile Ile Val Arg Pro Leu Ala Tyr
1               5                   10                  15

Xaa Cys Asn Glu Arg Ile Val Tyr Gly Lys Asp Gly Ser Ile Thr Ser
            20                  25                  30

Ile Leu

<210> SEQ ID NO 255
<211> LENGTH: 34
<212> TYPE: PRT
<213> ORGANISM: Brachypodium
<220> FEATURE:
<223> OTHER INFORMATION: X on position 8 is not R and X on position 17
      is not G
<220> FEATURE:
<221> NAME/KEY: SITE
<222> LOCATION: 8
<223> OTHER INFORMATION: X on position 8 is not R
<220> FEATURE:
<221> NAME/KEY: SITE
<222> LOCATION: 17
<223> OTHER INFORMATION: X on position 17 is not G

<400> SEQUENCE: 255

Met Thr Arg Thr Lys Ser Gly Xaa Val Val Val Pro Pro Leu Asp Leu
1               5                   10                  15

Xaa Cys Glu Arg Ile Leu Tyr Gly Asn Asn His Leu Val Leu Gly Val
            20                  25                  30

Ala Pro

<210> SEQ ID NO 256
<211> LENGTH: 34
<212> TYPE: PRT
<213> ORGANISM: Oryza
<220> FEATURE:
<223> OTHER INFORMATION: X on position 8 is not R and X on position 17
      is not G
<220> FEATURE:
<221> NAME/KEY: SITE
<222> LOCATION: 8
<223> OTHER INFORMATION: X on position 8 is not R
<220> FEATURE:
<221> NAME/KEY: SITE
<222> LOCATION: 17
<223> OTHER INFORMATION: X on position 17 is not G

<400> SEQUENCE: 256

Leu Arg Arg Thr Arg Ser Gly Xaa Val Val Val Pro Thr Leu Asp Pro
```

-continued

```
                1               5                  10                  15
Xaa Cys Gln Arg Ile Val Tyr Asp Arg Asp Gly Leu Val Ser Gly Val
            20                  25                  30

Ala Gly
```

<210> SEQ ID NO 257
<211> LENGTH: 34
<212> TYPE: PRT
<213> ORGANISM: Setaria <grass>
<220> FEATURE:
<223> OTHER INFORMATION: X on position 8 is not R and X on position 17
      is not G
<220> FEATURE:
<221> NAME/KEY: SITE
<222> LOCATION: 8
<223> OTHER INFORMATION: X on position 8 is not R
<220> FEATURE:
<221> NAME/KEY: SITE
<222> LOCATION: 17
<223> OTHER INFORMATION: X on position 17 is not G

<400> SEQUENCE: 257

```
Leu Arg Lys Thr Arg Ser Gly Xaa Val Val Val Pro Thr Leu Asp Lys
1               5                  10                  15

Xaa Cys Gln Arg Ile Val Tyr Asp Met Asp Gly Ala Ile Val Gly Val
            20                  25                  30

Val Gly
```

<210> SEQ ID NO 258
<211> LENGTH: 34
<212> TYPE: PRT
<213> ORGANISM: Sorghum <genus>
<220> FEATURE:
<223> OTHER INFORMATION: X on position 8 is not R and X on position 17
      is not W
<220> FEATURE:
<221> NAME/KEY: SITE
<222> LOCATION: 8
<223> OTHER INFORMATION: X on position 8 is not R
<220> FEATURE:
<221> NAME/KEY: SITE
<222> LOCATION: 17
<223> OTHER INFORMATION: X on position 17 is not W

<400> SEQUENCE: 258

```
Leu Lys Arg Ser Arg Ser Gly Xaa Val Ile Val Pro Lys Leu Asp Asn
1               5                  10                  15

Xaa Cys Gln Thr Ile Val Tyr Gly Arg Asp Gly Leu Ile Ala Ala Val
            20                  25                  30

Ile Gly
```

<210> SEQ ID NO 259
<211> LENGTH: 33
<212> TYPE: PRT
<213> ORGANISM: Musa
<220> FEATURE:
<223> OTHER INFORMATION: X on position 8 is not R and X on position 17
      is not G
<220> FEATURE:
<221> NAME/KEY: SITE
<222> LOCATION: 8
<223> OTHER INFORMATION: X on position 8 is not R
<220> FEATURE:
<221> NAME/KEY: SITE
<222> LOCATION: 17
<223> OTHER INFORMATION: X on position 17 is not G

<400> SEQUENCE: 259

Phe Arg Arg Ser Arg Ser Gly Xaa Leu Ile Val Pro Pro Leu Asp Asn
1               5                   10                  15

Xaa Cys Gln Gln Ile Ile Tyr Asp Ala Asp Gly Ser Ile Thr Gly Ile
            20                  25                  30

Met

<210> SEQ ID NO 260
<211> LENGTH: 34
<212> TYPE: PRT
<213> ORGANISM: Elaeis
<220> FEATURE:
<223> OTHER INFORMATION: X on position 8 is not R and X on position 17
      is not W
<220> FEATURE:
<221> NAME/KEY: SITE
<222> LOCATION: 8
<223> OTHER INFORMATION: X on position 8 is not R
<220> FEATURE:
<221> NAME/KEY: SITE
<222> LOCATION: 17
<223> OTHER INFORMATION: X on position 17 is not W

<400> SEQUENCE: 260

Leu Lys Arg Ser Arg Ser Gly Xaa Leu Ile Val Pro Pro Leu Ala Asn
1               5                   10                  15

Xaa Cys Gln Gln Ile Ile Tyr Asp Ala Asp Gly Ser Ile Ala Gly Ile
            20                  25                  30

Arg Gly

<210> SEQ ID NO 261
<211> LENGTH: 34
<212> TYPE: PRT
<213> ORGANISM: Phoenix
<220> FEATURE:
<223> OTHER INFORMATION: X on position 8 is not R and X on position 17
      is not W
<220> FEATURE:
<221> NAME/KEY: SITE
<222> LOCATION: 8
<223> OTHER INFORMATION: X on position 8 is not R
<220> FEATURE:
<221> NAME/KEY: SITE
<222> LOCATION: 17
<223> OTHER INFORMATION: X on position 17 is not W

<400> SEQUENCE: 261

Leu Lys Arg Ser Arg Ser Gly Xaa Leu Ile Val Pro Pro Leu Ala Asn
1               5                   10                  15

Xaa Cys Gln Gln Ile Ile Tyr Asn Ala Asp Gly Ser Ile Ala Gly Ile
            20                  25                  30

Arg Gly

<210> SEQ ID NO 262
<211> LENGTH: 34
<212> TYPE: PRT
<213> ORGANISM: Camelina
<220> FEATURE:
<223> OTHER INFORMATION: X on position 8 is not R and X on position 17
      is not W
<220> FEATURE:
<221> NAME/KEY: SITE
<222> LOCATION: 8
<223> OTHER INFORMATION: X on position 8 is not R
<220> FEATURE:
<221> NAME/KEY: SITE
<222> LOCATION: 17
<223> OTHER INFORMATION: X on position 17 is not W -continued

<400> SEQUENCE: 262

Gln Lys Arg Ser Arg Ser Gly Xaa Val Leu Val Ser Ser Leu Glu Tyr
1               5                   10                  15

Xaa Arg Asn Gln Ile Pro Val Tyr Asp Met Glu Arg Arg Leu Ile Glu
                20                  25                  30

Val Lys

<210> SEQ ID NO 263
<211> LENGTH: 33
<212> TYPE: PRT
<213> ORGANISM: Brassica
<220> FEATURE:
<223> OTHER INFORMATION: X on position 8 is not R and X on position 17
      is not W
<220> FEATURE:
<221> NAME/KEY: SITE
<222> LOCATION: 8
<223> OTHER INFORMATION: X on position 8 is not R
<220> FEATURE:
<221> NAME/KEY: SITE
<222> LOCATION: 17
<223> OTHER INFORMATION: X on position 17 is not W

<400> SEQUENCE: 263

Gln Lys Arg Ser Arg Ser Gly Xaa Val Leu Val Ser Pro Leu Glu Tyr
1               5                   10                  15

Xaa Arg Asn Gln Leu Pro Val Tyr Asp Lys Asp Arg Asn Leu Ile Gln
                20                  25                  30

Val

<210> SEQ ID NO 264
<211> LENGTH: 33
<212> TYPE: PRT
<213> ORGANISM: Vigna
<220> FEATURE:
<223> OTHER INFORMATION: X on position 7 is not R and X on position 16
      is not W
<220> FEATURE:
<221> NAME/KEY: SITE
<222> LOCATION: 7
<223> OTHER INFORMATION: X on position 7 is not R
<220> FEATURE:
<221> NAME/KEY: SITE
<222> LOCATION: 16
<223> OTHER INFORMATION: X on position 16 is not W

<400> SEQUENCE: 264

Arg Thr Ser Arg Ser Gly Xaa Leu Leu Val Pro Pro Leu Glu Phe Xaa
1               5                   10                  15

Arg Asn Gln Ile Pro Ile Tyr Asp Ala Asp His Val Leu Lys Glu Ile
                20                  25                  30

Lys

<210> SEQ ID NO 265
<211> LENGTH: 33
<212> TYPE: PRT
<213> ORGANISM: Daucus
<220> FEATURE:
<223> OTHER INFORMATION: X on position 7 is not R and X on position 16
      is not W
<220> FEATURE:
<221> NAME/KEY: SITE
<222> LOCATION: 7
<223> OTHER INFORMATION: X on position 7 is not R
<220> FEATURE:
<221> NAME/KEY: SITE
<222> LOCATION: 16
<223> OTHER INFORMATION: X on position 16 is not W

<400> SEQUENCE: 265

Lys Arg Ser Arg Ser Gly Xaa Ile Leu Leu Pro Thr Leu Glu Tyr Xaa
1               5                   10                  15

Arg Asn Gln Thr Ala Ile Tyr Asp Ala Glu His Gln Val Ile Gly Ile
            20                  25                  30

Lys

<210> SEQ ID NO 266
<211> LENGTH: 33
<212> TYPE: PRT
<213> ORGANISM: Ziziphus
<220> FEATURE:
<223> OTHER INFORMATION: X on position 7 is not R and X on position 16
      is not W
<220> FEATURE:
<221> NAME/KEY: SITE
<222> LOCATION: 7
<223> OTHER INFORMATION: X on position 7 is not R
<220> FEATURE:
<221> NAME/KEY: SITE
<222> LOCATION: 16
<223> OTHER INFORMATION: X on position 16 is not W

<400> SEQUENCE: 266

Lys Arg Ser Arg Ser Gly Xaa Leu Leu Leu Pro Thr Leu Glu Phe Xaa
1               5                   10                  15

Arg Asn Gln Met Pro Ile Tyr Asp Ala Asp His Lys Leu Ile Gly Ile
            20                  25                  30

Gln

<210> SEQ ID NO 267
<211> LENGTH: 33
<212> TYPE: PRT
<213> ORGANISM: Coffea
<220> FEATURE:
<223> OTHER INFORMATION: X on position 7 is not R and X on position 16
      is not W
<220> FEATURE:
<221> NAME/KEY: SITE
<222> LOCATION: 7
<223> OTHER INFORMATION: X on position 7 is not R
<220> FEATURE:
<221> NAME/KEY: SITE
<222> LOCATION: 16
<223> OTHER INFORMATION: X on position 16 is not W

<400> SEQUENCE: 267

Gln Arg Ser Arg Ser Gly Xaa Leu Leu Leu Pro Thr Met Gln Phe Xaa
1               5                   10                  15

Arg Asn Gln Arg Ala Val Tyr Asp Ala Asp Arg Arg Ile Met Gly Ile
            20                  25                  30

Lys

<210> SEQ ID NO 268
<211> LENGTH: 33
<212> TYPE: PRT
<213> ORGANISM: Malus
<220> FEATURE:
<223> OTHER INFORMATION: X on position 7 is not R and X on position 16
      is not W
<220> FEATURE:
<221> NAME/KEY: SITE
<222> LOCATION: 7
<223> OTHER INFORMATION: X on position 7 is not R

```
<220> FEATURE:
<221> NAME/KEY: SITE
<222> LOCATION: 16
<223> OTHER INFORMATION: X on position 16 is not W

<400> SEQUENCE: 268

Lys Arg Ser Arg Thr Gly Xaa Leu Leu Leu Pro Thr Met Glu Phe Xaa
1               5                   10                  15

Arg Asn Gln Ala Ala Val Tyr Asp Leu Asp Arg Asn Ile Thr Gly Ile
            20                  25                  30

Gln

<210> SEQ ID NO 269
<211> LENGTH: 33
<212> TYPE: PRT
<213> ORGANISM: Pyrus
<220> FEATURE:
<223> OTHER INFORMATION: X on position 7 is not R and X on position 16
      is not W
<220> FEATURE:
<221> NAME/KEY: SITE
<222> LOCATION: 7
<223> OTHER INFORMATION: X on position 7 is not R
<220> FEATURE:
<221> NAME/KEY: SITE
<222> LOCATION: 16
<223> OTHER INFORMATION: X on position 16 is not W

<400> SEQUENCE: 269

Lys Arg Ser Arg Thr Gly Xaa Leu Leu Leu Pro Thr Met Glu Phe Xaa
1               5                   10                  15

Arg Asn Gln Ala Ala Val Tyr Asp Leu Asp Arg Asn Ile Thr Gly Ile
            20                  25                  30

Gln

<210> SEQ ID NO 270
<211> LENGTH: 33
<212> TYPE: PRT
<213> ORGANISM: Ricinus <angiosperm>
<220> FEATURE:
<223> OTHER INFORMATION: X on position 7 is not R and X on position 16
      is not W
<220> FEATURE:
<221> NAME/KEY: SITE
<222> LOCATION: 7
<223> OTHER INFORMATION: X on position 7 is not R
<220> FEATURE:
<221> NAME/KEY: SITE
<222> LOCATION: 16
<223> OTHER INFORMATION: X on position 16 is not W

<400> SEQUENCE: 270

Lys Arg Ser Arg Ser Gly Xaa Leu Leu Leu Pro Thr Leu Asp Phe Xaa
1               5                   10                  15

Arg Asn Gln Ile Pro Val Tyr Asp Ala Asp Arg Asn Ile Thr Gly Ile
            20                  25                  30

Gln

<210> SEQ ID NO 271
<211> LENGTH: 33
<212> TYPE: PRT
<213> ORGANISM: Nicotiana
<220> FEATURE:
<223> OTHER INFORMATION: X on position 7 is not R and X on position 16
      is not W
<220> FEATURE:
<221> NAME/KEY: SITE
```

```
<222> LOCATION: 7
<223> OTHER INFORMATION: X on position 7 is not R
<220> FEATURE:
<221> NAME/KEY: SITE
<222> LOCATION: 16
<223> OTHER INFORMATION: X on position 16 is not W

<400> SEQUENCE: 271

Lys Arg Ser Arg Ser Gly Xaa Leu Leu Leu Pro Pro Met Glu Phe Xaa
1               5                   10                  15

Arg Asn Gln Met Ala Ile Tyr Asp Ala Asp Arg Arg Val Thr Ala Ile
            20                  25                  30

Lys

<210> SEQ ID NO 272
<211> LENGTH: 33
<212> TYPE: PRT
<213> ORGANISM: Gossypium
<220> FEATURE:
<223> OTHER INFORMATION: X on position 7 is not R and X on position 16
      is not W
<220> FEATURE:
<221> NAME/KEY: SITE
<222> LOCATION: 7
<223> OTHER INFORMATION: X on position 7 is not R
<220> FEATURE:
<221> NAME/KEY: SITE
<222> LOCATION: 16
<223> OTHER INFORMATION: X on position 16 is not W

<400> SEQUENCE: 272

Lys Arg Ser Arg Ser Gly Xaa Val Leu Leu Pro Arg Met Glu Phe Xaa
1               5                   10                  15

Arg Asn Gln Ile Pro Val Tyr Asp Gln Asp Arg Arg Ile Thr Gly Ile
            20                  25                  30

Lys

<210> SEQ ID NO 273
<211> LENGTH: 33
<212> TYPE: PRT
<213> ORGANISM: Prunus
<220> FEATURE:
<223> OTHER INFORMATION: X on position 7 is not R and X on position 16
      is not W
<220> FEATURE:
<221> NAME/KEY: SITE
<222> LOCATION: 7
<223> OTHER INFORMATION: X on position 7 is not R
<220> FEATURE:
<221> NAME/KEY: SITE
<222> LOCATION: 16
<223> OTHER INFORMATION: X on position 16 is not W

<400> SEQUENCE: 273

Arg Arg Ser Arg Ser Gly Xaa Leu Leu Leu Pro Thr Met Glu Phe Xaa
1               5                   10                  15

Arg Asn Gln Leu Ala Ile Tyr Asp Ser Asp Arg Lys Val Thr Gly Ile
            20                  25                  30

Gln

<210> SEQ ID NO 274
<211> LENGTH: 28
<212> TYPE: PRT
<213> ORGANISM: Cucumis
<220> FEATURE:
<223> OTHER INFORMATION: X on position 6 is not R and X on position 15
      is not W
```

```
<220> FEATURE:
<221> NAME/KEY: SITE
<222> LOCATION: 6
<223> OTHER INFORMATION: X on position 6 is not R
<220> FEATURE:
<221> NAME/KEY: SITE
<222> LOCATION: 15
<223> OTHER INFORMATION: X on position 15 is not W

<400> SEQUENCE: 274

Arg Ser Arg Ser Gly Xaa Val Leu Leu Pro Thr Met Glu Phe Xaa Arg
1               5                   10                  15

Asn Gln Leu Pro Val Tyr Asp Ser Asp Arg Lys Leu
            20                  25
```

GENERATION OF HAPOLOID PLANTS BASED ON KNL2

The present invention relates to non-transgenic and transgenic plants, preferably crop plants, comprising at least one mutation of the KINETOCHORE NULL2 (KNL2) protein, especially a mutation causing a substitution of an amino acid within the KNL2 protein, preferably within the C-terminal region of the KNL2 protein, which preferably have the biological activity of a haploid inducer. Further, the present invention provides methods of generating the plants of the present invention and haploid and double haploid plants obtainable by crossing the plants of the present invention with wildtype plants as well as methods of facilitating cytoplasm exchange.

The generation and use of haploids is one of the most powerful biotechnological means to improve cultivated plants. The advantage of haploids for breeders is that homozygosity can be achieved already in the first generation after dihaploidization, creating doubled haploid plants, without the need of several backcrossing generations required to obtain a high degree of homozygosity. Further, the value of haploids in plant research and breeding lies in the fact that the founder cells of doubled haploids are products of meiosis, so that resultant populations constitute pools of diverse recombinant and at the same time genetically fixed individuals. The generation of doubled haploids thus provides not only perfectly useful genetic variability to select from with regard to crop improvement, but is also a valuable means to produce mapping populations, recombinant inbreds as well as instantly homozygous mutants and transgenic lines.

Haploids can be obtained by in vitro or in vivo approaches. However, many species and genotypes are recalcitrant to these processes. Alternatively, substantial changes of the centromere-specific histone H3 variant (CENH3, also called CENP-A), by swapping its N-terminal regions and fusing it to GFP ("GFP-tailswap" CENH3), creates haploid inducer lines in the model plant *Arabidopsis thaliana* (Ravi and Chan, Nature, 464 (2010), 615-618 and US 2011/0083202 A1). Haploids induction methods based on CENH3-mediated approach requires the generation of cenh3 mutant with its subsequent complementation by altered CENH3 ("GFP tailswap" CENH3) variants. CENH3 proteins are variants of H3 histone proteins that are members of the kinetochore complex of active centromeres. With these "GFP-tailswap" haploid inducer lines, haploidization occurred in the progeny when a haploid inducer plant was crossed with a wildtype plant. Interestingly, the haploid inducer line was stable upon selfing, suggesting that a competition between modified and wild type centromere in the developing hybrid embryo results in centromere inactivation of the inducer parent and consequently in uniparental chromosome elimination. As a result, the chromosomes containing the altered CENH3 protein are lost during early embryo development producing haploid progeny containing only the chromosomes of the wildtype parent.

Thus, haploid plants can be obtained by crossing "GFP-tailswap" transgenic plants as haploid inducer to wildtype plants. However, as described above, this technique requires generation of cenh3 mutant and substitution of endogenous CENH3 by substantial changes of the CENH3 protein and the plants comprise a heterologous transgene, which is economically problematic because of increasing public reluctance toward genetically engineered crops.

However, using CENH3 has the disadvantage, that the cenh3 mutant is viable only in heterozygous state. Furthermore CENH3 is present in a relatively high number of isoforms, for example six isoforms in wheat and two isoforms in barley.

It is therefore an object of the present invention to overcome the aforementioned problems and in particular to provide alternative haploid inducer plants which do not comprise necessarily modifications of their CENH3 protein and/or which are not genetically engineered.

This problem is solved by the subject matter of the independent claims, in particular by a plant having preferably biological activity of a haploid inducer and comprising a nucleotide sequence encoding a KINETOCHORE NULL2 (KNL2) protein, wherein the nucleotide sequence comprises at least one mutation. Preferably the mutation causes an amino acid addition, deletion or substitution which confers the biological activity of a haploid inducer.

The mutation of the KNL2 protein can be at least one amino acid substitution, a deletion of at least one amino acid and/or the addition, i.e. insertion, of at least one amino acid. In a further embodiment the expression of the KNL2 protein is diminished or even suppressed in the plant.

In a preferred embodiment the KNL2 protein comprises a CENP-C like motif, wherein the mutation of the KNL2 protein is in the CENP-C like motif. The mutation can also be in the C-terminal or the N-terminal part of the protein. The invention also relates to the downregulation of the KNL2 protein in a plant to produce haploid plants.

In a preferred embodiment the KNL2 protein comprises a CENP-C like motif, wherein the nucleotide sequence comprises at least one mutation in the CENP-C like motif, preferably causing in the CENP-C like motif an amino acid deletion, addition, i.e. insertion, or substitution which confers the biological activity of a haploid inducer.

A CENP-C like motif is a motif which has a significant homology to the conserved CENP-C motif of the protein CENP-C, as described in (Kato et al, Science, 340 (2013), 1110-1113) and as shown for example in SEQ ID No. 2.

Preferably, the CENP-C like motif is a CENPC-k motif.

The invention refers especially to a plant, wherein the plant comprises a nucleotide sequence encoding a KINETOCHORE NULL2 (KNL2) protein comprising a CENPC-k motif, wherein the nucleotide sequence comprises at least one mutation in the CENPC-k motif encoding sequence.

Preferably the at least one mutation is a deletion, addition or substitution of at least one nucleotide in the nucleotide sequence for the CENPC-k motif. Preferably the plant has biological activity of a haploid inducer.

The invention refers especially to mutations in the CENPC-k motif of the KNL2 protein of plants. The CENPC-k motif is in the C-Terminal part of the KNL2 protein of plants.

In a preferred embodiment the at least one mutation is in the C-terminal part of the KNL2 protein.

Accordingly the invention relates especially to a plant comprising a non-natural DNA sequence expressing a mutated, i.e. non-natural protein, especially a mutated, i.e. non-natural KNL2 protein. The according SDNA and KNL2 protein are accordingly artificial.

In a preferred embodiment the at least one mutation is a point mutation. Preferred are especially one or two point mutations in the CENPC-k motif.

In a preferred embodiment the KNL2 protein comprises a CENP-C like motif wherein the nucleotide sequence comprises a point mutation causing in the CENP-C like motif an amino acid substitution which confers the biological activity of a haploid inducer.

In a preferred embodiment the KNL2 protein comprises an amino acid sequence according to one of SEQ ID No. 23 to SEQ ID No. 123 or SEQ ID No. 164 to SEQ ID No. 274.

In a preferred embodiment the at least one mutation causes a deletion or substitution of at least one specified amino acid of SEQ ID No. 3 to SEQ ID No. 22 or of SEQ ID No. 127 to SEQ ID No. 163. The mutation refers also to an addition of an amino acid to the amino acids of SEQ ID No. 3 to SEQ ID No. 22 or of SEQ ID No. 127 to SEQ ID No. 163.

The non-mutated CENPC-k motif of the KNL2 protein of the plant has preferably an amino acid sequence as outlined in SEQ ID No. 3 to SEQ ID No. 22 or in SEQ ID No. 127 to SEQ ID No. 163.

The non-mutated CENPC-k motif of the KNL2 protein of the plant has preferably an amino acid sequence as outlined in one of the consensus sequences SEQ ID No. 124 to SEQ ID No. 126.

In a preferred embodiment the plant comprises also a nucleotide sequence encoding a centromere histone H3 (CENH3) protein comprising a CATD domain, wherein the nucleotide sequence comprises at least one mutation causing in the CATD domain an amino acid substitution which confers the biological activity of a haploid inducer.

In a preferred embodiment crossing between the plant and a wildtype plant or plant expressing wildtype KNL2 protein yields at least 0.1% haploid progeny.

In a preferred embodiment the nucleotide sequence comprising the at least one mutation is an endogenous gene or a transgene, especially an artificial transgene.

In a preferred embodiment the nucleotide sequence comprising the at least one mutation is a transgene and at least one endogenous gene encoding a KNL2 protein is inactivated or knocked out.

In a preferred embodiment the amino acid arginine at position 10 of SEQ ID No. 4 to SEQ ID No. 22 is deleted or substituted, preferably substituted for alanine.

In a preferred embodiment the amino acid tryptophan at position 19 of SEQ ID No. 4 to SEQ ID No. 22 is deleted or substituted, preferably substituted for arginine.

In a preferred embodiment the amino acid arginine at position 8 of SEQ ID No. 127 to SEQ ID No. 143, SEQ ID No. 147, SEQ ID No. 149 to SEQ ID No. 152 is deleted or substituted, preferably substituted for alanine.

In a preferred embodiment the amino acid tryptophan at position 17 of SEQ ID No. 127 to SEQ ID No. 143, SEQ ID No. 147, SEQ ID No. 149 to SEQ ID No. 152 is deleted or substituted, preferably substituted for arginine.

In a preferred embodiment the amino acid arginine at position 7 of SEQ ID No. 153 to SEQ ID No. 162 is deleted or substituted, preferably substituted for alanine.

In a preferred embodiment the amino acid tryptophan at position 16 of SEQ ID No. 153 to SEQ ID No. 162 is deleted or substituted, preferably substituted for arginine.

In a preferred embodiment the amino acid arginine at position 8 of SEQ ID No. 144 to SEQ ID No. 146 and SEQ ID No. 148 is deleted or substituted, preferably substituted for alanine.

In a preferred embodiment the amino acid glycin at position 17 of SEQ ID No. 144 to SEQ ID No. 146 and SEQ ID No. 148 is deleted or substituted, preferably substituted for arginine.

In a preferred embodiment the amino acid arginine at position 6 of SEQ ID No. 163 is deleted or substituted, preferably substituted for alanine.

In a preferred embodiment the amino acid tryptophan at position 15 of SEQ ID No. 163 is deleted or substituted, preferably substituted for arginine.

In a preferred embodiment the plant has one isoform of KNL2.

The invention relates also to a part of the plant according to the invention, which is preferably a shoot vegetative organ, root, flower or floral organ, seed, fruit, ovule, embryo, plant tissue or cell. Preferably the part of the plant expresses the mutated form of the KNL2 protein.

The invention relates also to a haploid plant obtainable by crossing a plant according to the invention with a plant expressing wildtype KNL2 protein.

The invention relates also to a haploid plant obtainable by crossing in a first step a plant according to the invention with a plant comprising a mutated protein, which confers the biological activity of a haploid inducer, and crossing in a second step a plant obtained in the first step with a plant expressing wildtype KNL2 protein and the wildtype form of the other protein.

The invention relates also to a haploid plant obtainable by crossing in a first step a plant according to the invention with a plant comprising a nucleotide sequence encoding a centromere assembly factor or a spindle assembly checkpoint protein, wherein the nucleotide sequence comprises at least one mutation which confers the biological activity of a haploid inducer, and crossing in a second step a plant obtained in the first step with a plant expressing wildtype KNL2 protein and preferably wildtype of the centromere assembly factor or the spindle assembly checkpoint protein.

The invention relates also to a haploid plant obtainable by crossing in a first step a plant according to the invention with a plant comprising a nucleotide sequence encoding a centromere histone H3 (CENH3) protein comprising a CATD domain, wherein the nucleotide sequence comprises at least one mutation causing in the CATD domain an amino acid substitution which confers the biological activity of a haploid inducer, and crossing in a second step a plant obtained in the first step with a plant expressing wildtype KNL2 protein and wildtype CENH3 protein.

The invention relates also to a double haploid plant obtainable by converting the haploid plant according to the invention into a double haploid plant, preferably via colchicine treatment.

The invention relates also to a method of generating a haploid plant, comprising the steps of: a) crossing a plant according to the invention to a plant expressing the wildtype KNL2 protein, and b) identifying the haploid progeny plant generated from the crossing step.

The invention relates also to a method of generating a double haploid plant, comprising the steps of: a) crossing a plant according to the invention to a plant expressing wildtype KNL2 protein, b) identifying a haploid progeny plant generated from the crossing step, and c) converting the haploid progeny plant into a double haploid plant, preferably via colchicine treatment or via spontaneous chromosome doubling.

The invention relates also to a method of generating a haploid plant, comprising the steps of: a) crossing a plant according to the invention to a plant expressing wildtype KNL2 protein but comprising a nucleotide sequence encoding a centromere histone H3 (CENH3) protein comprising a CATD domain, wherein the nucleotide sequence comprises at least one mutation causing in the CATD domain an amino acid substitution which confers the biological activity of a haploid inducer, b) crossing a plant obtained in step a) to a plant expressing wildtype KNL2 protein and wildtype CENH3 protein, and c) identifying the haploid progeny plant generated from step b).

A method of generating a double haploid plant, comprising the steps of: a) crossing a plant according to the invention to a plant expressing wildtype KNL2 protein but comprising a nucleotide sequence encoding a centromere histone H3 (CENH3) protein comprising a CATD domain, wherein the nucleotide sequence comprises at least one mutation causing in the CATD domain an amino acid substitution which confers the biological activity of a haploid inducer, b) crossing a plant obtained in step a) to a plant expressing wildtype KNL2 protein and wildtype CENH3 protein, c) identifying a haploid progeny plant generated from step b), and d) converting the haploid progeny plant into a double haploid plant, preferably via colchicine treatment or via spontaneous chromosome doubling.

In a preferred embodiment the knl2 mutant is transformed with GFP-tailswap CENH3.

The invention relates also to a haploid progeny plant generated in a method according to the invention.

The invention relates also to a double haploid progeny plant generated in a method according to the invention.

The invention relates also to a method of facilitating a cytoplasm exchange, comprising the steps of: x) crossing a plant according to claims 1 to 15 as ovule parent with a plant expressing wildtype KNL2 protein as pollen parent, and y) obtaining a haploid progeny plant comprising the chromosomes of the pollen parent and the cytoplasm of ovule parent. The invention relates also to a haploid progeny plant generated in this method.

The invention relates also to a method of generating a plant according to the invention, comprising the steps of: i) subjecting seeds of a plant to a sufficient amount of the mutagen ethylmethane sulfonate to obtain M1 plants, ii) allowing sufficient production of fertile M2 plants, iii) isolating genomic DNA of M2 plants and iv) selecting individuals possessing at least one amino acid mutation in KNL2, preferably in the C-terminal part of KNL2.

The invention relates also to a nucleotide sequence encoding KNL2 or at least the C-terminal part of KNL2 protein comprising at least one mutation. Preferably the mutation causes in the C-terminal part an amino acid substitution. The invention relates also to a vector comprising this nucleotide sequence.

The invention relates also to a plant cell or host cell comprising this nucleotide sequence or this vector as a transgene.

The invention relates also to a method of generating a plant according to the invention, comprising the steps of: yy) transforming a plant cell with the nucleotide sequence or the vector according to the invention, and zz) regenerating a plant having the biological activity of a haploid inducer from the plant cell.

The *Arabidopsis thaliana* sequences in this application serve only as references and do not limit the invention to the particular *A. thaliana* sequences. Due to the high level of conservation ones skilled in the art is able to find the nucleotide sequence and amino acid sequence corresponding to the *A. thaliana* sequences in any other plant material or plant species. This is shown for example for a number of other plants in the sequence listing and in FIG. 1*b*. In plants the length of the amino acid sequence for KNL2 is in the same area, i.e. between 550 and 650 amino acids long. The CENP-C like motif, especially the CENPC-k motif is always at the C-terminal part. Accordingly, a skilled person can easily obtain a mutated KNL2 protein in any plant species of interest, e.g. crop plants. Interestingly the human KNL2 protein has no CENP-C like motif.

The KNL2 protein that we recently identified in *A. thaliana* (Lermontova et al (2013) Plant Cell, 25, 3389-3404. IP-9,58) is involved in the initiation of CENH3 assembly via the generation of a correct epigenetic status at centromeres. It localizes at centromeres and nucleoplasm and colocalizes with CENH3.

The present inventors surprisingly found that crossing of knl2 mutant female to a wild-type male has resulted in formation of haploid seeds. In wheat, which has six isoforms of CENH3, only three isoforms of KNL2 can be identified making it a perfect target to develop inducer lines. In barley there is even more only one isoform of KNL2. Additionally, they identified putative CENP-C motif at the C-terminus of KNL2 and demonstrated that mutagenesis of conserved amino acids within this motif disturbs the centromeric localization of KNL2. A T-DNA insertion mutant for KNL2 showed a reduced intensity of CENH3 immunosignals at the centromeres, as well as mitotic and meiotic defects.

The present invention, using mutants of KNL2 for the production of haploid and double haploid plants has inter alia the following advantages: In the present KNL2 approach only three genes have to be inactivated instead of six CENH3 genes in wheat. In other plants like barley even only one gene has to be inactivated instead of two CENH3 genes. Furthermore, in contrast to the cenh3 mutant, which is viable only in heterozygous state, a viable homozygous mutant can be generated for KNL2. The knl2 mutant can be crossed directly with the wild type. Thus, not only the final product, but also the inducer lines can be non-GMO. The "KNL2 approach" can also be applied to a broad number of genotypes. The haploid induction efficiency can be up to around 10% or even more.

The present inventors surprisingly found that KNL2 has not only a SANTA domain at the N-terminus but has also a CENP-C like motif, especially a CENPC-k motif at the C-terminus. Furthermore it was surprisingly shown that mutagenesis of conserved amino acids within this CENP-C like motif, especially the CENPC-k motif disturbs the centromeric localization of KNL2.

The present inventors surprisingly found that a plant possessing the capability to produce haploid progeny, i.e. a haploid inducer, can be obtained by substituting a single amino acid within the CENP-C like motif, especially a CENPC-k motif of the KNL2 protein. Advantageously, this can be achieved by transgenic as well as non-transgenic methods. Non-transgenic methods are preferred because of enormous costs for deregulation of genetically modified organisms (GMO) as well as increasing public rejection of genetically modified organisms (GMO) or plants generated by means of GMO, in particular crops for human consumption, and extensive market authorisation processes including rigorous safety assessments of such GMOs.

If amino acids in the CENP-C like motif, especially in the CENPC-k motif are exchanged, this is marked in the single letter code with a "X" and in the three letter code with a "Xaa". "X" and "Xaa" stands for any naturally occurring amino acid. The amino acids herein are marked as one letter code.

Preferably, the KNL2 protein comprises an amino acid sequence according to one of SEQ ID No. 23 to SEQ ID No. 123 or SEQ ID No. 164 to SEQ ID No. 274.

Preferably, the amino acid arginine at position 10 of SEQ ID No. 4 to SEQ ID No. 22 is substituted, preferably substituted for alanine and/or wherein the amino acid tryptophan at position 19 of SEQ ID No. 4 to SEQ ID No. 22 is substituted, preferably substituted for arginine or wherein the amino acid arginine at position 8 or 7 or 6 of SEQ ID No. 127 to SEQ ID No. 163 is substituted, preferably substituted for alanine and/or wherein the amino acid tryptophan at position 17 or 16 or 15 of SEQ ID No. 4 to SEQ ID No. 22 is substituted, preferably substituted for arginine.

Preferably, in the mutated CENP-C like motif and especially in the mutated CENPC-k motif according to SEQ ID No. 164 to SEQ ID No. 200 the X is not R.

Preferably, in the mutated CENP-C like motif and especially in the mutated CENPC-k motif according to SEQ ID No. 201 to SEQ ID No. 237 the X is not W. Preferably, in the mutated CENP-C like motif and especially in the mutated CENPC-k motif according to SEQ ID No. 201 to SEQ ID No. 237 the X is not G.

Preferably, in the mutated CENP-C like motif and especially in the mutated CENPC-k motif according to SEQ ID No. 201 to SEQ ID No. 237 the X is not W or G.

Preferably, in the mutated CENP-C like motif and especially in the mutated CENPC-k motif according to SEQ ID No. 238 to SEQ ID No. 274 the first X (at the N-terminal side of the sequence) is not R. Preferably, in the mutated CENP-C like motif and especially in the mutated CENPC-k motif according to SEQ ID No. 238 to SEQ ID No. 274 the second X (at the C-terminal side of the sequence) is not W. Preferably, in the mutated CENP-C like motif and especially in the mutated CENPC-k motif according to SEQ ID No. 238 to SEQ ID No. 274 the second X (at the C-terminal side of the sequence) is not G. Preferably, in the mutated CENP-C like motif and especially in the mutated CENPC-k motif according to SEQ ID No. 238 to SEQ ID No. 274 the second X (at the C-terminal side of the sequence) is not W or G.

The wording "is not R", "is not W", "is not G" and "is not "W or G" means that at this position any other amino acid, especially any other natural amino acid can be present beside said amino acids.

Preferably the wildtype, i.e. the non-mutated CENPC-k motif, i.e. the CENP-k motif without the mutation according to the invention, comprises an amino acid sequence according to one of SEQ ID No. 124 to SEQ ID No. 126.

Preferably, the non-mutated CENP-C like motif, especially in the non-mutated CENPC-k motif of the plant KNL2-protein comprises the amino acid sequence $X^1X^2GRX^5X^6X^7X^8X^9X^{10}X^{11}X^{12}X^{13}$, wherein $X^1$ is R or K, $X^2$ is S or T, $X^5$ is L or I or V or M or W, $X^6$ is L or I or V, $X^7$ is L or V, $X^8$ is P or S or R, $X^9$ is P or T or S or R or C or K, $X^{10}$ is L or M, $X^{11}$ is A or E or Q or D, $X^{12}$ is F or Y or L or P or K or N, $X^{13}$ is W or G. More preferably $X^1$ is R, $X^2$ is S, $X^5$ is L or V, $X^6$ is L, $X^7$ is L or V, $X^8$ is P, $X^9$ is P or T or S, $X^{10}$ is L, $X^{11}$ is E or D or A, $X^{12}$ is F or Y or N, $X^{13}$ is W. However any combination derivable from SEQ ID No. 124 and FIG. 3A and not only the specific sequences disclosed are part of the invention and can be used by the person skilled in the art.

Preferably, the non-mutated CENP-C like motif, especially the non-mutated CENPC-k motif comprises an amino acid sequence with amino acids 1 to 13 according to table 1:

TABLE 1 preferred CENPC-k motive amino acid sequence

| position | Amino acid |
|---|---|
| 1 | R or K, preferably R |
| 2 | S or T, preferably S |

TABLE 1-continued preferred CENPC-k motive amino acid sequence

| position | Amino acid |
|---|---|
| 3 | G |
| 4 | R |
| 5 | L or I or V or M or W, preferably L or V |
| 6 | L or I or V, preferably L |
| 7 | L or V |
| 8 | P or S or R, preferably P |
| 9 | P or T or S or C or R or K, preferably P or T or S |
| 10 | L or M |
| 11 | A or E or Q or D, preferably E or D or A |
| 12 | F or Y or L or P or K or N, preferably F or N or Y |
| 13 | W or G, preferably W |

Preferably, the non-mutated CENP-C like motif, especially in the CENPC-k motif of the monocotyledonous plant KNL2-protein comprises the amino acid sequence $SGRX^4X^5VPX^8LX^{10}X^{11}X^{12}C$, wherein $X^4$ is V or L, $X^5$ is V or I, $X^8$ is P or T or K, $X^{10}$ is D or A, $X^{11}$ is L or P or K or N, $X^{12}$ is G or W. However any combination derivable from SEQ ID No. 125 and FIG. 3B and not only the specific sequences disclosed are part of the invention and can be used by the person skilled in the art.

Preferably, the non-mutated CENP-C like motif, especially in the CENPC-k motif of a monocotyledonous plant, comprises an amino acid sequence with amino acids 1 to 13 according to table 2:

TABLE 2 preferred monocotyledonous CENPC-k motive amino acid sequence

| position | Amino acid |
|---|---|
| 1 | S |
| 2 | G |
| 3 | R |
| 4 | V or L |
| 5 | V or I |
| 6 | V |
| 7 | P |
| 8 | P or T or K, preferably P or T |
| 9 | L |
| 10 | D or A, preferably D |
| 11 | L or P or K or N, preferably N |
| 12 | G or W |
| 13 | C |

Preferably, the non-mutated CENP-C like motif, especially in the CENPC-k motif of the dicotyledonous plant KNL2-protein comprises the amino acid sequence $SRX^3GRX^6X^7X^8X^9X^{10}X^{11}X^{12}X^{13}WX^{15}NX^{17}$, wherein $X^3$ is S or T, $X^6$ is I or V or L or W or M, $X^7$ is L or I, $X^8$ is L or V, $X^9$ is P or S or R, $X^{10}$ is P or S or T or C or R, $X^{11}$ is L or M, $X^{12}$ is A or E or D or Q, $X^{13}$ is F or Y, $X^{15}$ is R or C or H and $X^{17}$ is Q or E. However any combination derivable from SEQ ID No. 126 and FIG. 3C and not only the specific sequences disclosed are part of the invention and can be used by the person skilled in the art.

Preferably, the non-mutated CENP-C like motif, especially in the CENPC-k motif of a dicotyledonous plant, comprises an amino acid sequence with amino acids 1 to 13 according to table 3:

TABLE 3 preferred dicotyledonous CENPC-k motive amino acid sequence

| position | Amino acid |
| --- | --- |
| 1 | S |
| 2 | R |
| 3 | S or T, preferably S |
| 4 | G |
| 5 | R |
| 6 | I or V or L or W or M, preferably L or V |
| 7 | L or I, preferably L |
| 8 | L or V, preferably L |
| 9 | P or S or R, preferably P or S |
| 10 | P or S or T or C or R, preferably P or T or S |
| 11 | L or M, preferably L |
| 12 | A or E or D or Q, preferably E |
| 13 | F or Y, preferably F |
| 14 | W |
| 15 | R or C or H, preferably R |
| 16 | N |
| 17 | Q or E, preferably Q |

Preferably, the non-mutated CENP-C like motif, especially in the CENPC-k motif exhibits the amino acid sequences according to SEQ ID No. 23, i.e. RSGX, wherein X is R and SEQ ID No. 25, i.e. XRNQ, wherein X is W or G, especially W.

In a preferred embodiment there is at least one mutation, preferably one point mutation in at least one, preferably one, of these two non-mutated sequences.

In a preferred embodiment, the X in SEQ ID No. 23 is A. In a preferred embodiment, the X in SEQ ID No. 25 is R.

In a preferred embodiment, the X in SEQ ID No. 23 is an aliphatic amino acid. In a preferred embodiment, the X in SEQ ID No. 23 is A, G, I, L, M, P or V.

In a preferred embodiment, the X in SEQ ID No. 25 is a basic amino acid. In a preferred embodiment, the X in SEQ ID No. 25 is R, H or K.

Preferably the mutated KNL2 protein comprises at least one of the following sequences, preferably in the C-terminal part, preferably in the CENP-C like motif: "RSGX" (SEQ ID No. 23), preferably "RSGA" (SEQ ID No. 24) and/or "XRNQ" (SEQ ID No. 25), preferably "RRNQ" (SEQ ID No. 26).

According to one preferred embodiment of the present invention, a mutation causing a substitution of any of the amino acid shown in SEQ ID No. 31 as X can produce the desired plant possessing the capability to produce haploid progeny.

The term "plant" refers to any plant, but particularly seed plants. The term 'plant' according to the present invention includes whole plants or parts of such a whole plant.

Whole plants preferably are seed plants, or a crop. Parts of a plant are e.g. shoot vegetative organs/structures, e.g., leaves, stems and tubers; roots, flowers and floral organs/structures, e.g. bracts, sepals, petals, stamens, carpels, anthers and ovules; seed, including embryo, endosperm, and seed coat; fruit and the mature ovary; plant tissue, e.g. vascular tissue, ground tissue, and the like; and cells, e.g. guard cells, egg cells, trichomes and the like; and progeny of the same.

In any case, the plant of the present invention comprises at least one cell comprising a nucleotide sequence encoding a KNL2 protein, wherein the nucleotide sequence comprises at least one mutation, preferably causing in the KNL2 protein an amino acid substitution, deletion or addition which can confer the biological activity of a haploid inducer to the plant, preferably as specified herein in more detail. Most preferably, most or in particular all cells of the plant of the present invention comprises the mutation as described herein.

The species of plants that can be used in the method of the invention are preferably eudicot, dicot and monocot plants.

The term 'plant' in a preferred embodiment relates solely to a whole plant, i.e. a plant exhibiting the full phenotype of a developed plant and capable of reproduction, a developmental earlier stage thereof, e.g. a plant embryo, or to both.

In an embodiment of the present invention the term 'plant' refers to a part of a whole plant, in particular plant material, plant cells or plant cell cultures.

The term 'plant cell' describes the structural and physiological unit of the plant, and comprises a protoplast and a cell wall. The plant cell may be in form of an isolated single cell, such as a stomatal guard cells or a cultured cell, or as a part of a higher organized unit such as, for example, a plant tissue, or a plant organ.

The term 'plant material' includes plant parts, in particular plant cells, plant tissue, in particular plant propagation material, preferably leaves, stems, roots, emerged radicles, flowers or flower parts, petals, fruits, pollen, pollen tubes, anther filaments, ovules, embryo sacs, egg cells, ovaries, zygotes, embryos, zygotic embryos per se, somatic embryos, hypocotyl sections, apical meristems, vascular bundles, pericycles, seeds, roots, cuttings, cell or tissue cultures, or any other part or product of a plant.

Thus, the present invention also provides plant propagation material of the plants of the present invention. Said "plant propagation material" is understood to be any plant material that may be propagated sexually or asexually in vivo or in vitro. Particularly preferred within the scope of the present invention are protoplasts, cells, calli, tissues, organs, seeds, embryos, pollen, egg cells, zygotes, together with any other propagating material obtained from transgenic plants. Parts of plants, such as for example flowers, stems, fruits, leaves, roots originating in mutated plants or their progeny previously mutated, preferably transformed, by means of the methods of the present invention and therefore consisting at least in part of mutated cells, are also an object of the present invention.

The term "transgenic plant" or "transgenic plant cell" or "transgenic plant material" refers to a plant, plant cell or plant material which is characterised by the presence of a polynucleotide or polynucleotide variant of the present invention, which may—in case it is autologous to the plant—either be located at another place or in another orientation than usually found in the plant, plant cell or plant material or which is heterologous to the plant, plant cell or plant material. Preferably, the transgenic plant, plant cell or plant material expresses the polynucleotide or its variants such as to induce apomixis.

The term "plant cell" describes the structural and physiological unit of the plant, and comprises a protoplast and a cell wall. The plant cell may be in form of an isolated single cell, such as a stomatal guard cells or a cultured cell, or as a part of a higher organized unit such as, for example, a plant tissue, or a plant organ.

The term "plant material" includes plant parts, in particular plant cells, plant tissue, in particular plant propagation material, preferably leaves, stems, roots, emerged radicles, flowers or flower parts, petals, fruits, pollen, pollen tubes, anther filaments, ovules, embryo sacs, egg cells, ovaries, zygotes, embryos, zygotic embryos per se, somatic embryos, hypocotyl sections, apical meristems, vascular bundles, pericycles, seeds, roots, cuttings, cell or tissue cultures, or any other part or product of a plant.

Thus, the present invention also provides plant propagation material of the transgenic plants of the present invention. Said "plant propagation material" is understood to be any plant material that may be propagated sexually or asexually in vivo or in vitro. Particularly preferred within the scope of the present invention are protoplasts, cells, calli, tissues, organs, seeds, embryos, pollen, egg cells, zygotes, together with any other propagating material obtained from transgenic plants. Parts of plants, such as for example flowers, stems, fruits, leaves, roots originating in transgenic plants or their progeny previously transformed by means of the methods of the present invention and therefore consisting at least in part of transgenic cells, are also an object of the present invention. Especially preferred plant materials, in particular plant propagation materials, are apomictic seeds.

Particularly preferred plants are monocotyledonous or dicotyledonous plants. Particularly preferred are crop or agricultural plants, such as sunflower, peanut, corn, potato, sweet potato, bean, pea, chicory, lettuce, endive, cabbage, cauliflower, broccoli, turnip, radish, spinach, onion, garlic, eggplant, celery, carrot, squash, pumpkin, zucchini, cucumber, apple, pear, melon, strawberry, grape, raspberry, pineapple, soybean, *Cannabis*, *Humulus* (hop), tomato, sorghum, sugar cane, and non-fruit bearing trees such as poplar, rubber, *Paulownia*, pine, elm, *Lolium*, *Festuca*, *Dactylis*, alfalfa, safflower, tobacco, cassava, coffee, coconut, pineapple, citrus trees, cocoa, tea, banana, avocado, fig, guava, mango, olive, papaya, cashew, macadamia, almond, green beans, lima beans, peas, fir, hemlock, spruce, redwood, in particular maize, wheat, barley, sorghum, rye, oats, turf and forage grasses, millet, rice and sugar cane. Especially preferred are maize, wheat, sorghum, rye, oats, turf grasses and rice.

Particularly preferred are also ornamental plants such as ornamental flowers and ornamental crops, for instance Begonia, Carnation, Chrysanthemum, Dahlia, Gardenia, Asparagus, Geranium, Daisy, Gladiolus, Petunia, Gypsophila, Lilium, Hyacinth, Orchid, Rose, Tulip, Aphelandra, Aspidistra, Aralia, Clivia, Coleus, Cordyline, Cyclamen, Dracaena, Dieffnbachia, Ficus, Philodendron, Poinsettia, Fern, Ivy, Hydrangea, Limonium, Monstera, Palm, Datepalm, Potho, Singonio, Violet, Daffodil, Lavender, Lily, Narcissus, Crocus, Iris, Peonies, Zephyranthes, Anthurium, Gloxinia, Azalea, Ageratum, Bamboo, Camellia, Dianthus, Impatien, Lobelia, Pelargonium, Lilac, Lily of the Valley, Stephanotis, Hydrangea, Sunflower, Gerber daisy, Oxalis, Marigold and Hibiscus.

Among the dicotyledonous plants *Arabidopsis*, Boechera, soybean, cotton, sugar beet, oilseed rape, tobacco, pepper, melon, lettuce, *Brassica* vegetables, in particular *Brassica napus*, sugar beet, oilseed rape and sunflower are more preferred herein.

In a preferred embodiment the plant is a species selected from the group consisting of *Hordeum vulgare, Hordeum bulbusom, Sorghum bicolor, Saccharum officinarium, Zea mays, Setaria italica, Oryza minuta, Oriza sativa, Oryza australiensis, Oryza alta, Triticum aestivum, Secale cereale, Malus domestica, Brachypodium distachyon, Hordeum marinum, Aegilops tauschii, Daucus glochidiatus, Beta vulgaris, Daucus pusillus, Daucus muricatus, Daucus carota, Eucalyptus grandis, Nicotiana sylvestris, Nicotiana tomentosiformis, Nicotiana tabacum, Solanum lycopersicum, Solanum tuberosum, Coffea canephora, Vitis vinifera, Erythrante guttata, Genlisea aurea, Cucumis sativus, Morus notabilis, Arabidopsis arenosa, Arabidopsis lyrata, Arabidopsis thaliana, Crucihimalaya himalaica, Crucihimalaya wallichii, Cardamine flexuosa, Lepidium virginicum, Capsella bursa pastoris, Olmarabidopsis pumila, Arabis hirsute, Brassica napus, Brassica oeleracia, Brassica rapa, Raphanus sativus, Brassica juncea, Brassica nigra, Eruca vesicaria* subsp. *sativa, Citrus sinensis, Jatropha curcas, Populus trichocarpa, Medicago truncatula, Cicer yamashitae, Cicer bijugum, Cicer arietinum, Cicer reticulatum, Cicer judaicum, Cajanus cajanmfolius, Cajanus scarabaeoides, Phaseolus vulgaris, Glycine max, Astragalus sinicus, Lotus japonicas, Torenia fournieri, Allium cepa, Alliumfistulosum, Allium sativum,* and *Allium tuberosum.*

Preferably, the plant according to the present invention is selected from the group consisting of barley (*Hordeum vulgare*), sorghum (*Sorghum bicolor*), rye (*Secale cereale*), Triticale, sugar cane (*Saccharum* officinarium), maize (*Zea mays*), foxtail millet (*Setaria italic*), rice (*Oryza sativa*), *Oryza minuta, Oryza australiensis, Oryza alta,* wheat (*Triticum aestivum*), *Triticum durum, Hordeum bulbosum,* purple false brome (*Brachypodium distachyon*), sea barley (*Hordeum marinum*), goat grass (*Aegilops tauschii*), apple (*Malus domestica*), *Beta vulgaris,* sunflower (*Helianthus annuus*), Australian carrot (*Daucus* glochidiatus), American wild carrot (*Daucus pusillus*), *Daucus muricatus,* carrot (*Daucus carota*), eucalyptus (*Eucalyptus grandis*), Erythranthe guttata, Genlisea aurea, woodland tobacco (*Nicotiana sylvestris*), tobacco (*Nicotiana tabacum*), *Nicotiana tomentosiformis,* tomato (*Solanum lycopersicum*), potato (*Solanum tuberosum*), coffee (*Coffea canephora*), grape vine (*Vitis vinifera*), cucumber (*Cucumis sativus*), mulberry (*Morus notabilis*), thale cress (*Arabidopsis thaliana*), *Arabidopsis lyrata,* sand rock-cress (*Arabidopsis arenosa*), *Crucihimalaya himalaica, Crucihimalaya wallichii,* wavy bittercress (*Cardamine flexuosa*), peppergrass (*Lepidium virginicum*), sheperd's-purse (*Capsella bursa-pastoris*), *Olmarabidopsis pumila,* hairy rockcress (*Arabis hirsute*), rape (*Brassica napus*), broccoli (*Brassica oleracea*), *Brassica rapa, Brassica juncacea,* black mustard (*Brassica nigra*), radish (*Raphanus sativus*), *Eruca vesicaria sativa,* orange (*Citrus sinensis*), *Jatropha curcas, Glycine max,* and black cottonwood (*Populus trichocarpa*).

Particularly preferred the plant is selected from the group consisting of barley (*Hordeum vulgare*), sorghum (*Sorghum bicolor*), rye (*Secale cereale*), Triticale, sugar cane (*Saccharum* officinarium), maize (*Zea mays*), rice (*Oryza sativa*), wheat (*Triticum aestivum*), *Triticum durum, Avena sativa, Hordeum bulbosum, Beta vulgaris,* sunflower (*Helianthus annuus*), carrot (*Daucus carota*), tobacco (*Nicotiana tabacum*), tomato (*Solanum lycopersicum*), potato (*Solanum tuberosum*), coffee (*Coffea canephora*), grape vine (*Vitis vinifera*), cucumber (*Cucumis sativus*), thale cress (*Arabidopsis thaliana*), rape (*Brassica napus*), broccoli (*Brassica oleracea*), *Brassica rapa, Brassica juncacea,* black mustard (*Brassica nigra*), radish (*Raphanus sativus*), and *Glycine max.*

Particularly preferred the plant is selected from the group consisting of *Amborella, Solanum, Camelina, Brassica, Arabidopsis, Alyrata, Capsella, Vigna, Pheaseolus, Medicago, Cicer, Glycine, Arachis, Daucus, Fragaria, Ziziphus, Coffea, Malus, Pyrus, Populus, Vitis, Citrus, Ricinus, Nicotiana, Theobroma, Gossypium, Prunus, Cucumis, Brachypodium, Oryza, Setaria, Sorghum, Musa, Elaesis* and *Phoenix.*

In a preferred embodiment the plant is *Arabidopsis thaliana.*

In a preferred embodiment the plant is barley, i.e. *Hordeum vulgare.*

In the context of the present invention the term 'at least one mutation' refers to preferably one mutation, in particular solely one mutation. In a further preferred embodiment, the term 'at least one mutation' refers to two mutations, in particular solely two mutations. In a further preferred embodiment, the term 'at least one mutation' refers to three mutations, in particular solely three mutations. In a further preferred embodiment, the term 'at least one mutation' refers to four mutations, in particular solely four mutations. In a further preferred embodiment, the term 'at least one mutation' refers to five mutations, in particular solely five mutations.

In a preferred embodiment of the present invention, the at least one mutation is at least one mutation, is at least two mutations, is at least three mutations, is at least four mutations or is at least five mutations.

In a preferred embodiment of the present invention, the maximum number of mutations is two, three, four, five, six, seven, eight, nine and, most preferably, ten.

In a furthermore preferred embodiment, in the KNL2 protein, preferably in the C-terminal region of the KNL2 protein, most preferably in the CENP-C like motif of the KNL2 protein one amino acid substitution, in particular solely one amino acid substitution, is present.

In a furthermore preferred embodiment, in the KNL2 protein, preferably in the C-terminal region of the KNL2 protein, most preferably in the CENP-C like motif of the KNL2 protein, two amino acid substitutions, in particular solely two amino acid substitutions, are present.

In a furthermore preferred embodiment, in the KNL2 protein, preferably in the C-terminal region of the KNL2 protein, most preferably in the CENP-C like motif of the KNL2 protein, three amino acid substitutions, in particular solely three amino acid substitutions, are present.

In a furthermore preferred embodiment, in the KNL2 protein, preferably in the C-terminal region of the KNL2 protein, most preferably in the CENP-C like motif of the KNL2 protein, four amino acid substitutions, in particular solely four amino acid substitutions, are present.

In a furthermore preferred embodiment, in the KNL2 protein, preferably in the C-terminal region of the KNL2 protein, most preferably in the CENP-C like motif of the KNL2 protein, five amino acid substitutions, in particular solely five amino acid substitutions, are present.

In a preferred embodiment of the present invention, in the KNL2 protein, preferably in the C-terminal region of the KNL2 protein, most preferably in the CENP-C like motif of the KNL2 protein, 1, 1 or 2, 1 to 3, 1 to 4, 1 to 5, preferably 1 to 6, and more preferably 1 to 7 amino acid substitutions are present.

In particular, the present invention is concerned with mutations that cause or lead to an amino acid deletion, substitution or addition within the in the KNL2 protein, preferably in the C-terminal region of the KNL2 protein, most preferably in the CENP-C like motif, and especially in the CENPC-k motif of the KNL2 protein. Thus, in the context of the present invention, a mutation preferably is a non-synonymous point mutation or substitution in the DNA sequence encoding the KNL2 protein resulting in a change in amino acid. This is also called a missense mutation. Further, the change in amino acid or the amino acid substitution may be conservative, i.e. a change to an amino acid with similar physiochemical properties, semi-conservative, e.g. negative to positively charged amino acid, or radical, i.e. a change to a vastly different amino acid.

In a preferred embodiment of the present invention, the present plant having biological activity of a haploid inducer is homozygous with respect to the at least one mutation. In a further embodiment of the present invention, the present plant having biological activity of a haploid inducer is heterozygous with respect to the at least one mutation.

The plant according to the present invention has the biological activity of a haploid inducer. This means that crossing between the plant according to the present invention and a wildtype plant or a plant expressing wildtype KNL2 protein yields at least 0.1%, 0.2%, 0.3%, 0.4%, 0.5%, 0.6%, 0.7%, 0.8%, 0.9%, preferably at least 1%, preferably at least 2%, preferably at least 3%, preferably at least 4%, preferably at least 5%, preferably at least 6%, preferably at least 7%, preferably at least 8%, preferably at least 9%, most preferred at least 10%, at least 15%, at least 20% or more haploid progeny. Thereby, a wildtype plant is preferably a plant of the same species which does not comprise the at least one mutation of the plant according to the present invention within the corresponding endogenous KNL2 gene, i.e. the plant is able to express the native KNL2 protein, and a plant expressing wildtype KNL2 is preferably a plant of the same species which comprises i) a nucleotide sequence encoding the KNL2 protein without the at least one mutation of the plant according to the present invention and is able to express said native KNL2 protein or ii) a nucleotide sequence encoding a KNL2 protein from another plant species that shows a comparable functionality to the native KNL2, for instance, such KNL2 protein derived from another plant species can be introduced as a transgene.

Thus, the present invention most advantageously provides means and methods to generate haploid inducer lines in a wide range of eudicot, dicot and monocot species. The present invention also allows the exchange of maternal cytoplasm and to create for instance cytoplasmic male sterilite plants with a desired genotype in a single process step. The present invention is advantageous insofar as a single amino acid mutation can be generated by mutagenesis or any other non-GMO-based approaches.

Thus, the entire process of haploidization via application of a haploid inducer line characterized by a point mutated endogenous KNL2 gene encoding a KNL2 protein with amino acid substitutions at at least one of the positions provided by the present invention is non-transgenic in a preferred embodiment.

In the context of the present invention, an "endogenous" gene, allele or protein refers to a non-recombinant sequence of a plant as the sequence occurs in the respective plant, in particular wildtype plant. The term "mutated" refers to a human-altered sequence. Examples of human-induced non-transgenic mutation include exposure of a plant to a high dose of chemical, radiological, or other mutagen for the purposes of selecting mutants. Alternatively, human-induced transgenic mutations, i.e. recombinant alterations or genomic engineering for example by means of TALE nucleases, zinc-finger nucleases or a CRISPR/Cas system, include fusions, insertions, deletions, and/or changes to the DNA or amino acid sequence.

A polynucleotide or polypeptide sequence is "heterologous or exogenous to" an organism if it originates from a foreign species, or, if from the same species, is modified from its original form. "Recombinant" refers to a human-altered, i.e. transgenic polynucleotide or polypeptide sequence. A "transgene" is used as the term is understood in the art and refers to a, preferably heterologous, nucleic acid introduced into a cell by human molecular manipulation of the cell's genome, e.g. by molecular transformation. Thus, a "transgenic plant" is a plant comprising a transgene, i.e. is a genetically-modified plant. The transgenic plant can be the initial plant into which the transgene was introduced as well as progeny thereof whose genome contains the transgene as well.

The term 'nucleotide sequence encoding' refers to a nucleic acid which directs the expression of a specific protein, in particular the KNL2 protein or parts thereof. The nucleotide sequences include both the DNA strand sequence that is transcribed into RNA and the RNA sequence that is translated into the protein. The nucleotide sequences include both the full length nucleic acid sequences as well as non-full length sequences derived from the full length sequences.

The term 'gene' refers to a coding nucleotide sequence and associated regulatory nucleotide sequences.

The term 'regulatory element' refers to a sequence, preferably a nucleotide sequence, located upstream (5'), within and/or downstream (3') to a nucleotide sequence, preferably a coding sequence, whose transcription and expression is controlled by the regulatory element, potentially in conjunction with the protein biosynthetic apparatus of the cell. 'Regulation' or 'regulate' refer to the modulation of the gene expression induced by DNA sequence elements located primarily, but not exclusively upstream (5') from the transcription start of the gene of interest. Regulation may result in an all or none response to a stimulation, or it may result in variations in the level of gene expression.

A regulatory element, in particular DNA sequence, such as a promoter is said to be "operably linked to" or "associated with" a DNA sequence that codes for a RNA or a protein, if the two sequences are situated and orientated such that the regulatory DNA sequence effects expression of the coding DNA sequence.

A 'promoter' is a DNA sequence initiating transcription of an associated DNA sequence, in particular being located upstream (5') from the start of transcription and being involved in recognition and being of the RNA-polymerase. Depending on the specific promoter region it may also include elements that act as regulators of gene expression such as activators, enhancers, and/or repressors.

A '3' regulatory element' (or '3' end') refers to that portion of a gene comprising a DNA segment, excluding the 5' sequence which drives the initiation of transcription and the structural portion of the gene, that determines the correct termination site and contains a polyadenylation signal and any other regulatory signals capable of effecting messenger RNA (mRNA) processing or gene expression. The polyadenylation signal is usually characterised by effecting the addition of polyadenylic acid tracts to the 3' end of the mRNA precursor. Polyadenylation signals are often recognised by the presence of homology to the canonical form 5'-AATAAA-3'.

The term 'coding sequence' refers to that portion of a gene encoding a protein, polypeptide, or a portion thereof, and excluding the regulatory sequences which drive the initiation or termination of transcription.

The gene, coding sequence or the regulatory element may be one normally found in the cell, in which case it is called 'autologous' or 'endogenous', or it may be one not normally found in a cellular location, in which case it is termed 'heterologous', 'transgenic' or 'transgene'.

A 'heterologous' gene, coding sequence or regulatory element may also be autologous to the cell but is, however, arranged in an order and/or orientation or in a genomic position or environment not normally found or occurring in the cell in which it is transferred.

The term 'vector' refers to a recombinant DNA construct which may be a plasmid, virus, autonomously replicating sequence, an artificial chromosome, such as the bacterial artificial chromosome BAC, phage or other nucleotide sequence, in which at least two nucleotide sequences, at least one of which is a nucleic acid molecule of the present invention, have been joined or recombined. A vector may be linear or circular.

A vector may be composed of a single or double stranded DNA or RNA.

The term 'expression' refers to the transcription and/or translation of an endogenous gene or a transgene in plants. 'Transformation', 'transforming' and 'transferring' refers to methods to transfer nucleic acid molecules, in particular DNA, into cells including, but not limited to, biolistic approaches such as particle bombardment, microinjection, permeabilizing the cell membrane with various physical, for instance electroporation, or chemical treatments, for instance polyethylene glycol or PEG, treatments; the fusion of protoplasts or *Agrobacterium tumefaciens* or *rhizogenes* mediated trans-formation. For the injection and electroporation of DNA in plant cells there are no specific requirements for the plasmids used. Plasmids such as pUC derivatives can be used. If whole plants are to be regenerated from such transformed cells, the use of a selectable marker is preferred. Depending upon the method for the introduction of desired genes into the plant cell, further DNA sequences may be necessary; if, for example, the Ti or Ri plasmid is used for the transformation of the plant cell, at least the right border, often, however, the right and left border of the Ti and Ri plasmid T-DNA have to be linked as flanking region to the genes to be introduced. Preferably, the transferred nucleic acid molecules are stably integrated in the genome or plastome of the recipient plant.

In the context of the present invention the term 'biological activity of a haploid inducer' or 'haploid inducer' or 'haploid inducer line' refers to a plant or plant line having the capability to produce haploid progeny or offspring in at least 0.1%, at least 0.2%, 0.3%, 0.4%, 0.5%, 0.6%, 0.7%, 0.8%, 0.9%, preferably at least 1%, preferably at least 2%, preferably at least 3%, preferably at least 4%, preferably at least 5%, preferably at least 6%, preferably at least 7%, preferably at least 8%, preferably at least 9%, most preferred at least 10%, most preferred at least 15%, most preferred at least 20% of cases when crossed to a wildtype plant or a plant at least expressing wildtype KNL2 protein. Since the chromosomes of the haploid inducer are eliminated during meiosis the resulting haploid progeny only comprises the chromosomes of the wildtype parent. However, in case the haploid inducer was the ovule parent of the cross, the haploid progeny possesses the cytoplasm of the inducer and the chromosomes of the wildtype parent.

The plant according to the present invention contains in a preferred embodiment the nucleotide sequence encoding the KNL2 either as an endogenous gene or a transgene.

The invention relates in a preferred embodiment to a plant according to the present teaching, wherein the at least one amino acid substitution is introduced into the nucleotide sequence encoding KNL2 non-transgenically or transgenically.

Thus, preferably in an embodiment, wherein the at least one mutation is effected in the endogenous KNL2 gene, the obtained plant is non-transgenic. Preferably, the mutation is effected via non-transgenic mutagenesis, in particular chemical mutagenesis, preferably via EMS (ethylmethane sulfonate)-induced TILLING.

Thus, the present invention relates to a plant, wherein the non-transgenic introduction of the at least one mutation causing in KNL2, especially in the C-terminal region of KNL2 an amino acid substitution, deletion or addition which confers the biological activity of a haploid inducer is effected via chemical mutagenesis, in particular via TILLING.

Alternatively, the present invention relates to a plant, wherein the non-transgenic introduction of the at least one mutation causing in KNL2, especially in the C-terminal region of KNL2 an amino acid substitution, deletion or addition which confers the biological activity of a haploid inducer is effected via chemical mutagenesis, in particular via a CRISPR/Cas method, especially the CRISPR/Cas9 technology.

TILLING as well as a CRISPR/Cas method has the advantage that not only the haploid plant but also the inducer plants are non-GMO.

In another preferred embodiment, the at least one mutation is introduced into the plant in form of a transgene. Preferably, this is done by transforming a vector comprising a nucleotide sequence encoding at least C-terminal region of KNL2 comprising at least one amino acid substitution, preferably such as described herein. Methods for transformation of a plant and introducing a transgene into the genome of a plant are well-known in the prior art.

Preferably, the *Agrobacterium* mediated transformation, floral dip method or particle bombardment are used for transformation.

In the preferred embodiment, wherein the nucleotide sequence encoding the mutated KNL2 protein according to the present invention is transformed into the plant in form of a transgene and one or two alleles of the endogenous KNL2 gene are preferably inactivated or knocked out. Another preferred embodiment, wherein the nucleotide sequence encoding the mutated KNL2 protein according to the present invention is transformed into the plant in form of a transgene and the transgene is overexpressed in order to be more competitive as the endogenous KNL2 protein.

The present invention also provides a plant obtainable, in particular obtained, by a method according to the present invention and which is characterized by having the biological activity of a haploid inducer.

In a preferred embodiment of the present invention, the method of producing the plant having biological activity of a haploid inducer according to the present invention is not an essentially biological method.

Further, the present invention also provides a method of generating the plant having biological activity of a haploid inducer according to the present invention, comprising the steps of:
i) subjecting seeds of a plant to a sufficient amount of the mutagen ethylmethane sulfonate (EMS) to obtain M1 plants,
ii) allowing sufficient production of fertile M2 plants,
iii) isolating genomic DNA of M2 plants and
iv) selecting individuals possessing at least one amino acid substitution, deletion or addition in the KNL2 protein, preferably in the C-terminal region of the KNL2 protein, most preferably in the CENP-C like motif of the KNL2 protein.

The present invention further relates in a preferred embodiment to a method of generating a plant having biological activity of a haploid inducer according to the present invention, comprising the steps of:
xx) providing a vector comprising a nucleotide sequence encoding at least the KNL2 protein, preferably the C-terminal region of the KNL2 protein, most preferably the CENP-C like motif of the KNL2 protein comprising at least one mutation causing in the in the KNL2 protein, preferably in the C-terminal region of the KNL2 protein, most preferably in the CENP-C like motif of the KNL2 protein an amino acid substitution,
yy) transforming a plant cell with the vector, wherein preferably the plant cell comprising one or two endogenous alleles of a KNL2 gene inactivated or knocked out, and
zz) regenerating a plant having the biological activity of a haploid inducer from the plant cell.

The present invention further relates in a preferred embodiment to a method of generating a plant having biological activity of a haploid inducer according to the present invention, comprising the steps of:
yy) transforming a plant cell with a nucleotide sequence encoding at least the KNL2 protein, preferably the C-terminal region of the KNL2 protein, most preferably the CENP-C like motif of the KNL2 protein comprising at least one mutation causing in the in the KNL2 protein, preferably in the C-terminal region of the KNL2 protein, most preferably in the CENP-C like motif of the KNL2 protein an amino acid substitution or a vector comprising a nucleotide sequence encoding at least the KNL2 protein, preferably the C-terminal region of the KNL2 protein, most preferably the CENP-C like motif of the KNL2 protein comprising at least one mutation causing in the in the KNL2 protein, preferably in the C-terminal region of the KNL2 protein, most preferably in the CENP-C like motif of the KNL2 protein domain an amino acid substitution, and
zz) regenerating a plant having the biological activity of a haploid inducer from the plant cell.

In particular, the present invention relates to a haploid plant, obtainable, in particular obtained, by:
a) a cross of a plant having the biological activity of a haploid inducer according to the present invention with a plant expressing wildtype KNL2 protein and optionally
b) identifying haploid progeny generated from the crossing step.

Preferably, the identified haploid plant can be converted into a double haploid plant, preferably via colchicine treatment, which is also part of the present invention. Thus, the present invention also relates to a double-haploid plant, obtainable, in particular obtained, by converting the haploid plant according to the present invention into a double haploid plant, preferably via colchicine treatment or via spontaneous chromosome doubling.

Thus, the present invention provides also a method of generating a haploid plant, comprising the steps of:
a) crossing a plant having the biological activity of a haploid inducer according to the present invention to a plant expressing wildtype KNL2 protein and
b) identifying haploid progeny generated from the crossing step.

In a further step c) the selected haploid plant is preferably converted into a double haploid plant, preferably via colchicine treatment. Thus, the invention relates also to a method of generating a double haploid plant.

In a preferred embodiment of the present invention, the method provided is not an essentially biological method.

The inventors also observed that the efficiency of haploid induction by crosses of knl2 mutant with the wild type varies depending on growth conditions. Therefore knl2 mutant and wild type plants can be grown under different light and temperature conditions.

In a preferred embodiment the plant having the biological activity of a haploid inducer according to the present invention and/or the plant expressing wildtype KNL2 protein are grown in a method according to the present invention before step a) und stress condition, especially under a slight stress condition. A suitable stress condition can be an altered temperature or an altered light regiment. Preferably the plant is grown at a temperature above or below 21° C., for example at a temperature of at least 23° C. and at most 29° C., preferably of around 26° C. or at a temperature of at least 15° C. and at most 20° C., preferably of around 18° C.

In a further method according to the present invention a plant with a mutated KNL2 protein is crossed with a plant with a mutated CENH3 protein and haploid progeny generated from the crossing step are identified.

The identified haploid plants can then be crossed with a wild type plant having neither a mutated KNL2 protein nor a mutated CENH3 protein.

Not to be bound on this theory, the efficiency of haploid induction can increase after combination of knl2 and cenh3 mutations. The combination of several haploid-causing mutations can help to increase the efficiency of haploid generation. Therefore, in an alternative embodiment transformation of knl2 mutant with altered CENH3 variants, e.g. GFP-tailswap can be done to increase its ability to induce haploids. knl2 with a mutation within the CENP-C motif can for example be crossed with cenh3. These double mutants can have an increased efficiency to induce haploid formation.

In particular, the present methods do not rely solely on, in particular do not consist of, natural phenomena such as crossing or selection, but in fact are essentially based on the technical teaching so as to provide a specifically mutated nucleotide sequence prepared by mankind's contribution. Thus, the present invention introduces a specific structural feature, namely a mutation, into a nucleotide sequence and a plant of the present invention, which mutation is not caused by or associated with any natural phenomena such as crossing or selection.

In a particular embodiment of the present invention, which provides a method including a crossing step, said crossing step does not provide—such as a crossing usually does—heterozygous progeny but in fact homozygous progeny. Furthermore, the haploidy of progeny is not the result of the mixing of genes of the plants used for sexual crossing. Furthermore, the presently claimed process of generating a double haploid plant cannot be found in nature.

Further, the present invention also provides a method of facilitating a cytoplasm exchange, comprising the steps of:
x) crossing a plant according to the present invention as ovule parent to a plant expressing wildtype KNL2 protein as pollen parent, and
y) obtaining a haploid progeny plant comprising the chromosomes of the pollen parent and the cytoplasm of ovule parent.

In a preferred embodiment of the present invention, the method provided is not an essentially biological method. Said method is not a biological method essentially for the same reasons as indicated above, in particular since it is not entirely made up of natural phenomena such as crossing and selection, but involves as an essential feature a significant technical teaching so as to provide a particular mutation in a nucleotide sequence and a plant of the present invention. Furthermore, the haploidy of the progeny is not the result of the mixing of genes of the plants used for sexual crossing.

The method can advantageously be used to create cytoplasmic male sterility (CMS). CMS is caused by the extra-nuclear genome (mitochondria or chloroplasts) and shows maternal inheritance. Thus, the plant according to the present invention has to exhibit CMS and be the ovule parent of the cross. In this way CMS can be introduced into the crossing partner, preferably being an elite line of a crop.

In a preferred embodiment, the plant according to the present invention can also be used in a method to restore male fertility by providing a normal cytoplasm to a crossing partner that is CMS. Through such a cross the chromosomes of the CMS plant are introduced into the normal cytoplasm of the haploid inducer of the present invention which is not CMS. However, pollen production of the CMS plant has to be induced via temperature, light, length of day etc.

Without being bound by theory a possible model of how the present methods, in particular a method of uniparental chromosome elimination, works in inducer KNL2 x wild type KNL2 interspecific hybrid embryos is given in the figure. (A) Likely haploid inducer-derived egg cells contain either less KNL2 or compared to wild type a reduced unknown 'KNL2-transgeneration required signature'. A reduced amount of maternal KNL2 is less likely as according to studies performed with a KNL2-GFP reporter in *A. thaliana* plants sperm nuclei but not eggs cells are marked by KNL2. However, it is still possible that residual maternal KNL2s, generating a 'centromeric imprinting' are transmitted to the progeny. (B) Within a few hours after fertilization also paternal wild type KNL2 is actively removed from the zygote nucleus, and (C) centromeric reloading of KNL2-GFP in the zygote occurs at the 16-nuclei stage of endosperm development in *A. thaliana*. (D) In embryos undergoing haploidization centromeric reloading of the maternal chromosomes is impaired or delayed causing lagging chromosomes because of centromere inactivity during anaphase. Subsequently micronucleated haploid inducer chromosomes will degrade and (E) a haploid embryo will develop. Haploid embryos contain paternal-derived chromosomes in the background of maternal-derived cytoplasm.

The present invention also relates to a nucleotide sequence encoding at least the KNL2 protein, preferably the C-terminal region of the KNL2 protein, most preferably the CENP-C like motif of the KNL2 protein comprising at least one mutation causing in the KNL2 protein, preferably in the C-terminal region of the KNL2 protein, most preferably in the CENP-C like motif of the KNL2 protein an amino acid substitution.

The present invention also relates to a vector, in particular viral vector, construct or plasmid comprising said nucleotide sequence and, if present, associates sequences, preferably as indicated herein.

In a furthermore preferred embodiment of the present invention, the coding sequence of the KNL2 may be associated with regulatory elements, such as 5'- and/or 3'-regulatory elements, most preferably with a promoter, preferably a constitutive or inducible promoter.

Further, a plant cell comprising said nucleotide sequence or a vector comprising it as a transgene is provided by the present invention.

In the context of the present invention, the term 'comprising' as used herein is understood as to have the meaning of 'including' or 'containing', which means that in addition to the explicitly mentioned element further elements are possibly present.

In a preferred embodiment of the present invention, the term 'comprising' as used herein is also understood to mean 'consisting of' thereby excluding the presence of other elements besides the explicitly mentioned element.

In a furthermore preferred embodiment, the term 'comprising' as used herein is also understood to mean 'consisting essentially of' thereby excluding the presence of other elements providing a significant contribution to the disclosed teaching besides the explicitly mentioned element.

The present invention refers also to following aspects:

Aspect 1: Plant having biological activity of a haploid inducer and comprising a nucleotide sequence encoding a KINETOCHORE NULL2 (KNL2) protein, wherein the nucleotide sequence comprises at least one mutation.

Aspect 2: Plant according to aspect 1, wherein the amino acid sequence of the KNL2 protein is mutated.

Aspect 3: Plant according to aspects 1 or 2, wherein the mutation is a deletion, an addition or a substitution of at least one amino acid, preferably of one amino acid.

Aspect 4: Plant according to any of the preceding aspects, wherein the at least one mutation causes an amino acid substitution, deletion or addition which confers the biological activity of a haploid inducer.

Aspect 5: Plant according to any of the preceding aspects, wherein the KNL2 protein comprises a CENP-C like motif, especially a CENPC-k motif, and wherein the nucleotide sequence comprises at least one mutation in the CENP-C like, especially in the CENPC-k motif.

Aspect 6: Plant according to any of the preceding aspects, wherein the KNL2 protein comprises a CENP-C like motif and wherein the nucleotide sequence comprises at least one mutation causing in the CENP-C motif an amino acid substitution which confers the biological activity of a haploid inducer.

Aspect 7: Plant according to any of the preceding aspects, wherein the at least one mutation is in the C-terminal part of the KNL2 protein.

Aspect 8: Plant according to any of the preceding aspects, wherein the at least one mutation is a point mutation.

Aspect 9: Plant according to any of the preceding aspects, wherein the KNL2 protein comprises a CENP-C like motif and wherein the nucleotide sequence comprises a point mutation causing in the CENP-C like motif an amino acid substitution which confers the biological activity of a haploid inducer.

Aspect 10: Plant according to any of the preceding aspects, wherein the KNL2 protein comprises an amino acid sequence according to one of SEQ ID No. 23 to SEQ ID No. 123 or SEQ ID No. 164 to SEQ ID No. 274.

Aspect 11: Plant according to any of the preceding aspects, wherein the at least one mutation causes a substitution or deletion of a specified amino acid of SEQ ID No. 3 to SEQ ID No. 22 or SEQ ID No. 127 to SEQ ID No. 163.

Aspect 12: Plant according to any of the preceding aspects comprising also a nucleotide sequence encoding a centromer histone H3 (CENH3) protein comprising a CATD domain, wherein the nucleotide sequence comprises at least one mutation causing in the CATD domain an amino acid substitution which confers the biological activity of a haploid inducer.

Aspect 13: Plant according to any of the preceding aspects, wherein crossing between the plant and a wildtype plant or plant expressing wildtype KNL2 protein yields at least 0.1% haploid progeny.

Aspect 14: Plant according to any of the preceding aspects, wherein the nucleotide sequence comprising the at least one mutation is an endogenous gene or a transgene.

Aspect 15: Plant according to aspect 14, wherein the nucleotide sequence comprising the at least one mutation is a transgene and at least one endogenous gene encoding a KNL2 protein is inactivated or knocked out.

Aspect 16: Plant according to any of the preceding aspects, wherein the amino acid arginine at position 10 of SEQ ID No. 4 to SEQ ID No. 22 is deleted or substituted, preferably substituted for alanine.

Aspect 17: Plant according to any of the preceding aspects, wherein the amino acid tryptophan at position 19 of SEQ ID No. 4 to SEQ ID No. 22 is deleted or substituted, preferably substituted for arginine.

Aspect 18: Plant according to any of the preceding aspects, wherein the plant has one isoform of KNL2.

Aspect 19: Plant according to any of the preceding aspects, wherein the plant has two isoforms of KNL2.

Aspect 20: Plant according to any of the preceding aspects, wherein the plant has three isoforms of KNL2.

Aspect 21: Part of the plant according to any of the preceding aspects, which is preferably a shoot vegetative organ, root, flower or floral organ, seed, fruit, ovule, embryo, plant tissue or cell.

Aspect 22: Haploid plant obtainable by crossing a plant according to any of aspects 1 to 20 with a plant expressing wildtype KNL2 protein.

Aspect 23: Haploid plant obtainable by crossing in a first step a plant according to any of aspects 1 to 20 with a plant comprising a nucleotide sequence encoding a centromere histone H3 (CENH3) protein comprising a CATD domain, wherein the nucleotide sequence comprises at least one mutation causing in the CATD domain an amino acid substitution which confers the biological activity of a haploid inducer, and crossing in a second step a plant obtained in the first step with a plant expressing wildtype KNL2 protein and wildtype CENH3 protein.

Aspect 24: Double haploid plant obtainable by converting the haploid plant according to aspects 22 or 23 into a double haploid plant, preferably via colchicine treatment.

Aspect 25: A method of generating a haploid plant, comprising the steps of:
a) crossing a plant according to aspects 1 to 20 to a plant expressing wildtype KNL2 protein, and
b) identifying the haploid progeny plant generated from the crossing step.

Aspect 26: Haploid progeny plant generated in a method according to aspect 25.

Aspect 27: A method of generating a double haploid plant, comprising the steps of:
a) crossing a plant according to aspects 1 to 20 to a plant expressing wildtype KNL2 protein,
b) identifying a haploid progeny plant generated from the crossing step, and
c) converting the haploid progeny plant into a double haploid plant, preferably via colchicine treatment or via spontaneous chromosome doubling.

Aspect 28: Double haploid plant generated in a method according to aspect 27.

Aspect 29: A method of generating a haploid plant, comprising the steps of:
a) crossing a plant according to aspects 1 to 20 to a plant expressing wildtype KNL2 protein but comprising a nucleotide sequence encoding a centromer histone H3 (CENH3) protein comprising a CATD domain, wherein the nucleotide sequence comprises at least one mutation causing in the CATD domain an amino acid substitution which confers the biological activity of a haploid inducer,
b) crossing a plant obtained in step a) to a plant expressing wildtype KNL2 protein and wildtype CENH3 protein, and
c) identifying the haploid progeny plant generated from step b).

Aspect 30: Haploid progeny plant generated in a method according to aspect 29.

Aspect 31: A method of generating a double haploid plant, comprising the steps of:
a) crossing a plant according to aspects 1 to 20 to a plant expressing wildtype KNL2 protein but comprising a nucleotide sequence encoding a centromer histone H3 (CENH3) protein comprising a CATD domain, wherein the nucleotide sequence comprises at least one mutation causing in the CATD domain an amino acid substitution which confers the biological activity of a haploid inducer,
b) crossing a plant obtained in step a) to a plant expressing wildtype KNL2 protein and wildtype CENH3 protein,
c) identifying a haploid progeny plant generated from step b), and
d) converting the haploid progeny plant into a double haploid plant, preferably via colchicine treatment or via spontaneous chromosome doubling.

Aspect 32: Double haploid plant generated in a method according to aspect 31.

Aspect 33: A method of facilitating a cytoplasm exchange, comprising the steps of:
x) crossing a plant according to aspects 1 to 20 as ovule parent with a plant expressing wildtype KNL2 protein as pollen parent, and
y) obtaining a haploid progeny plant comprising the chromosomes of the pollen parent and the cytoplasm of ovule parent.

Aspect 34: Haploid progeny plant generated in a method according to aspect 33.

Aspect 35: A method of generating a plant according to aspects 1 to 20, comprising the steps of:
i) subjecting seeds of a plant to a sufficient amount of the mutagen ethylmethane sulfonate to obtain M1 plants,
ii) allowing sufficient production of fertile M2 plants,
iii) isolating genomic DNA of M2 plants and
iv) selecting individuals possessing at least one amino acid substitution, deletion or addition in KNL2, preferably in the C-terminal part of KNL2.

Aspect 36: Nucleotide sequence encoding the KNL2 protein or at least the C-terminal part of KNL2 protein comprising at least one mutation.

Aspect 37: Nucleotide sequence according to aspect 36, wherein the mutation causes in the C-terminal part an amino acid substitution, addition or deletion.

Aspect 38: Vector comprising the nucleotide sequence of aspect 36 or aspect 37.

Aspect 39: Plant cell or host cell comprising the nucleotide sequence of aspect 36 or 37 or the vector of aspect 38 as a transgene.

Aspect 40: A method of generating a plant according to aspects 1 to 20, comprising the steps of:
yy) transforming a plant cell with the nucleotide sequence of claim 36 or aspect 37 or the vector of claim 32, and
zz) regenerating a plant having the biological activity of a haploid inducer from the plant cell.

Aspect 41: The invention relates also to a haploid plant or double haploid plant obtainable by crossing in a first step a plant according to the invention with a plant comprising a nucleotide sequence encoding a centromere assembly factor or a spindle assembly checkpoint protein, wherein the nucleotide sequence comprises at least one mutation which confers the biological activity of a haploid inducer, and crossing in a second step a plant obtained in the first step with a plant expressing wildtype KNL2 protein and wildtype CENH3 protein.

Further preferred embodiments of the present invention are the subject-matter of the subclaims and the further independent claims.

The invention will now be described in some more detail by way of a non-limiting example and the figures.

The sequence protocol shows:

SEQ ID No. 1: the nucleotide sequence of the coding sequence (cDNA) of KNL2 from *Arabidopsis thaliana* (AT5G02520), SEQ ID No. 2: the amino acid sequence of the CENP-C motif of the CENP-P protein from *Arabidopsis thaliana*, SEQ ID No. 3: the amino acid sequence of KNL2 from *Arabidopsis thaliana* (AT5G02520), SEQ ID No. 4: the amino acid sequence of CENP-C like motif in KNL2 from *Arabidopsis thaliana*, SEQ ID No. 5: the amino acid sequence of CENP-C like motif in KNL2 from *Arabidopsis lyrata*

SEQ ID No. 6: the amino acid sequence of CENP-C like motif in KNL2 from *Capsella*

SEQ ID No. 7: the amino acid sequence of CENP-C like motif in KNL2 from *Glycine*

SEQ ID No. 8: the amino acid sequence of CENP-C like motif in KNL2 from *Glycine*_isoI SEQ ID No. 9: the amino acid sequence of CENP-C like motif in KNL2 from *Phaseolus*

SEQ ID No. 10: the amino acid sequence of CENP-C like motif in KNL2 from *Medicago* (2)

SEQ ID No. 11: the amino acid sequence of CENP-C like motif in KNL2 from *Medicago* (1)

SEQ ID No. 12: the amino acid sequence of CENP-C like motif in KNL2 from *Cicer*

SEQ ID No. 13: the amino acid sequence of CENP-C like motif in KNL2 from *Citrus sinensis*

SEQ ID No. 14: the amino acid sequence of CENP-C like motif in KNL2 from *Vitis*

SEQ ID No. 15: the amino acid sequence of CENP-C like motif in KNL2 from *Theobroma*

SEQ ID No. 16: the amino acid sequence of CENP-C like motif in KNL2 from *Solanum*

SEQ ID No. 17: the amino acid sequence of CENP-C like motif in KNL2 from *Populus*

SEQ ID No. 18: the amino acid sequence of CENP-C like motif in KNL2 from *Fragaria*

SEQ ID No. 19: the amino acid sequence of CENP-C like motif in KNL2 from *Fragaria*(1)

SEQ ID No. 20: the amino acid sequence of CENP-C like motif in KNL2 from *Amborella*

SEQ ID No. 21: the amino acid sequence of CENP-C like motif in KNL2 from *Physcomitrella*

SEQ ID No. 22: the amino acid sequence of CENP-C like motif in KNL2 from *Oryza*

SEQ ID No. 23: the amino acid sequence of a part of an artificial CENP-C like motif SEQ ID No. 24: the amino acid sequence of a part of an artificial CENP-C like motif SEQ ID No. 25: the amino acid sequence of a part of an artificial CENP-C like motif SEQ ID No. 26: the amino acid sequence of a part of an artificial CENP-C like motif SEQ ID No. 27: the amino acid sequence of an artificial KNL2

SEQ ID No. 28: the amino acid sequence of an artificial KNL2

SEQ ID No. 29: the amino acid sequence of an artificial KNL2

SEQ ID No. 30: the amino acid sequence of an artificial KNL2

SEQ ID No. 31: the amino acid sequence of an artificial KNL2

SEQ ID No. 32: the artificial amino acid sequence of an CENP-C like motif in KNL2 (*Arabidopsis thaliana*)

SEQ ID No. 33: the artificial amino acid sequence of an CENP-C like motif in KNL2 (*Arabidopsis lyrata*)

SEQ ID No. 34: the artificial amino acid sequence of an CENP-C like motif in KNL2 (*Capsella*)

SEQ ID No. 35: the artificial amino acid sequence of an CENP-C like motif in KNL2 (*Glycine*)

SEQ ID No. 36: the artificial amino acid sequence of an CENP-C like motif in KNL2 (*Glycine*_isoI)

SEQ ID No. 37: the artificial amino acid sequence of an CENP-C like motif in KNL2 (*Phaseolus*)

SEQ ID No. 38: the artificial amino acid sequence of an CENP-C like motif in KNL2 (*Medicago* 2)

SEQ ID No. 39: the artificial amino acid sequence of an CENP-C like motif in KNL2 (*Medicago*)

SEQ ID No. 40: the artificial amino acid sequence of an CENP-C like motif in KNL2 (*Cicer*)

SEQ ID No. 41: the artificial amino acid sequence of an CENP-C like motif in KNL2 (*Citrus_sinensis*)

SEQ ID No. 42: the artificial amino acid sequence of an CENP-C like motif in KNL2 (*Vitis*)

SEQ ID No. 43: the artificial amino acid sequence of an CENP-C like motif in KNL2 (*Theobroma*)

SEQ ID No. 44: the artificial amino acid sequence of an CENP-C like motif in KNL2 (*Solanum*)

SEQ ID No. 45: the artificial amino acid sequence of an CENP-C like motif in KNL2 (*Populus*)

SEQ ID No. 46: the artificial amino acid sequence of an CENP-C like motif in KNL2 (*Fragaria*)

SEQ ID No. 47: the artificial amino acid sequence of an CENP-C like motif in KNL2 (*Fragaria*1)

SEQ ID No. 48: the artificial amino acid sequence of an CENP-C like motif in KNL2 (*Amborella*)

SEQ ID No. 49: the artificial amino acid sequence of an CENP-C like motif in KNL2 (*Physcomitrella*)

SEQ ID No. 50: the artificial amino acid sequence of an CENP-C like motif in KNL2 (*Oryza*)

SEQ ID No. 51: the artificial amino acid sequence of an CENP-C like motif in KNL2 (*Arabidopsis thaliana*)

SEQ ID No. 52: the artificial amino acid sequence of an CENP-C like motif in KNL2 (*Arabidopsis lyrata*)

SEQ ID No. 53: the artificial amino acid sequence of an CENP-C like motif in KNL2 (*Capsella*)

SEQ ID No. 54: the artificial amino acid sequence of an CENP-C like motif in KNL2 (*Glycine*)

SEQ ID No. 55: the artificial amino acid sequence of an CENP-C like motif in KNL2 (*Glycine*_isoI)

SEQ ID No. 56: the artificial amino acid sequence of an CENP-C like motif in KNL2 (*Phaseolus*)

SEQ ID No. 57: the artificial amino acid sequence of an CENP-C like motif in KNL2 (*Medicago* 2)

SEQ ID No. 58: the artificial amino acid sequence of an CENP-C like motif in KNL2 (*Medicago*)

SEQ ID No. 59: the artificial amino acid sequence of an CENP-C like motif in KNL2 (*Cicer*)

SEQ ID No. 60: the artificial amino acid sequence of an CENP-C like motif in KNL2 (*Citrus_sinensis*)

SEQ ID No. 61: the artificial amino acid sequence of an CENP-C like motif in KNL2 (*Vitis*)

SEQ ID No. 62: the artificial amino acid sequence of an CENP-C like motif in KNL2 (*Theobroma*)

SEQ ID No. 63: the artificial amino acid sequence of an CENP-C like motif in KNL2 (*Solanum*)

SEQ ID No. 64: the artificial amino acid sequence of an CENP-C like motif in KNL2 (*Populus*)

SEQ ID No. 65: the artificial amino acid sequence of an CENP-C like motif in KNL2 (*Fragaria*)

SEQ ID No. 66: the artificial amino acid sequence of an CENP-C like motif in KNL2 (*Fragaria*1)

SEQ ID No. 67: the artificial amino acid sequence of an CENP-C like motif in KNL2 (*Amborella*)

SEQ ID No. 68: the artificial amino acid sequence of an CENP-C like motif in KNL2 (*Physcomitrella*)

SEQ ID No. 69: the artificial amino acid sequence of an CENP-C like motif in KNL2 (*Oryza*)

SEQ ID No. 70: the artificial amino acid sequence of an CENP-C like motif in KNL2 (*Arabidopsis thaliana*)

SEQ ID No. 71: the artificial amino acid sequence of an CENP-C like motif in KNL2 (*Arabidopsis lyrata*)

SEQ ID No. 72: the artificial amino acid sequence of an CENP-C like motif in KNL2 (*Capsella*)

SEQ ID No. 73: the artificial amino acid sequence of an CENP-C like motif in KNL2 (*Glycine*)

SEQ ID No. 74: the artificial amino acid sequence of an CENP-C like motif in KNL2 (*Glycine*_isoI)

SEQ ID No. 75: the artificial amino acid sequence of an CENP-C like motif in KNL2 (*Phaseolus*)

SEQ ID No. 76: the artificial amino acid sequence of an CENP-C like motif in KNL2 (*Medicago* 2)

SEQ ID No. 77: the artificial amino acid sequence of an CENP-C like motif in KNL2 (*Medicago*)

SEQ ID No. 78: the artificial amino acid sequence of an CENP-C like motif in KNL2 (*Cicer*)

SEQ ID No. 79: the artificial amino acid sequence of an CENP-C like motif in KNL2 (*Citrus_sinensis*)

SEQ ID No. 80: the artificial amino acid sequence of an CENP-C like motif in KNL2 (*Vitis*)

SEQ ID No. 81: the artificial amino acid sequence of an CENP-C like motif in KNL2 (*Theobroma*)

SEQ ID No. 82: the artificial amino acid sequence of an CENP-C like motif in KNL2 (*Solanum*)

SEQ ID No. 83: the artificial amino acid sequence of an CENP-C like motif in KNL2 (*Populus*)

SEQ ID No. 84: the artificial amino acid sequence of an CENP-C like motif in KNL2 (*Fragaria*)

SEQ ID No. 85: the artificial amino acid sequence of an CENP-C like motif in KNL2 (*Fragaria*1)

SEQ ID No. 86: the artificial amino acid sequence of an CENP-C like motif in KNL2 (*Amborella*)

SEQ ID No. 87: the artificial amino acid sequence of an CENP-C like motif in KNL2 (*Physcomitrella*)

SEQ ID No. 88 the artificial amino acid sequence of an CENP-C like motif in KNL2 (*Arabidopsis thaliana*)

SEQ ID No. 89: Artificial Amino acid sequence of CENP-C like motif in KNL2 (*Arabidopsis lyrata*)

SEQ ID No. 90: the artificial amino acid sequence of an CENP-C like motif in KNL2 (*Capsella*)

SEQ ID No. 91: the artificial amino acid sequence of an CENP-C like motif in KNL2 (*Glycine*)

SEQ ID No. 92 the artificial amino acid sequence of an CENP-C like motif in KNL2 (*Glycine*_isoI)

SEQ ID No. 93: the artificial amino acid sequence of an CENP-C like motif in KNL2 (*Phaseolus*)

SEQ ID No. 94: the artificial amino acid sequence of an CENP-C like motif in KNL2 (*Medicago* 2)

SEQ ID No. 95: the artificial amino acid sequence of an CENP-C like motif in KNL2 (*Medicago*)

SEQ ID No. 96: the artificial amino acid sequence of an CENP-C like motif in KNL2 (*Cicer*)

SEQ ID No. 97: the artificial amino acid sequence of an CENP-C like motif in KNL2 (*Citrus_sinensis*)
SEQ ID No. 98: the artificial amino acid sequence of an CENP-C like motif in KNL2 (*Vitis*)
SEQ ID No. 99: the artificial amino acid sequence of an CENP-C like motif in KNL2 (*Theobroma*)
SEQ ID No. 100: the artificial amino acid sequence of an CENP-C like motif in KNL2 (*Solanum*)
SEQ ID No. 101: the artificial amino acid sequence of an CENP-C like motif in KNL2 (*Populus*)
SEQ ID No. 102: the artificial amino acid sequence of an CENP-C like motif in KNL2 (*Fragaria*)
SEQ ID No. 103 the artificial amino acid sequence of an CENP-C like motif in KNL2 (*Fragaria*1)
SEQ ID No. 104: the artificial amino acid sequence of an CENP-C like motif in KNL2 (*Amborella*)
SEQ ID No. 105: the artificial amino acid sequence of an CENP-C like motif in KNL2 (*Physcomitrella*)
SEQ ID No. 106: the artificial amino acid sequence of an CENP-C like motif in KNL2 (*Arabidopsis thaliana*)
SEQ ID No. 107: the artificial amino acid sequence of an CENP-C like motif in KNL2 (*Arabidopsis lyrata*)
SEQ ID No. 108: the artificial amino acid sequence of an CENP-C like motif in KNL2 (*Capsella*)
SEQ ID No. 109: the artificial amino acid sequence of an CENP-C like motif in KNL2 (*Glycine*)
SEQ ID No. 110: the artificial amino acid sequence of an CENP-C like motif in KNL2 (*Glycine*_isoI)
SEQ ID No. 111: the artificial amino acid sequence of an CENP-C like motif in KNL2 (*Phaseolus*)
SEQ ID No. 112: the artificial amino acid sequence of an CENP-C like motif in KNL2 (*Medicago* 2)
SEQ ID No. 113: the artificial amino acid sequence of an CENP-C like motif in KNL2 (*Medicago*)
SEQ ID No. 114: the artificial amino acid sequence of an CENP-C like motif in KNL2 (*Cicer*)
SEQ ID No. 115: the artificial amino acid sequence of an CENP-C like motif in KNL2 (*Citrus_sinensis*)
SEQ ID No. 116: the artificial amino acid sequence of an CENP-C like motif in KNL2 (*Vitis*)
SEQ ID No. 117: the artificial amino acid sequence of an CENP-C like motif in KNL2 (*Theobroma*)
SEQ ID No. 118: the artificial amino acid sequence of an CENP-C like motif in KNL2 (*Solanum*)
SEQ ID No. 119: the artificial amino acid sequence of an CENP-C like motif in KNL2 (*Populus*)
SEQ ID No. 120: the artificial amino acid sequence of an CENP-C like motif in KNL2 (*Fragaria*)
SEQ ID No. 121: the artificial amino acid sequence of an CENP-C like motif in KNL2 (*Fragaria*1)
SEQ ID No. 122: the artificial amino acid sequence of an CENP-C like motif in KNL2 (*Amborella*)
SEQ ID No. 123: the artificial amino acid sequence of an CENP-C like motif in KNL2 (*Physcomitrella*)
SEQ ID No. 124: the artificial amino acid consensus sequence of 35 different plants
SEQ ID No. 125: the artificial amino acid consensus sequence of 7 different monocotyledonous plants
SEQ ID No. 126: the artificial amino acid consensus sequence of 17 different dicotyledonous plants
SEQ ID No. 127: the amino acid sequence of CENPC-k motif in KNL2 from *Arabidopsis thaliana*
SEQ ID No. 128: the amino acid sequence of CENPC-k motif in KNL2 from *Arabidopsis lyrata*
SEQ ID No. 129: the amino acid sequence of CENPC-k motif in KNL2 from *Capsella*
SEQ ID No. 130: the amino acid sequence of CENPC-k motif in KNL2 from *Glycine*
SEQ ID No. 131: the amino acid sequence of CENPC-k motif in KNL2 from *Glycine*_isoI
SEQ ID No. 132: the amino acid sequence of CENPC-k motif in KNL2 from *Phaseolus*
SEQ ID No. 133: the amino acid sequence of CENPC-k motif in KNL2 from *Medicago* (2)
SEQ ID No. 134: the amino acid sequence of CENPC-k motif in KNL2 from *Medicago* (1)
SEQ ID No. 135: the amino acid sequence of CENPC-k motif in KNL2 from *Cicer*
SEQ ID No. 136: the amino acid sequence of CENPC-k motif in KNL2 from *Citrus sinensis*
SEQ ID No. 137: the amino acid sequence of CENPC-k motif in KNL2 from *Vitis*
SEQ ID No. 138: the amino acid sequence of CENPC-k motif in KNL2 from *Theobroma*
SEQ ID No. 139: the amino acid sequence of CENPC-k motif in KNL2 from *Solanum*
SEQ ID No. 140: the amino acid sequence of CENPC-k motif in KNL2 from *Populus*
SEQ ID No. 141: the amino acid sequence of CENPC-k motif in KNL2 from *Fragaria*
SEQ ID No. 142: the amino acid sequence of CENPC-k motif in KNL2 from *Fragaria*(1)
SEQ ID No. 143: the amino acid sequence of CENPC-k motif in KNL2 from *Amborella*
SEQ ID No. 144: the amino acid sequence of CENPC-k motif in KNL2 from *Brachypodium*
SEQ ID No. 145: the amino acid sequence of CENPC-k motif in KNL2 from *Oryza*
SEQ ID No. 146: the amino acid sequence of CENPC-k motif in KNL2 from *Setaria*
SEQ ID No. 147: the amino acid sequence of CENPC-k motif in KNL2 from *Sorghum*
SEQ ID No. 148: the amino acid sequence of CENPC-k motif in KNL2 from *Musa*
SEQ ID No. 149: the amino acid sequence of CENPC-k motif in KNL2 from *Elaesis*
SEQ ID No. 150: the amino acid sequence of CENPC-k motif in KNL2 from *Phoenix*
SEQ ID No. 151: the amino acid sequence of CENPC-k motif in KNL2 from *Camelina*
SEQ ID No. 152: the amino acid sequence of CENPC-k motif in KNL2 from *Brassica*
SEQ ID No. 153: the amino acid sequence of CENPC-k motif in KNL2 from *Vigna*
SEQ ID No. 154: the amino acid sequence of CENPC-k motif in KNL2 from *Daucus*
SEQ ID No. 155: the amino acid sequence of CENPC-k motif in KNL2 from *Ziziphus*
SEQ ID No. 156: the amino acid sequence of CENPC-k motif in KNL2 from *Coffea*
SEQ ID No. 157: the amino acid sequence of CENPC-k motif in KNL2 from *Malus*
SEQ ID No. 158: the amino acid sequence of CENPC-k motif in KNL2 from *Pyrus*
SEQ ID No. 159: the amino acid sequence of CENPC-k motif in KNL2 from *Ricinus*
SEQ ID No. 160: the amino acid sequence of CENPC-k motif in KNL2 from *Nicotiana*
SEQ ID No. 161: the amino acid sequence of CENPC-k motif in KNL2 from *Gossypium*
SEQ ID No. 162: the amino acid sequence of CENPC-k motif in KNL2 from *Prunus*

SEQ ID No. 163: the amino acid sequence of CENPC-k motif in KNL2 from *Cucumis*
SEQ ID No. 164: the artificial amino acid sequence of CENPC-k motif in KNL2 from *Arabidopsis thaliana*,
SEQ ID No. 165: the artificial amino acid sequence of CENPC-k motif in KNL2 from *Arabidopsis lyrata*
SEQ ID No. 166: the artificial amino acid sequence of CENPC-k motif in KNL2 from *Capsella*
SEQ ID No. 167: the artificial amino acid sequence of CENPC-k motif in KNL2 from *Glycine*
SEQ ID No. 168: the artificial amino acid sequence of CENPC-k motif in KNL2 from *Glycine*_isoI
SEQ ID No. 169: the artificial amino acid sequence of CENPC-k motif in KNL2 from *Phaseolus*
SEQ ID No. 170: the artificial amino acid sequence of CENPC-k motif in KNL2 from *Medicago* (2)
SEQ ID No. 171: the artificial amino acid sequence of CENPC-k motif in KNL2 from *Medicago* (1)
SEQ ID No. 172: the artificial amino acid sequence of CENPC-k motif in KNL2 from *Cicer*
SEQ ID No. 173: the artificial amino acid sequence of CENPC-k motif in KNL2 from *Citrus sinensis*
SEQ ID No. 174: the artificial amino acid sequence of CENPC-k motif in KNL2 from *Vitis*
SEQ ID No. 175: the artificial amino acid sequence of CENPC-k motif in KNL2 from *Theobroma*
SEQ ID No. 176: the artificial amino acid sequence of CENPC-k motif in KNL2 from *Solanum*
SEQ ID No. 177: the artificial amino acid sequence of CENPC-k motif in KNL2 from *Populus*
SEQ ID No. 178: the artificial amino acid sequence of CENPC-k motif in KNL2 from *Fragaria*
SEQ ID No. 179: the artificial amino acid sequence of CENPC-k motif in KNL2 from *Fragaria*(1)
SEQ ID No. 180: the artificial amino acid sequence of CENPC-k motif in KNL2 from *Amborella*
SEQ ID No. 181: the artificial amino acid sequence of CENPC-k motif in KNL2 from *Brachypodium*
SEQ ID No. 182: the artificial amino acid sequence of CENPC-k motif in KNL2 from *Oryza*
SEQ ID No. 183: the artificial amino acid sequence of CENPC-k motif in KNL2 from *Setaria*
SEQ ID No. 184: the artificial amino acid sequence of CENPC-k motif in KNL2 from *Sorghum*
SEQ ID No. 185: the artificial amino acid sequence of CENPC-k motif in KNL2 from *Musa*
SEQ ID No. 186: the artificial amino acid sequence of CENPC-k motif in KNL2 from *Elaesis*
SEQ ID No. 187: the artificial amino acid sequence of CENPC-k motif in KNL2 from *Phoenix*
SEQ ID No. 188: the artificial amino acid sequence of CENPC-k motif in KNL2 from *Camelina*
SEQ ID No. 189: the artificial amino acid sequence of CENPC-k motif in KNL2 from *Brassica*
SEQ ID No. 190: the artificial amino acid sequence of CENPC-k motif in KNL2 from *Vigna*
SEQ ID No. 191: the artificial amino acid sequence of CENPC-k motif in KNL2 from *Daucus*
SEQ ID No. 192: the artificial amino acid sequence of CENPC-k motif in KNL2 from *Ziziphus*
SEQ ID No. 193: the artificial amino acid sequence of CENPC-k motif in KNL2 from *Coffea*
SEQ ID No. 194: the artificial amino acid sequence of CENPC-k motif in KNL2 from *Malus*
SEQ ID No. 195: the artificial amino acid sequence of CENPC-k motif in KNL2 from *Pyrus*
SEQ ID No. 196: the artificial amino acid sequence of CENPC-k motif in KNL2 from *Ricinus*
SEQ ID No. 197: the artificial amino acid sequence of CENPC-k motif in KNL2 from *Nicotiana*
SEQ ID No. 198: the artificial amino acid sequence of CENPC-k motif in KNL2 from *Gossypium*
SEQ ID No. 199: the artificial amino acid sequence of CENPC-k motif in KNL2 from *Prunus*
SEQ ID No. 200: the artificial amino acid sequence of CENPC-k motif in KNL2 from *Cucumis*
SEQ ID No. 201: the artificial amino acid sequence of CENPC-k motif in KNL2 from *Arabidopsis thaliana*,
SEQ ID No. 202: the artificial amino acid sequence of CENPC-k motif in KNL2 from *Arabidopsis lyrata*
SEQ ID No. 203: the artificial amino acid sequence of CENPC-k motif in KNL2 from *Capsella*
SEQ ID No. 204: the artificial amino acid sequence of CENPC-k motif in KNL2 from *Glycine*
SEQ ID No. 205: the artificial amino acid sequence of CENPC-k motif in KNL2 from *Glycine*_isoI
SEQ ID No. 206: the artificial amino acid sequence of CENPC-k motif in KNL2 from *Phaseolus*
SEQ ID No. 207: the artificial amino acid sequence of CENPC-k motif in KNL2 from *Medicago* (2)
SEQ ID No. 208: the artificial amino acid sequence of CENPC-k motif in KNL2 from *Medicago* (1)
SEQ ID No. 209: the artificial amino acid sequence of CENPC-k motif in KNL2 from *Cicer*
SEQ ID No. 210: the artificial amino acid sequence of CENPC-k motif in KNL2 from *Citrus sinensis*
SEQ ID No. 211: the artificial amino acid sequence of CENPC-k motif in KNL2 from *Vitis*
SEQ ID No. 212: the artificial amino acid sequence of CENPC-k motif in KNL2 from *Theobroma*
SEQ ID No. 213: the artificial amino acid sequence of CENPC-k motif in KNL2 from *Solanum*
SEQ ID No. 214: the artificial amino acid sequence of CENPC-k motif in KNL2 from *Populus*
SEQ ID No. 215: the artificial amino acid sequence of CENPC-k motif in KNL2 from *Fragaria*
SEQ ID No. 216: the artificial amino acid sequence of CENPC-k motif in KNL2 from *Fragaria*(1)
SEQ ID No. 217: the artificial amino acid sequence of CENPC-k motif in KNL2 from *Amborella*
SEQ ID No. 218: the artificial amino acid sequence of CENPC-k motif in KNL2 from *Brachypodium*
SEQ ID No. 219: the artificial amino acid sequence of CENPC-k motif in KNL2 from *Oryza*
SEQ ID No. 220: the artificial amino acid sequence of CENPC-k motif in KNL2 from *Setaria*
SEQ ID No. 221: the artificial amino acid sequence of CENPC-k motif in KNL2 from *Sorghum*
SEQ ID No. 222: the artificial amino acid sequence of CENPC-k motif in KNL2 from *Musa*
SEQ ID No. 223: the artificial amino acid sequence of CENPC-k motif in KNL2 from *Elaesis*
SEQ ID No. 224: the artificial amino acid sequence of CENPC-k motif in KNL2 from *Phoenix*
SEQ ID No. 225: the artificial amino acid sequence of CENPC-k motif in KNL2 from *Camelina*
SEQ ID No. 226: the artificial amino acid sequence of CENPC-k motif in KNL2 from *Brassica*
SEQ ID No. 227: the artificial amino acid sequence of CENPC-k motif in KNL2 from *Vigna*
SEQ ID No. 228: the artificial amino acid sequence of CENPC-k motif in KNL2 from *Daucus*

SEQ ID No. 229: the artificial amino acid sequence of CENPC-k motif in KNL2 from *Ziziphus*
SEQ ID No. 230: the artificial amino acid sequence of CENPC-k motif in KNL2 from *Coffea*
SEQ ID No. 231: the artificial amino acid sequence of CENPC-k motif in KNL2 from *Malus*
SEQ ID No. 232: the artificial amino acid sequence of CENPC-k motif in KNL2 from *Pyrus*
SEQ ID No. 233: the artificial amino acid sequence of CENPC-k motif in KNL2 from *Ricinus*
SEQ ID No. 234: the artificial amino acid sequence of CENPC-k motif in KNL2 from *Nicotiana*
SEQ ID No. 235: the artificial amino acid sequence of CENPC-k motif in KNL2 from *Gossypium*
SEQ ID No. 236: the artificial amino acid sequence of CENPC-k motif in KNL2 from *Prunus*
SEQ ID No. 237: the artificial amino acid sequence of CENPC-k motif in KNL2 from *Cucumis*
SEQ ID No. 238: the artificial amino acid sequence of CENPC-k motif in KNL2 from *Arabidopsis thaliana*,
SEQ ID No. 239: the artificial amino acid sequence of CENPC-k motif in KNL2 from *Arabidopsis lyrata*
SEQ ID No. 240: the artificial amino acid sequence of CENPC-k motif in KNL2 from *Capsella*
SEQ ID No. 241: the artificial amino acid sequence of CENPC-k motif in KNL2 from *Glycine*
SEQ ID No. 242: the artificial amino acid sequence of CENPC-k motif in KNL2 from *Glycine*_isoI
SEQ ID No. 243: the artificial amino acid sequence of CENPC-k motif in KNL2 from *Phaseolus*
SEQ ID No. 244: the artificial amino acid sequence of CENPC-k motif in KNL2 from *Medicago* (2)
SEQ ID No. 245: the artificial amino acid sequence of CENPC-k motif in KNL2 from *Medicago* (1)
SEQ ID No. 246: the artificial amino acid sequence of CENPC-k motif in KNL2 from *Cicer*
SEQ ID No. 247: the artificial amino acid sequence of CENPC-k motif in KNL2 from *Citrus sinensis*
SEQ ID No. 248: the artificial amino acid sequence of CENPC-k motif in KNL2 from *Vitis*
SEQ ID No. 249: the artificial amino acid sequence of CENPC-k motif in KNL2 from *Theobroma*
SEQ ID No. 250: the artificial amino acid sequence of CENPC-k motif in KNL2 from *Solanum*
SEQ ID No. 251: the artificial amino acid sequence of CENPC-k motif in KNL2 from *Populus*
SEQ ID No. 252: the artificial amino acid sequence of CENPC-k motif in KNL2 from *Fragaria*
SEQ ID No. 253: the artificial amino acid sequence of CENPC-k motif in KNL2 from *Fragaria*(1)
SEQ ID No. 254: the artificial amino acid sequence of CENPC-k motif in KNL2 from *Amborella*
SEQ ID No. 255: the artificial amino acid sequence of CENPC-k motif in KNL2 from *Brachypodium*
SEQ ID No. 256: the artificial amino acid sequence of CENPC-k motif in KNL2 from *Oryza*
SEQ ID No. 257: the artificial amino acid sequence of CENPC-k motif in KNL2 from *Setaria*
SEQ ID No. 258: the artificial amino acid sequence of CENPC-k motif in KNL2 from *Sorghum*
SEQ ID No. 259: the artificial amino acid sequence of CENPC-k motif in KNL2 from *Musa*
SEQ ID No. 260: the artificial amino acid sequence of CENPC-k motif in KNL2 from *Elaesis*
SEQ ID No. 261: the artificial amino acid sequence of CENPC-k motif in KNL2 from *Phoenix*
SEQ ID No. 262: the artificial amino acid sequence of CENPC-k motif in KNL2 from *Camelina*
SEQ ID No. 263: the artificial amino acid sequence of CENPC-k motif in KNL2 from *Brassica*
SEQ ID No. 264: the artificial amino acid sequence of CENPC-k motif in KNL2 from *Vigna*
SEQ ID No. 265: the artificial amino acid sequence of CENPC-k motif in KNL2 from *Daucus*
SEQ ID No. 266: the artificial amino acid sequence of CENPC-k motif in KNL2 from *Ziziphus*
SEQ ID No. 267: the artificial amino acid sequence of CENPC-k motif in KNL2 from *Coffea*
SEQ ID No. 268: the artificial amino acid sequence of CENPC-k motif in KNL2 from *Malus*
SEQ ID No. 269: the artificial amino acid sequence of CENPC-k motif in KNL2 from *Pyrus*
SEQ ID No. 270: the artificial amino acid sequence of CENPC-k motif in KNL2 from *Ricinus*
SEQ ID No. 271: the artificial amino acid sequence of CENPC-k motif in KNL2 from *Nicotiana*
SEQ ID No. 272: the artificial amino acid sequence of CENPC-k motif in KNL2 from *Gossypium*
SEQ ID No. 273: the artificial amino acid sequence of CENPC-k motif in KNL2 from *Prunus*
SEQ ID No. 274: the artificial amino acid sequence of CENPC-k motif in KNL2 from *Cucumis*

The material in the ASCII text file, named GLEISS1-59098-Corrected-Sequence-Listing 2, created Sep. 12, 2018, file size of 151,552 bytes, is hereby incorporated by reference.

The figures show:

FIG. 1a shows an alignment of the CENP-C motif of the *A. thaliana* CENP-C protein (SEQ ID No. 2) and the CENP-C like motif of *A. thaliana* KNL2 protein (SEQ ID No. 4);

FIG. 1b shows an alignment of the CENP-C like motifs of KNL2 homologues of different plants;

FIG. 2 shows a flow cytometry analysis of *Arabidopsis thaliana* seeds after crossing of knl2 mutant as female with the wild type male.

FIG. 3 shows a consensus sequence of the CENPC-k motif for plants (A), monocotyledonous plants (B) and dicotyledonous plants (C) as outlined in SEQ ID No. 124 to SEQ ID No. 126.

EXAMPLES

Example 1

A flow cytometry analysis of *Arabidopsis thaliana* seeds after crossing of knl2 mutant as female with the wild type male was done. For each sample 10 seeds were pooled together. Haploid picks are indicated on each histogram as shown in FIG. 2. Haploid induction efficiency was ~ 10%.

Example 2

The CENPC-k motif is required for the centromeric localization of KNL2 and functionally it can be replaced by the CENPC motif of CENP-C Mutational analysis has identified critical residues of the CENPC or the CENPC-v motif that are essential for centromeric localization of CENP-C, or for H3/cenH3 nucleosome binding. Two of these correspond to residues R546 and W555 of the *Arabidopsis* CENPC-k motif. The wild type C-terminal part of KNL2 fused to EYFP can localize to. R546 and W555 were mutated in this construct (KNL2(C)CENPC-k(R-A) and KNL2(C)CENPC-k(W-R)) to determine whether CENPC-k plays a similar role in KNL2 to the role of the CENPC and CENPC-v motifs in CENP-C. Additionally, the construct with complete deletion of the CENPC-k motif (KNL2(C) ΔCENPC-k) was generated. Analysis of transgenic *A. thaliana* plants expressing these constructs showed that the mutagenized KNL2 variants are unable to localize to chromocenters/centromeric sites. Fluorescence signals were detected in nucleoplasm and in nucleoli. These results suggest that the CENPC-k motif of KNL2 in general, and the conserved R546 and W555 amino acids in particular, are required for in vivo localization of KNL2 at centromeres of *A. thaliana*.

The inventors addressed the question whether replacement of CENPC-k by the CENPC motif of *A. thaliana* CENP-C(KNL2(C)CENPC) will restore the ability of KNL2 (C)ΔCENPC-k to localize to centromeres. Analysis of transgenic *A. thaliana* plants expressing the KNL2(C)CENPC construct has revealed that the CENPC motif is indeed able to target KNL2 to centromeres. Fluorescence signals were detected in nucleoplasm and at centromeres similar to the KNL2(C) control. In contrast to the mutagenized KNL2(C) variants, no fluorescence was detected in the nucleolus. These data suggest that CENPC motifs of KNL2 and of CENP-C proteins might play the same role in recognition of centromeric nucleosomes.

Additionally, leaves of *Nicotiana benthamiana* were transiently transformed by *Agrobacterium tumefaciens* with constructs expressing the wild type C-terminal part of KNL2, KNL2(C)ΔCENPC-k or KNL2(C)CENPC in a fusion with EYFP at their N- or C-termini, respectively. These constructs were expressed in *N. benthamiana* alone or in a combination with cenH3-mCherry. It was shown that in some cells the chimeric KNL2(C)CENPC protein is localizing to centromeres and co-localizing with cenH3 similar to the KNL2(C) with the native CENPC-k motif, while KNL2 (C)ΔCENPC-k protein was detected only in nucleoplasm and nucleolus. These data demonstrate that *A. thaliana* KNL2 can be targeted to centromeres of distantly related species such as *N. benthamiana* and that centromeric targeting requires presence of CENPC-k or CENPC motifs.

Example 3

The C-terminal part of *A. thaliana* KNL2 binds the centromeric repeat pAL1 DNA in vitro.

To test whether *A. thaliana* KNL2 interacts with the centromeric DNA despite of the absence of a distinct SANT/Myb domain, an electrophoretic-mobility shift assay (EMSA) with recombinant KNL2 protein fragments and centromeric repeat pAL1 DNA was performed. The N-terminal part of KNL2 including the SANTA domain and the C-terminus with the CENPC-k motif in fusion with a His-tag were separately expressed in *E. coli*. Soluble proteins were purified under non-denaturation conditions and used for a non-radioactive EMSA experiment with the centromeric repeat pAL1. The results showed that the mobility of pAL1 is shifted upwards only in the presence of recombinant C-, but not the N-terminal part of KNL2. The effect of KNL2(C) concentration on DNA binding was tested using constant amounts of pAL1 DNA and increased amounts of protein. The mobility of a portion of pAL1 DNA slightly shifted in cases of DNA:protein ratio 1:1 and 1:2, respectively, but with an increased amount of protein all pAL1 DNA was shifted upwards suggesting that one molecule of pAL DNA may be bound by several molecules of KNL2. In case of KNL2(N) no DNA binding was observed even in high excess of protein (DNA:protein 1:8) was applied. Additionally to the non-radioactive EMSA, we have employed the more commonly used radioactive variant and received similar results indicating that both methods have similar sensitivity.

Example 4

KNL2 binds non-centromeric sequences in vitro, but in vivo it associates preferentially with the centromeric repeat pAL1

To test whether the C-terminus of KNL2 interacts preferentially with centromeric repeats, we performed a competition experiment in which poly(deoxyinosinic-deoxycytidylic) acid (poly dI/dC) was used. The DNA binding capability of the C-terminal KNL2 to pAL1 was abolished by 50 ng/µl poly dI/dC. About 1-2.5 ng/µl poly dI/dC are usually used in EMSA to inhibit unspecific interactions. Next, we analyzed the interaction of KNL2(C) with repetitive elements such as the centromeric transposable element Athila, the telomeric repeat and the coding region of tubulin. The data showed that the C-terminus of KNL2 binds all non-centromeric DNA sequences that were used, albeit in a competition assay the euchromatic tubulin sequence TUA4 was bound with lower strength than repetitive sequences. Earlier it was shown that also CENP-C of maize binds DNA sequence-independently and that this DNA binding capability is stabilized by transcribed centromeric repeats and by small single stranded centromeric RNAs (ssRNAs). The inventors have identified a 23 nt ssRNA sequence for the centromeric repeat pAL1 from small RNA seq data of the wildtype and tested whether this ssRNA interacts with KNL2 and influences its binding capability to pAL1 in EMSA. However, the selected ssRNA showed an interaction with KNL2, but had no effect on binding of pAL1 by KNL2.

To analyze the interaction of KNL2 with DNA in vivo, chromatin immunoprecipitation (ChIP) was performed. Antibodies against KNL2 were purified by affinity chromatography and applied to chromatin isolated from seedlings of *A. thaliana* wild-type plants. Results showed that in vivo KNL2 binds preferentially the centromeric repeat pAL1 and to a much lower extent is associated with other sequences.

The invention claimed is:

1. Plant, wherein the plant comprises a nucleotide sequence encoding a KINETOCHORE NULL2 (KNL2) protein comprising a CENPC-k motif, wherein the nucleotide sequence comprises at least one mutation in the CENPC-k motif encoding sequence, and wherein the plant has biological activity of a haploid inducer.

2. Plant according to claim 1, wherein the at least one mutation is a deletion, addition or substitution of at least one nucleotide in the nucleotide sequence for the CENPC-k motif.

3. Plant according to claim 1, wherein the plant expresses a KNL2 protein having at least one amino acid addition, amino acid deletion and/or amino acid substitution in the CENPC-k motif.

4. Plant according to claim 1, wherein the KNL2 protein comprises an amino acid sequence according to one of SEQ ID No. 23 to SEQ ID No. 123 or SEQ ID No. 164 to SEQ ID No. 274.

5. Plant according to claim 1, wherein an amino acid arginine at position 10 of SEQ ID No. 4 to SEQ ID No. 22 is substituted, and/or wherein an amino acid tryptophan at position 19 of SEQ ID No. 4 to SEQ ID No. 22 is deleted or substituted, or wherein an amino acid arginine at position 8 or 7 or 6 of SEQ ID No. 127 to SEQ ID No. 163 is substituted, and/or wherein an amino acid tryptophan at position 17 or 16 or 15 of SEQ ID No. 4 to SEQ ID No. 22 is substituted.

6. Plant according to claim 1, wherein the wildtype CENPC-k motif comprises an amino acid sequence according to one of SEQ ID No. 124 to SEQ ID No. 126.

7. Plant according to claim 1, wherein the non-mutated CENPC-k motif comprises an amino acid sequence according to table 1

| Position | Amino acid |
|---|---|
| 1 | R or K |
| 2 | S or T |
| 3 | G |
| 4 | R |
| 5 | L or I or V or M or W |
| 6 | L or I or V |
| 7 | L or V |
| 8 | P or S or R |
| 9 | P or T or S or C or R or K |
| 10 | L or M |
| 11 | A or E or Q or D |
| 12 | F or Y of L or P or K or N |
| 13 | W or G | or table 2

| Position | Amino acid |
|---|---|
| 1 | S |
| 2 | G |
| 3 | R |
| 4 | V or L |
| 5 | V or I |
| 6 | V |
| 7 | P |
| 8 | P or T or K |
| 9 | L |
| 10 | D or A |
| 11 | L or P or K or N |
| 12 | G or W |
| 13 | C | or table 3

| Position | Amino acid |
|---|---|
| 1 | S |
| 2 | R |
| 3 | S or T |
| 4 | G |
| 5 | R |
| 6 | I or V or L or W or M |
| 7 | L or I |
| 8 | L or V |
| 9 | P or S or R |
| 10 | P or S or T or C or R |
| 11 | L or M |
| 12 | A or E or D or Q |
| 13 | F or Y |
| 14 | W |
| 15 | R or C or H |
| 16 | N |
| 17 | Q or E |

8. Part of the plant according to claim 1, which is a shoot vegetative organ, root, flower or floral organ, seed, fruit, ovule, embryo, plant tissue or cell.

9. Haploid plant obtainable by crossing a plant according to claim 1 with a plant expressing wildtype KNL2 protein, wherein the haploid plant retains the at least one mutation in the CENPC-k motif encoding sequence.

10. Haploid plant obtainable by crossing in a first step a plant according to claim 1 with a plant comprising a nucleotide sequence encoding a centromer histone H3 (CENH3) protein comprising a CATD domain, wherein the nucleotide sequence comprises at least one mutation causing in the CATD domain an amino acid substitution which confers the biological activity of a haploid inducer, and crossing in a second step a plant obtained in the first step with a plant expressing wildtype KNL2 protein and wildtype CENH3 protein.

11. Double haploid plant obtainable by converting the haploid plant according to claim 9 into a double haploid plant, wherein the double haploid plant retains the at least one mutation in the CENPC-k motif encoding sequence.

12. A method of generating a haploid plant, comprising the steps of:
 a) crossing a plant according to claim 1 to a plant expressing wildtype KNL2 protein, and
 b) identifying the haploid progeny plant generated from the crossing step.

13. A method of generating a double haploid plant, comprising the steps of: a) crossing a plant according to claim 1 to a plant expressing wildtype KNL2protein, b) identifying a haploid progeny plant generated from the crossing step, and c) converting the haploid progeny plant into a double haploid plant.

14. A method of generating a haploid plant, comprising the steps of:
 a) crossing a plant according to claim 1 to a plant expressing wildtype KNL2 protein but comprising a nucleotide sequence encoding a centromer histone H3 (CENH3) protein comprising a CATD domain, wherein the nucleotide sequence comprises at least one mutation causing in the CATD domain an amino acid substitution which confers the biological activity of a haploid inducer,
 b) crossing a plant obtained in step a) to a plant expressing wildtype KNL2 protein and wildtype CENH3 protein, and
 c) identifying the haploid progeny plant generated from step b).

15. A method of generating a double haploid plant, comprising the steps of:
 a) crossing a plant according to claim 1 to a plant expressing wildtype KNL2 protein but comprising a nucleotide sequence encoding a centromer histone H3 (CENH3) protein comprising a CATD domain, wherein the nucleotide sequence comprises at least one mutation causing in the CATD domain an amino acid substitution which confers the biological activity of a haploid inducer,
 b) crossing a plant obtained in step a) to a plant expressing wildtype KNL2 protein and wildtype CENH3 protein,
 c) identifying a haploid progeny plant generated from step b), and
 d) converting the haploid progeny plant into a double haploid plant.

16. A method of generating a plant according to claim 1, comprising the steps of:
 i) subjecting seeds of a plant to a sufficient amount of the mutagen ethylmethane sulfonate to obtain M1 plants,
 ii) allowing sufficient production of fertile M2 plants,
 iii) isolating genomic DNA of M2 plants and
 iv) selecting individuals possessing at least one amino acid substitution, deletion or addition in KNL2.

17. Plant according to claim 1, wherein an amino acid tryptophan at position 19 of SEQ ID No. 4 to SEQ ID No. 22 is substituted or wherein an amino acid arginine at position 8 or 7 or 6 of SEQ ID No. 127 to SEQ ID No. 163 is substituted and/or wherein an amino acid tryptophan at position 17 or 16 or 15 of SEQ ID No. 4 to SEQ ID No. 22 is substituted.

18. Plant according to claim 17, wherein the tryptophan at position 19 is substituted for arginine, the arginine at position 8 or 7 or 6 is substituted for alanine and/or the tryptophan at position 17 or 16 or 15 is substituted for arginine.

19. Plant, wherein the plant comprises a nucleotide sequence encoding a KI-NETOCHORE NULL2 (KNL2) protein, wherein the CENPC-k motif has been deleted and wherein the plant has a biological activity of a haploid inducer.

20. Plant according to claim 5, wherein the amino acid arginine at position 10 of SEQ ID No. 4 to SEQ ID No. 22 is substituted for alanine, and/or wherein the amino acid tryptophan at position 19 of SEQ ID No. 4 to SEQ ID No. 22 is substituted for arginine, or wherein the amino acid arginine at position 8 or 7 or 6 of SEQ ID No. 127 to SEQ ID No. 163 is substituted for alanine, and/or wherein the amino acid tryptophan at position 17 or 16 or 15 of SEQ ID No. 4 to SEQ ID No. 22 is substituted for arginine.

21. The method of generating a double haploid plant of claim 15, wherein the converting the haploid progeny plant into a double haploid plant is via colchicine treatment or via spontaneous chromosome doubling.

22. The method of generating a plant according to claim 16, wherein the at least one amino acid substitution, deletion or addition in KNL2 is in the C-terminal part of KNL2.

23. The method of claim 13, wherein the converting the haploid progeny plant into a double haploid plant is via colchicine treatment or via spontaneous chromosome doubling.

* * * * *